United States Patent [19]

Zupancic et al.

[11] Patent Number: 5,726,299

[45] Date of Patent: *Mar. 10, 1998

[54] PROMOTER DNA FRAGMENT FROM CORYNEFORM BACTERIA

[75] Inventors: Thomas J. Zupancic, Worthington, Ohio; Hideaki Yukawa, Inashiki-gun, Japan

[73] Assignee: Mitsubishi Chemical Corporation, Tokyo, Japan

[*] Notice: The term of this patent shall not extend beyond the expiration date of Pat. No. 5,693,781.

[21] Appl. No.: 285,641

[22] Filed: Aug. 1, 1994

Related U.S. Application Data

[63] Continuation-in-part of Ser. No. 76,091, Jun. 15, 1993, which is a continuation-in-part of Ser. No. 709,151, Jun. 3, 1991, abandoned.

[51] Int. Cl.⁶ .................... C07H 21/04; C12N 15/63
[52] U.S. Cl. ................ 536/24.1; 435/172.3; 435/320.1
[58] Field of Search ...................... 536/24.1, 23.1; 435/91.1, 91.21, 172.1, 172.3, 840, 843, 320.1

[56] References Cited

FOREIGN PATENT DOCUMENTS

| | | |
|---|---|---|
| 0530765 | 3/1993 | European Pat. Off. |
| 3147792 | 6/1991 | Japan . |
| 5015378 | 1/1993 | Japan . |
| WO8809819 | 12/1988 | WIPO . |

*Primary Examiner*—Nancy Degen
*Attorney, Agent, or Firm*—Sughrue, Mion, Zinn, Macpeak & Seas, PLLC

[57] ABSTRACT

Coryneform bacteria promoter DNA fragments are disclosed. The promoter function of the promoter DNA fragments is controllable by replacing at least one of the culture-medium ingredients with at least one other ingredient. The sizes and nucleotide sequences of such promoter DNA fragments are also disclosed.

13 Claims, 4 Drawing Sheets

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 128 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-128
        ( C ) IDENTIFICATION METHOD: experiment ( x i ) SEQUENCE DESCRIPTION:SEQ ID NO:1:

```
GATCCATGCA CGCGCGTTGC TCGGGCTGAA GGCCTGCTTC CACCTCAGCG GTGTGTTCAC     60
GGCGATCAAT TTCTTTACCA CCGAACACAT ATCCATCACT GGCCCATACT CACCCCGACC    120
TGTAGGAT                                                             128
```

( 2 ) INFORMATION FOR SEQ ID NO:2:

( i ) SEQUENCE CHARACTERISTICS:
        ( A ) LENGTH: 413 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-413
        ( C ) IDENTIFICATION METHOD: experiment ( x i ) SEQUENCE DESCRIPTION:SEQ ID NO:2:

```
GATCCACGCT GAGCATTTGA AAGTAACTAG TCCCGAAGAT CTTCGGAAAT GCATAAAGCA     60
AAAGGCTCTT AGTGGTTTGT CAGCGTATGA TCATCACGTA GAGTAACACC CAAGAGTAAG    120
ACGCAACATC AATCAATGTG CAAGGGTTTC ATTTCTGGAA ATCGTGGTCA CCCCACATTC    180
ACCAGTAATG AACAAGCTTG TTTAATGTGA ATTGGAGTA  GACCACATGC CCACTCTCGG    240
ACCATGGGAA ATTGGAATCA TTGTCCTGCT GATCATCGTG CTGTTCGGCG CGAAGAAGCT    300
GCCTGATGCA GCTCGTTCCA TCGGCCAGAT AACCCGCAGA TCAAGACATC AAACATTCGC    360
ACCATCGGAT TTCTCATCTA CGACGGCGTC TCACCCCTCG ATTTCACTGG ATC           413
```

( 2 ) INFORMATION FOR SEQ ID NO:3:

( i ) SEQUENCE CHARACTERISTICS:
        ( A ) LENGTH: 423 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
    ( A ) ORGANISM: Brevibacterium flavum
    ( B ) STRAIN: MJ-233

( i x ) FEATURE:
    ( A ) NAME/KEY: promoter
    ( B ) LOCATION: 1-423
    ( C ) IDENTIFICATION METHOD: experiment ( x i ) SEQUENCE DESCRIPTION:SEQ ID NO:3:

| | | | | | | |
|---|---|---|---|---|---|---|
| GATCCCTGCC | CAGGCGCGCG | CCCGTCCTGG | CGAGTTCGCA | GATCGAAGGG | TTTGAACACC | 60 |
| GTAGAGGGTG | GCGTCGACAA | GCAAATTTCT | GGTTTGCTGC | AAGCCTTGCC | CTGTACTGGT | 120 |
| GCGCCGCGCT | GTGGATCGCG | CTGGACGTTG | GGTATTTCTG | GGGCGACGCG | CTCTCGCGCA | 180 |
| CCCAAGGCGC | CCTATCCGCG | CTGTACTCGC | GCAACCCAC | GTTGTCGGCG | ATCGGTTACG | 240 |
| TGTTTACCCC | TCTGACCACC | GTGGTGCAGA | TTCCATTGGT | GGCGCTGAGC | CCTGGGTCC | 300 |
| CGGAATTCAC | GCGCGCCGGG | TTGGCAGGCG | CATTGGTGTC | ATCAGTGTTC | ATGGCGGCTT | 360 |
| CAGTGAGGCA | ATTGTGGTTG | ATTGCCAGCG | AGCGCAACAT | CCGGTATTGG | CTCGCGGTGG | 420 |
| TAG | | | | | | 423 |

( 2 ) INFORMATION FOR SEQ ID NO:4:

( i ) SEQUENCE CHARACTERISTICS:
        ( A ) LENGTH: 241 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-241
        ( C ) IDENTIFICATION METHOD: experiment ( x i ) SEQUENCE DESCRIPTION:SEQ ID NO:4:

| | | | | | | |
|---|---|---|---|---|---|---|
| GATCTTTCAG | CTGCTCACAC | GTGATTGTAC | CGCGTCAATG | GAAGTGATTG | GCCGCTTCCT | 60 |
| TGCCTTGCTG | GAATTGTATA | AGGCACGCGC | TATTGAAACC | TTGCAAGAGG | AGCCACTCGG | 120 |
| CGAGCTTAAA | GTTTCGTGGA | CTGGCATTGA | TGTCGATCCA | GCAGTCGTCG | CGGCGAGTGA | 180 |
| CTGGGAGTAA | TCAGTTTTTC | TTAAGGAAAC | GTTGCTGAAT | TAGTTTTAGT | GACCTAAGAT | 240 |
| C | | | | | | 241 |

( 2 ) INFORMATION FOR SEQ ID NO:5:

( i ) SEQUENCE CHARACTERISTICS:
        ( A ) LENGTH: 595 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-595
        ( C ) IDENTIFICATION METHOD: experiment ( x i ) SEQUENCE DESCRIPTION:SEQ ID NO:5:

| | | | | | |
|---|---|---|---|---|---|
| GATCTTGTCG | ACGCCGCCCG | CGACAGTGGC | GCACAAATCC | TCACGGGCGG | CCAACCCTCA | 60
| GATGGACCTG | GAAACTTCTA | TCCGGCCACG | ATTGTTACAG | ACATTGCTCC | GGATAATCCT | 120
| CTGGTTGTTG | AAGAACAGTT | CGGACCAGCG | CTTCCAATAG | TCCGATACTC | CAATATTGAT | 180
| GAAGCCATTG | GTTGGGCAAA | TGGACTTGAA | GTAGGTCTTG | GAGCTTCTGT | GTGGTCCGCT | 240
| GATCGGAATC | GCGCAATGGA | TGTAGCTAGG | CAGATTCAGG | CTGGAACAGT | ATGGATTAAT | 300
| AACCATGCCC | GCCCTGATCC | AAGAATTCCT | TTCGGCGGAA | TCAAGCAATC | GGGATACGGC | 360
| CTTGAATTTG | GTGCTGATGG | CCTCAAAGCG | GTTGCGGTCC | CCAAGGTCTA | CAACGGTTAA | 420
| TTGTTTGATG | TTGAGAATTC | TCCGGGCCGA | TTATTGTCGT | AGTTTCTGC | ATTGGTGCTT | 480
| GGCAAGGAGA | TCTGCCCCTG | GTAAAGCTTG | ATCAAATCGC | ATTTGACCAG | GGGATTTGGT | 540
| GTATTGTTAA | CTTGAAGGTA | GAGTATATTC | TCGTTCCTAA | AGGGGCCTAT | AGATC | 595

( 2 ) INFORMATION FOR SEQ ID NO:6:

( i ) SEQUENCE CHARACTERISTICS:
        ( A ) LENGTH: 588 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-588
        ( C ) IDENTIFICATION METHOD: experiment ( x i ) SEQUENCE DESCRIPTION:SEQ ID NO:6:

| | | | | | |
|---|---|---|---|---|---|
| GATCTGAAGC | AACACCTGAT | CAACCACACC | CCTTGGGGCG | CAAAGATCAC | GGTGGAGATC | 60
| GATGACATTA | ACCAACCGTT | CTCCACCGAT | ATTACCGGCC | CTGCAATGTC | CACCCTGGCG | 120
| TCCTGCCTGA | GCGCTGCGTA | CGAGGGCAAG | GATCTTGTCA | CCGAAGGCAG | CGGCGGATCC | 180
| ATTCCACTGT | GCACCGAACT | GATTGAGGTC | AACCCAGAAG | CAGAATTGGC | ACTCTACGGT | 240
| GTGGAAGAAC | CCCTCACCGT | TATCCACTCC | GCTAATGAAT | CTGTTGACCC | CAATGAGATT | 300
| CGCGATATCG | CCACCGCAGA | AGCATTGTTC | CTGCTCAACT | ACACCAAGTA | GACTTAGAAG | 360
| CAGGCATTAA | CACTGCCACC | TTTGCAAAAT | TAACCACCCC | CTGATGGGGT | GGTTTTTTCA | 420
| TGAGTTGAAA | AAAGTGTCTT | GATTCACTTT | GTGATGACGG | TTACCATAGC | CATCGTGACT | 480
| AAAAACATTG | ACCTTAAGCG | AGTAGCCAAG | GCTACGTACC | CTACTGCGGG | ATAGATGGAC | 540
| TGGCTCCCCG | CACTAGGGAA | GTAGTCGTTA | ATCAACACCA | AGAAGATC | | 588

( 2 ) INFORMATION FOR SEQ ID NO:7:

( i ) SEQUENCE CHARACTERISTICS:
        ( A ) LENGTH: 432 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
    ( A ) NAME/KEY: promoter
    ( B ) LOCATION: 1-432
    ( C ) IDENTIFICATION METHOD: experiment ( x i ) SEQUENCE DESCRIPTION:SEQ ID NO:7:

| | | | | | |
|---|---|---|---|---|---|
| GATCTAACG | TTTAGCGGCT | CTCTGGATCG | TGAAATGTCA | ACGTTCATGG | AAGCCAATGT 60 |
| AGTGGGGTCG | CGTCGAAAAG | CGCGCTTTAA | GGGCGACACG | CCCAAAAAGT | TTTACCTTTA 120 |
| AAAACTACCC | GCACGCAGCA | CGAACCTGTT | CAGTGATGCA | AATCACCGCT | AAAATATTGT 180 |
| GGACGTTACC | CCCGCCTACC | GCTACGATTT | CAAAACATGA | CCATTTCCTC | ACCTTTGATT 240 |
| GACGTCGCCA | ACCTTCCAGA | CATCAACACC | ACTGCCGGCA | AGATCGCCGA | CTTTAAGGCT 300 |
| CGCCGCGCGG | AAGCCCATTT | CCCCATGGGT | GAAAAGGCAG | TAGAGAAGGT | CCACGCTGCT 360 |
| GGACGCCTCA | CTGCCCGTGA | GCGCTTGGAT | TACTTACTCG | ATGAGGGCTC | CTTCATCGAG 420 |
| ACCGATCAGA | TC | | | | 432 |

( 2 ) INFORMATION FOR SEQ ID NO:8:

( i ) SEQUENCE CHARACTERISTICS:
        ( A ) LENGTH: 858 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-858
        ( C ) IDENTIFICATION METHOD: experiment ( x i ) SEQUENCE DESCRIPTION:SEQ ID NO:8:

| | | | | | |
|---|---|---|---|---|---|
| CCGTTATATA | TAAGGAATAG | GCAACAAGTC | CCACTGGCTG | TGCCAATAGC | CAGCACACAA 60 |
| ACATTGAATC | CCCACAGATC | ATCACCCAAA | ACTACGGGGC | TTGCAGTTCC | AATGCGATCA 120 |
| AACCCATGGA | CAACATTGCC | ATGCGGATGC | TTCAGTTTTG | AATGAGGAGA | GCGGTAGATT 180 |
| AGCCAACCGT | CAATTAATGA | CAATTGCCAC | CACAACAGCT | AACGCGAAGA | AGAAATCTGC 240 |
| GACGACTGGA | AAACCATGGA | TTTTCAACAG | TGATGACAAC | AATGAGATGC | CCATGAGGGA 300 |
| ACCAGCCCAC | GAGGGGCCCC | TTTGTGACAT | CGGCGTAGTT | GTTCAACTAT | AATGGAACGC 360 |
| TGATCGTGGA | CAAGAGTTAA | CCATGAGATT | GATTCACCCC | TTTAAGCCTC | CAAAGAAGTA 420 |
| GTTGACTCAA | CGCATTTCGG | CATTTAAAAA | AGCCGAGAGC | AAATGAGACT | TTCCAGGAGA 480 |
| AGGCACCAGG | GACATGAACA | ATTGATCGGC | TGACCAACTC | TATAAGAGAT | GCACCTCAAG 540 |
| TTTGGGGATA | CTTATTCGGC | GTTTCTGGGG | ACAAATACGT | TCCCTATTGT | TGTATATAGG 600 |
| TATTCGCACT | TAAGAAACAT | CTCTCATGGA | AAGAAGCTAG | GCGGAAAGGG | CGTTAAGTAC 660 |
| TTGCCATTTA | ATCCTCAGCA | TCACTCGGAT | CAGTCGGAGA | TGTCGATGAA | AATGCACCAG 720 |
| GAGCCGTGGA | GAGCAGCATG | GTAGAAAACA | ACGTAGCAAA | AAAGACGGTC | GCTAAAAAGA 780 |
| CCGCACGCAA | GACCGCACGC | AAAGCAGCCC | CGCGCGTGGC | AACCCCATTG | GGAGTCGCAT 840 |
| CTGAGTCTCC | CATTTCGG | | | | 858 |

( 2 ) INFORMATION FOR SEQ ID NO:9:

( i ) SEQUENCE CHARACTERISTICS:
        ( A ) LENGTH: 1187 base pairs (B) TYPE: nucleic acid
(C) STRANDEDNESS: double
(D) TOPOLOGY: linear (i i) MOLECULE TYPE: genomic DNA (v i) ORIGINAL SOURCE:
(A) ORGANISM: Brevibacterium flavum
(B) STRAIN: MJ-233

(i x) FEATURE:
(A) NAME/KEY: promoter
(B) LOCATION: 1-1187
(C) IDENTIFICATION METHOD: experiment (x i) SEQUENCE DESCRIPTION:SEQ ID NO:9:

| | | | | | |
|---|---|---|---|---|---|
| TTACCGCAAG | CTCAATACGA | CTCACTATAG | GGGCCCGGTA | CCGAGCTCAC | TAGTTTAATT  60 |
| AAAAGCTTAT | CGGCCTGAGG | TGAGAAGGGT | TCCGGACCCC | AGAATTCTCG | CGATAATTAA 120 |
| TTAATAGCCC | GCCGTAATGA | GCGGGCTTTT | TTTGATCCC  | CGCCACCATA | ACCCACGAAT 180 |
| CCTAACAAGT | CCCTGCATTC | TCGATGGCTT | TTTGGCTTTA | ATCCGTTTTG | GTTCAGGAAA 240 |
| CTTACAAGAT | CTTTTACGCT | AGATGAAACT | TGCCATCGAA | CAGAATCCTG | CAGATGAAAT 300 |
| CTTTCAGCAC | CATACATATC | GGTAATTCAT | AAAATGCTCC | AGTGTCAAGC | TCTCGCAACG 360 |
| TAATCGTTGC | TGTTCACGGA | GTTCTTACTA | GCTGCTCGGG | CGATCAATTT | GTCATTAGAT 420 |
| TATGCAGTTA | TAGGGAGAAC | GGACACAAAA | GGGAGGGACC | TGACTGTACA | CTGTACTCCC 480 |
| GCTAGCACGT | GTGTGTGATG | ACACAGCTCA | GAAGCATTGC | AGTTGGACAA | CCCCTAGATA 540 |
| AGACTGCGCA | AAGTAGGACA | TATCTCTCAC | TTTTCTTATT | GTTTCGGGC  | AAAACTAATC 600 |
| CAGAACCTTT | CTAAAGGCCC | TGATCAATCA | GGATTTCTGC | GTGTCGACGT | GATGCCACAC 660 |
| CTGCTTGGGC | AAGCACCTTC | TGCAGGCGAA | CTCCGTCAGA | GTCATTGCGG | CTTAAGAAAC 720 |
| CCATCGACCA | ATCGTCGTCG | GATTTACGT  | TTTGCTTCTT | GGCAGGCTTA | GCGTTGGAGA 780 |
| GAAGAATCTC | ATCCTTCTTC | TGAGGCTGCT | GGCGTGTGTT | TGGGCGGGAT | GATCCTGGCT 840 |
| TGTAGCCACG | AACTGAAGAC | CGGTATCCGC | CAGAGCGATT | GCTCTGCTTC | TTGTCCGGTG 900 |
| TGCCATCTCG | GCGAGCGGGT | GGGGTCACGT | AAGTGTCCTT | AATCTTGAGA | GAAACGTAT  960 |
| GAAATTGAAT | CCCGTGAATT | CTAGCCTATT | TTAGGAGATT | TTAATAGTCG | GGGCTTTAAC 1020 |
| TGATGCTTTA | GAAGTCTTCA | TCAATGGAGT | CAACATCCGG | CAAAAGCGGT | GCTAGATCCG 1080 |
| GTAATTTATC | CAAAGAATCA | ATACCCAACA | GCTCAAGCAG | GCAATTCCCG | TTGTGCCCAT 1140 |
| AGCGGTGCGC | GCCCGTTGAT | TCGTCCACAT | CGACTTCTTT | GACTAGG    |           1187 |

(2) INFORMATION FOR SEQ ID NO:10:

(i) SEQUENCE CHARACTERISTICS:
(A) LENGTH: 713 base pairs
(B) TYPE: nucleic acid
(C) STRANDEDNESS: double
(D) TOPOLOGY: linear (i i) MOLECULE TYPE: genomic DNA (v i) ORIGINAL SOURCE:
(A) ORGANISM: Brevibacterium flavum
(B) STRAIN: MJ-233

(i x) FEATURE:
(A) NAME/KEY: promoter
(B) LOCATION: 1-713
(C) IDENTIFICATION METHOD: experiment (x i) SEQUENCE DESCRIPTION:SEQ ID NO:10:

| | | | | | |
|---|---|---|---|---|---|
| CTCAATTGCC | TCGTCTGAAG | GATGCTGACA | CTGAACTGAC | AGACGAGGAC | CGGGCCTAAG 60 |

```
ATTTTTTCGG TGTATGGCGC GGGCTGTGAG GGGGATGTCG TCGATAAGCG TAGGGCCGAA  120
GAAGAAGCCC TCCTCGTGCC GTCTACGGCT GCACGTTACG CCGTCCACGA CTGATCTTGG  180
CAGCCGGTCT GGCCTCAGCG ATGCGACATA AGAAGCGACC TTCTCGCGGT GGCTGCGGTG  240
ATTAGTGGGC CCAGGTCCGC TCAGCCTGCT CGCGCCGGCA CCGTTGCCGA TGCGAAGGGT  300
GTCGATGCGG TCCTTGATCT TCTCAATGAG CTTTATTCCT GGGCTTTGGG AGCTTCAAAC  360
AGGAGGCATC AAATTTGGGG TAGTGCAGGG CCTTTGAATC CCACCTCACA GATAGTATTC  420
AGGCATTTCC TTGTCACGAT GGTTTATCCT TGGACACAAC ATCAAAAGTG GGTACATCA   480
TATGCTTCCG GTTGAAAGTG ACCTATCTGA AAAGACTTGG CAGAACCTTA AGCAATGGTG  540
TGAACTGCGT TAACGAATTT TGTCGGACGT TAAAATGGCG CATTCTGCTT GCTGAAGTGG  600
CACACCTATG TGTTCTGCTT GGGATAGCAG TGCGGGAAAA ATTTGAAAAA GTCCGATTAC  660
CTTGAGGAGT ATTCAATGTC ATGACGCATT GCTTCAGAAA ACTGCGCTCC AAG         713
```

( 2 ) INFORMATION FOR SEQ ID NO:11:

( i ) SEQUENCE CHARACTERISTICS:
        ( A ) LENGTH: 1006 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-1006
        ( C ) IDENTIFICATION METHOD: experiment ( x i ) SEQUENCE DESCRIPTION:SEQ ID NO:11:

```
CTGAAGGAGT ACACCTTCGA TCTGCTCTAC AGATCTTTAG TGATAACAGA AACTCAGTAC   60
TCCGAAGATC TCTACTGACA GATCTTGGAT GGACCCGAGG ATGTTAAAGC GATTCCCTTC  120
GCTACAACAG CAACAAGGCC CTCAACAACC TTGGCTACGA AGGACTCTTC CCAGCGGATG  180
AAACCAAGGT GTCCCCAAAC ATCTTGTCTG CGCTGTCACC AAACGCTGAT GAGAACCACG  240
ACTTCTTCTC CGGCTCCGGT TCCTCTTACG TTATTGGTAA GGCAGAAAAC ACCCGAGGAT  300
GATGACCTGG GACTTTCTAA CTTTTAAAAA GCTGAAGCGG TCTACCGGCC TGTAGGGTAA  360
CCTCAACCCG TTAGAGCGTT TTCGGGTTTC CTGGTGGGA  CTTAAAGGTG CGGGGTTTTC  420
CGAAGCCGCA ATATCAGGGG TAAGGGACGA CCAGGCACCC CTGTGGCCCC TCGGCAGCGC  480
ATCACGCTTT AGGAGAAAAC GCCCCTGGAA TGGCGTCTCA ACCATTCAGA TTGAACCCCG  540
GCAGGGGGA  ATTATGAAAT CTGTGACAGG GGTTAACCGT GGGGGTGGGC TTCCTGGCAG  600
AAATGTCCGT CAAATTGTGA ACCCCTTCAC ACCTTTGGTT GAAAGCACTG CCCACAAGTG  660
ACTGAACCTG GCAGCGACCT CATGAATTGT TTGAAAAACA TTTTTTTTGG CACGAAAACG  720
GGATACACG  TTAGCTGCAT ACCAGCCTTT TTGGGTTGCA TCAGGATCCT GCCTGTGGCC  780
TTATGATCAG GCAGTGTTGT TAAAGGACGA TCGGTAATCC GAATGGTTCG TCCCGTAGTC  840
AGGAGGAACC TATGACCGCT GTGGCGCCTA GGGTCGACGG GCACGTGCCC CTCTACGAGG  900
CCCGAGCCCG ACAGGCCATG CACGCAAGGG CAGAAAGCAT GGTTAATGAT GACCACCACC  960
GGACCACAAG CAGCTTGGGC ATTATGTACA TCATTATGTC CTTCAG              1006
```

( 2 ) INFORMATION FOR SEQ ID NO:12:

( i ) SEQUENCE CHARACTERISTICS:
        ( A ) LENGTH: 737 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-737
        ( C ) IDENTIFICATION METHOD: experiment ( x i ) SEQUENCE DESCRIPTION:SEQ ID NO:12:

```
CTGCGTTGGC CTTAAGGGAG ATCACTTCAA TTTCTTCATT GTGAGGCAGC CAGAACTCCA     60
CCACCTTTTC CTGCTCTGAA AGTCCATCCA CTGTGAAGCA CCTGCGGATC TTCCAGACGC    120
CGTTCCGTGG CGCCGGTGAT GAAATTGACT TCCGTGGTCT CGCCCCCGGA GGTTGGCGTG    180
GAAGATGTGG GGGCGCCGTC GATAAGCACA TCAATCTTGC CGCCCGGCCG GCCGGAATCG    240
AGGTACACCA CCGAGTGGAN TACGTGGTCA GCGTGAAGGA GGTGGCGGTT GGTGCGACAC    300
ACACGGCACG CCCGTTGGTT GGCGTTCCAT CGCGCTAACT TGGGATCACA GTACGGTCTA    360
CTTATTCCTT TGCTGAGCCA ATCGGGCGAA GGCCCCTTGT TAGTGGTTCA ATTTCGGTTG    420
CGCCGTGAAT TAAATTCGGG ATTTCATGAG CTTAACCGTA CCGCTCTTGC AGAGTTCACA    480
GGGTAAACCC TAAATGGAAC AACCCATTGC CAATATGTTG GTTAAGTTGT ACGCAAGTAA    540
ATCTTTTCAA TCGTGGAAGC AGGGCTCACA GTCTAATGGC ACGTATGCAG GAAAGCGCCG    600
ATCTTCCAAA TGTTCCTTCT GCGGAAAGAG CCAAAAGCAG GTAAAAAAAC TTCATCGCGG    660
GTGGCGCCGG TATATATCTT GTGATGAGTG CATTGAGCTT GTGCAACGAG ATTATTGAAG    720
AAGAACTCAG GTCAAGA                                                  737
```

( 2 ) INFORMATION FOR SEQ ID NO:13:

( i ) SEQUENCE CHARACTERISTICS:
        ( A ) LENGTH: 2203 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-2203
        ( C ) IDENTIFICATION METHOD: experiment ( x i ) SEQUENCE DESCRIPTION:SEQ ID NO:13:

```
CTACTTCTTC TTCACCGAAG TATTCCTTAG GGTCGATCTC GTTACCCTCG GAGTCCTTCA     60
CGTTTACGCG GCAGATAGCC TGTGCAAGAG CCTTGCCACG GCGAACGTCG GAGAAGAGGT    120
TCGCGATCTG GCCGGACTGC TGCAGCTGAC CGATGAACTG GTTTGGGTCC ATGCCGTAAG    180
ACTGTGCGGT GAACAGGATG TGGTCGGTGA GCTCCTCGTG CCGCTGATGC GACTTCGAGT    240
CCGATCCAGC CACCACCGAT GAGGACCAGC TTTTTACCTT CACCGAAGTT GCCTTGATCG    300
CGTCAGAGTC TTCCACGGCG CGCAGGTAGT GCACATTAGA GCCGTCGGCT CCGGAATTGG    360
```

-continued

```
AAGTTTGCGA CTGCTGAGCA AGTAGCAAGA ACTAGTTTGT CGTAGTTAAT GGTCTCAGTG     420
TTTCCGCCAT CATCAACGGT GACTTGGCGT GAACCCGCAT CAATTGCCGT GACGCACACC     480
TTGACGCAGC GTGACATTGT TTTCTTTGTA CCACCCCGCC GGGTGAACAA TCGCCTTTTC     540
AAAGCCTACT TTTCCCGCCA TGTACTCCTT TGACAGCGGT GGGCGTTCAT ATGGCAGATG     600
ATTTTCTGCT GCGATGAGCG TGATGGAGCC TTCATGCCCG TTTACACGCA GTGCCTCTGC     660
GGTTTTCGCT CCGGCTGAAC CGCCGCCGAT GATGACGATG CTTTGTGGTG TGCTCATGCT     720
GTACTCCTAG TCCCTAAAAA GTGGACGGTC AGGCGCAAGG TCGACCGCAT GGTCTATACG     780
CCATGCTAGT TAAAAGGCCG AAACCCTCGG CGAGCGCGCT AAATACCCGG CCCCAATTGG     840
GGGTGTGAGG CAGCACACAA GACGAAACCC TAACGAAATC GCCAGACTCC TCGCAATCAC     900
AAGAAGCGAC GACTAGCCTG TGGGACAAA CTATCTCAAG AATTTATTCA ACAAAGGAGT      960
TCTTCGCACA TGAAGGAAGT AGCAGTCAAC GAAGTCCCAG CAGGCGCGCA GCTAATGCAC    1020
TGTCACTGTT TCGACGTGAT GTGCATCGGT TTACGTGGTG GCGTGGTTCA CACATTGCTC    1080
CATCGGGCAT TGGTGCGTCA ATCGGTTTGG GTTTTAAGT TTTGTGCGGG GGTGGTCACC     1140
CCTGTTGTGA ACTTTGCAAA GTTATGACTT CGCAGAAAAA GTCGGCGGGG GAGTTGCTAG    1200
TACGGATGTA CTGGGCAAAT GCTCTGAAAT GGGAAAATGC AGGCACCACA ACTTTCCGTA    1260
GTTTTGAAGG TGTGACCTAG ATAAAAGTCG GGGTTAGGCG GGGGTAAATG ACTAGGTAAA    1320
GGTTCGCAAA CCCCCTTTTG TTGGTGACGG TGATCACTTA GTCTGATCAC ATCGCCAAAC    1380
ACGATAAGGG TTGAAATCGA AAGAAGAGCG GCACCTAGAT TCCAGAGGTA GCCAGAGTGC    1440
TTTTCTTAAA AGAGTTTTCA CAACCGTTAA CGGCGTAGCC AAACAAGAAG GATTCGCATT    1500
NCAGCTTCTG GTTTAGGCAC AGGTCATCTA AAACCCATGC TTTAAAAGGA GCCTTCAATG    1560
ACTGAACAGG AACTGTTGTC TGCTCAGACT GCCGACAACG CTGGAACTGA CAGCACCGAA    1620
CGCGTTGACG CGGGCGGAAT GCAGGTTGCA AAAGTTCTCT ACGACTTTGT AACCGAAGCG    1680
GTACTCCCTC GCGTGGGTGT GGATGCGGAA AAGTTCTGGT CCGGATTCGC CGCCATCGCC    1740
CGGGACCTCA CCCCACGCAA CCGCGAACTG CTTGCTCGTC GCGATGAACT GCAGACGCTT    1800
ATCGACGACT ACCACCGCAA CAACTCCGGC ACCATCGACC AAGACGCGTA CGAGGATTTC    1860
CTTAAAGAAA TCGGATACTT GGTTGAGGAG CCAGAAGCTG CAGAAATCCG TACCCAAAAC    1920
GTCGATACGG AAATCTCCAG CACCGCAGAC CTCAGCTGGT TGTGCCAATT CTGAACGCAC    1980
GTTCGCGCTG AATGCTGCCA ATGCTCGTTG GGGTTCCCTC TACGATGCGT TGTACGGCAC    2040
CAACGCCATC CCAGAAACTG ATGGCGCTGA AAAGGGCAAG GAGTACAACC CGGTCCGCGG    2100
CCAGAAGGTC ATCGAGTCGG GTCGTCAATT CCTCGACAGC GTTGTCCCAC TGGACGGGTG    2160
CTTCGCATGC CGATGTTGAG AAGTACAACA TCACGGATGG AAA                      2203
```

( 2 ) INFORMATION FOR SEQ ID NO:14:

( i ) SEQUENCE CHARACTERISTICS:
        ( A ) LENGTH: 551 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter (B) LOCATION: 1-551
(C) IDENTIFICATION METHOD: experiment (xi) SEQUENCE DESCRIPTION:SEQ ID NO:14:

```
CCTCATGGAT GTTGACATCG ATATGGATTC CGACATCTGA GCAGATCCTC TCCTGGCGGA    60
CACAGACGCA TCCCTGCTCT CCCTGGAAGC TGGCACCTGT GACCGTTGCC TTCGACACGA   120
CACATGCTGA CCACCCTGGA GAACTCCGGC CTATCGTGCC GATCGTTCCA GGCGCTGTGA   180
TTTTTGATTT GTTGGTGGGC GATCCCAAAA ACAGGCCGCT GAGAAAGTTT TCCACACTAA   240
AATAGTGTGA TTCTGCCGAA TCTGTTGTTT TACTTTGAA  ACTGCGGGAT CATGAAAAGT   300
AGTGAAAAGT GAATTTTAGT TCTGTGCTTT CTCTTCCCTT TAAGTGAACC TTTTGTTGGA   360
TCTTCATTAA AAAAATGAAA ACCTCGTCGG AATGCAACTT GGGATCACTG TCTCGGGCAA   420
GAAACGGCCT TAAAAAGGG  GAGTGATTGT GAGTGCTTGA TTTCTTAGCT GCGAACCCGC   480
TTGATTGCTG CTTGGTGGTT ATTTGGCCA  CGGGTGACCA CTCCCAGACT CAGCTGCCAG   540
GTGGTCAGTG G                                                        551
```

(2) INFORMATION FOR SEQ ID NO:15:

(i) SEQUENCE CHARACTERISTICS:
(A) LENGTH: 549 base pairs
(B) TYPE: nucleic acid
(C) STRANDEDNESS: double
(D) TOPOLOGY: linear (ii) MOLECULE TYPE: genomic DNA (vi) ORIGINAL SOURCE:
(A) ORGANISM: Brevibacterium flavum
(B) STRAIN: MJ-233

(ix) FEATURE:
(A) NAME/KEY: promoter
(B) LOCATION: 1-549
(C) IDENTIFICATION METHOD: experiment (xi) SEQUENCE DESCRIPTION:SEQ ID NO:15:

```
GATCCTCATG GATGTTGACA TCGATATGGA TTCCGACATC GAGCAGATCC TCTCCGGCGG    60
ACACGACGCA TCCCTGCTCT CCCTGGAAGC TGGCACCTGT GACGTTGCCT TCGCACACGA   120
CACCATGCTG ACCACCCTGG AGAACTCCGG CCTATCGTGC CGATCGTTCC AGGCGCTGTG   180
ATTTTTGATT TGTTGGTGGG CGATCCCAAA AACAGGCCGC TGAGAAAGTT TTCCACACTA   240
AAATAGTGTG ATTCTGTCCG AATCTGTTGT TTAGTTTTG  AAACTGCGGG ATCATGGAAA   300
GTAGTGAAAA GTGAATTTTA GTTCTGTGCT TTCTCTGCCC TTTAAGTGAA CCTTTTGTTG   360
GATCTTGCAT TAAAAAAATG AAACCTCGT  CGGGAATGCA ACTTGGGATC ACGTCTCGGG   420
CAAGAAACGT CCTTAAAAAA GGGGAGTGAT TGTGAGTGCT TGATTTCTTA GCTGCGAACC   480
CGCTGATTGC GCTGGTGGTT ATTTGGCCA  CGGTGACCAC TCCCGACTCG GCGCCGGTGG   540
TCGTGGATC                                                           549
```

(2) INFORMATION FOR SEQ ID NO:16:

(i) SEQUENCE CHARACTERISTICS:
(A) LENGTH: 2248 base pairs
(B) TYPE: nucleic acid
(C) STRANDEDNESS: double
(D) TOPOLOGY: linear (ii) MOLECULE TYPE: genomic DNA (vi) ORIGINAL SOURCE:
(A) ORGANISM: Brevibacterium flavum (B) STRAIN: MJ-233

(ix) FEATURE:
(A) NAME/KEY: promoter
(B) LOCATION: 1-2248
(C) IDENTIFICATION METHOD: experiment (xi) SEQUENCE DESCRIPTION: SEQ ID NO:16:

```
TGGGGCCGGT GGCAATGCAT CAGGGAGATT TGGATATACG GCCCACAATT CTTTGGTTCC    60
GGTCGATGGG GTAGTGAAGG TGACACGGGA TCCGATGGTG ACGTTGCTGA TCTCTGTTTC   120
TTTTACATTC GCGGTGATCT TCAGTTCGGA ATCATCAGCA ACACTCAACA GTGCGCCGGC   180
TGCTGGTTGA CCTTGGGCTG CCTGCCACGG ATGAACAATG CCTGAGTATG GGGATCGACG   240
GTGGTGTGTT GATATCATCC GAACTGGGAC GTGATCTGGT GGCGCTTAAT ATCTACTGAT   300
GCAACCTAAA GTGCATAATG CGCTTATTTT CTCCAATGGT GTTGGTGAAA ATCCGTCTC   360
GAGCCAAGTT TGCGCTTGTG TGCTATTGGG CTCATCACGG CGCCTGTGCA GCGGCTAGTC   420
TGAGTCAACT TTTCCGAGTG AATCAATGTA GATCCGCTCG GCTTTTTCTA GACCTTCAGT   480
GGTGGATGCA ACGCGTCGCT CAGTTTCCTC CAAAACGGTG TAGGACTGCA AGTTAGGCTG   540
GTCCTGGCTA GGCCACTGGA GGTTTTGGAA GCAATGATGT ACCGGCCTGC AACCTTGCTA   600
TAATGCGGGG TACACGGTTT CCACTGCGGC GCGTGCTTCT GCTGCAGGAC TGCCTCTAGG   660
TCACCTTCCA ACGCGGGCTT GAGCAAGTTC GGATTCCGAG AAGCAAATAT CTCTCTCATC   720
GAAAGCCATT TGCATCGTGA GGTTCTGCGA TCGTGGTGAA AGTCAAAGTC GGCGAGCGTC   780
AGTCGGTCAA TTTCAAGCAG CATCCAGTCG TTCAATTTCA GCAGCATCTG CTTGCTCACG   840
GGCTGCCTTG AGAGCATCCG ATTCAGCGAC CATGGTGGAA TCCAATCCGC ATCCACATCT   900
CGGTTCTTCG CTTCAAAACT GCGGATCGAT CCTGATATGC TGTGAGGACG CCGAACAGGG   960
ACGGCGCGAG TTGATCTCCG GGTCAAACCA TATCAAGAGT CCCTGGCTGT TATATGTTCT  1020
GCGCTGCGCG TGGATTCGGT CGCATGTTCA CGCGATTGTT GGATAGTTCA TCACTGTCGT  1080
TCAGGGAGAG GATCACTCAG CCACACTGTC AGTGCACACG GTACACCGAA CCGGAAGTGG  1140
GACGGACAGT ACCTGTGTAA TGGTGGTGGT TCGCGCAGCT TCAATATTCC GTTGACTCTC  1200
AAACAAAGGA ATTAAATATT AAGCGCGCCC CCCCTTAAAT TCCTTAAAAA ACTTAAATCC  1260
CAGGGAACTC CCAATCAAAA GAAACCGGGG GTCCCTTTAA CCAAATAATC TGCACCCATG  1320
ATAAAATAGC CAGGCGCATG GTATTCTGGG CCAGAAACAA GTGTATCCGC ATTAATGCCC  1380
CAAACCAGTA CCCGGGAACC TTCAAAGTCT TACAAAGCTA ACCAAATGCA GGTCGAAATC  1440
CATCCAGACA TCCGGACCAC TACTTGTTTC CCTAGAACCC CCATTCATCA CTCCGAATGG  1500
GTATGCTGAC GATAATGAGT CCTTATCGAC AGGCTGATTC TGCTGGAACC CCACATTTGG  1560
AACGTACGCG AGAACCTTCG GCGAAGCTTT TCGGTCGCGG CCGTTATCTT TTAAGAGGA   1620
GAAATTTTAG ATGAGCACGT CCACCATCAG GGTTGCCATT GCCGGAGTCG GAAATGCGCG  1680
ACCTCCCTCA TTCAGGGTGT GGAATATACC GAAATGCGGA ACCTCCGAAA TGTCCCGGTT  1740
TGCTGCACTT CAATTCGGTG ATTACCACGT TGGCGCATGA TTCGTTGCCG GTTCACGTCG  1800
ACGCCGAAAA GTAGCAGGAA TTCCCCGCAC GGGGTTACAA ACTGCATTAT CAAATGCCAG  1860
TCCGAGCCGA ATAACGGTGT TGGCCGATTT GAGGCTGGGT TCATACGGGA CATGACGGTC  1920
ACGCGGGCAT GGCGTGTCAG GGTTATGCGG AAAACCCTTT TTGAGCCCAC CTCATGGTCC  1980
AGAGCGCAAT TTCGGAAGCG AAAATTCTAC GCACAAGCGC CATCGATTGC AGTGCGCCTT  2040
TGTCAACGCT CTCCCAGTAT TCATCGCCTC CGACCCTGAG TGGGCTAAGA AGTTAACTGA  2100
GGCTGGCATC CCAATTGTTG GCGATGACAT CAAATCCCAG ATCGGTGCAA CCATCACCCA  2160
```

```
CCGTGTCCTC GCACGCCTTT TTGAAGAACG TGTCGTTCGC GTAGATCGCC ACCTGCCGGA    2220

CCATTCTGGG AACTGGACAG CAGAATAT                                      2248
```

( 2 ) INFORMATION FOR SEQ ID NO:17:

( i ) SEQUENCE CHARACTERISTICS:
    ( A ) LENGTH: 567 base pairs
    ( B ) TYPE: nucleic acid
    ( C ) STRANDEDNESS: double
    ( D ) TOPOLOGY: linear ( i i ) MOLECULE TYPE: genomic DNA ( v i ) ORIGINAL SOURCE:
    ( A ) ORGANISM: Brevibacterium flavum
    ( B ) STRAIN: MJ-233

( i x ) FEATURE:
    ( A ) NAME/KEY: promoter
    ( B ) LOCATION: 1-567
    ( C ) IDENTIFICATION METHOD: experiment ( x i ) SEQUENCE DESCRIPTION:SEQ ID NO:17:

```
GATCCAAAAA GTCGGCGCAG CTGACTGGAG CTTCTGGGAA GCCAAAGTCC GCGCCCGCGA     60

CTACGCCCTG GACGAAACCG AACTGCGCAA CTACTTCCCA CTGAACCAAG TACTCTGTGA    120

CGGCGTCTTC TTCGCTGCTA ACCGCCTCTA CGGAATCACC GTGGAACCAC GCCCTGACCT    180

GCGCGGTTAC GCCGAGGGCG TGGACGTCTG GGAAGTCCTC GATTCTGACG GCTCCGGCAT    240

CGGCCACAAG TGCGATGCGC CCCTTCCGGG TCGGCGAGGC GGTGATCTTG CGGTGTCTAC    300

CTGGGGTCGA CTGTCGAGTC GTGGTCCGCA TTGAACTTCT TTCCGTGGTG TTTATCTTTT    360

CATCACAAAC AATCACGACG GTATACCCAT CGGAGACGAT ATCGTGATCT TTCTGTTACC    420

TGCGGAAGGT AACATTAGTA TTTCAACTCG ACAGAGTCCA TCCTGGAAGC GTGTATGACG    480

ATTTCTTCAC ACATTCTTTA CAATGGCCTT TCGTGCGATA ATGCTAGGCA TGCTTCGATG    540

GACTACAGCA GGTGAATCCC ACGGATC                                       567
```

( 2 ) INFORMATION FOR SEQ ID NO:18:

( i ) SEQUENCE CHARACTERISTICS:
    ( A ) LENGTH: 1107 base pairs
    ( B ) TYPE: nucleic acid
    ( C ) STRANDEDNESS: double
    ( D ) TOPOLOGY: linear ( i i ) MOLECULE TYPE: genomic DNA ( v i ) ORIGINAL SOURCE:
    ( A ) ORGANISM: Brevibacterium flavum
    ( B ) STRAIN: MJ-233

( i x ) FEATURE:
    ( A ) NAME/KEY: promoter
    ( B ) LOCATION: 1-1107
    ( C ) IDENTIFICATION METHOD: experiment ( x i ) SEQUENCE DESCRIPTION:SEQ ID NO:18:

```
CTGGTTTTGG CGGTAGGCAA ACATGCCTTT GAGGGTAGAT GCCGGTAGGC GGAGTGCTCA     60

CGGAATCTGT GATGAGTGTG CCGCCGTCTT GGTCGATGAA ATTGTGCACG TGACGCCAGT    120

TTGCGAGGGC CTTTACGGGG GCGGTCAGAC AGACGTCGGT GAAGCGTGAA CCATTCAAAA    180

ATCCCGATAA ATCATGGCGC GCCACCCATT TAAGTCCCGC AGGAAGGCTG AAAATGGTGG    240

TGCCATCGGA GAGGCGTTCT GCCTGCGCAA TGGGGTTAAG GGGACGAAT GGCGGAGTCA     300

GACGTGTGAC AGCGCCCTTA CGGGTATGCC AATCCCAGAC CATTTCTCGG GGAAAAGGAA    360
```

```
TAAAATGGCT TGTGGTCAGA CTCACAGGGG CTTCTCCAAG TCAGTGGATT TATGAGGTCC    420

CAGTGGGTAC ACACCGGGTG TCCTACAACG ATCAATTGTC ACAGATTCGA CTGGCATGCT    480

GTACCATCTG CTTTAAGCAT TTGGTGTTT  CACTGTTGTT AACAGTGTTT CACCGTGGAG    540

CACTACCTAA AGATCATAGT CAGCATCTTG GGGTGAATGT GACACGGTAC GCTATAGTGT    600

CAGACAACAA CCAGGAAACT GGTCGTTGCA GAGTTTTTGC AAAATTGGAC ATCCTTTAAC    660

GGACCGCACA GAGAGGCGGG AAGGAGGTCA CGATGAGCGA ACGTAATAGT GCTGTACTAG    720

AACTCCTCAA TGAGGACGAC GTCAGCCGTA CCATCGCACG CATCGCGCAC CAGATTATTG    780

AGAAAACCGC GCTTGATTCC AAATACGCGG ATCGGGTCAT GTTGTTAGGC ATTCCTTCAG    840

GTGGAGTCCC GCTGGCCCGA AGGCTTGCTG AAAAGATCGA AGAATTTTCC GGCGTTTCGG    900

TAGATACCGG CGCTGTTGAT ATCACCTTGT ACAGGGATGA TCTTCGAAAC AAACCGCACC    960

GCGCACTGCA GCCCACCTCT ATTCCGGCAG GTGGTATCGA TAACACCACC GTGATTTTGG   1020

TGGATGATGT GCTGTTTTCC GGTCGTACTA TNCGCGCTGC ACTTGATGCA TTGCGCGACG   1080

TTGGACGCCC AAACTATATC CAATTAG                                        1107
```

( 2 ) INFORMATION FOR SEQ ID NO:19:

( i ) SEQUENCE CHARACTERISTICS:
        ( A ) LENGTH: 2115 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-2115
        ( C ) IDENTIFICATION METHOD: experiment ( x i ) SEQUENCE DESCRIPTION: SEQ ID NO:19:

```
GGATCCGGTA ACCGTTTTTA TCAGGCTCTG GGAGGCAGAA TAAATGATCA TATCGTCAAT     60

TATTACCTCC ACGGGAGAG  CCTGAGCAAA CTGGCCTCAG GCATTTAAGA AGCACACGGT    120

CACACTGCTT CCGGTAGTCA ATAAACCGGT AAACCAGCAA TAGACATAAG CGGCTATTTA    180

ACGACCCTGC CCTGAACCGA CGACCGGGTC GAATTGCTT  TCGATATCTG CCATTCATCC    240

GCTTATTATC ACTTATTCAG GCGTAGAACC AGGCGTTTAA GGGCACCAAT AACTGCCTTA    300

AAAAAATTAC GCCCGCCCTG CCACTCATCG CAGTACTGTT GTAATTCATT AAGCATTCTG    360

CCGACATGGG AGGCCATCAC AAACGGGCAT GATGAACCTG AATCGCCAGC GGGCATCAGC    420

ACTTGGTCGC CTTGCGTATA AATATTTGCC CCTGGTGGAA AACGGGGGCG AAGAGGTTGT    480

CCCATATTTG GCCACGGTTT AAATCAAAAT TGGTGGAACT CACCCTGGGT TTGGCTAGCG    540

ATCCGGGTTG ACATCTGCAG GCGGGAAATT GAAAAGGCCG GATAAACTG  GTGCCTATTT    600

CCTTTAACGG TCTTTAAAAA AGGCCCGTAA TACCCAACTG AAACGGTCTG GTTATAGTAA    660

CATTGGACAA CTGGACTGGA AATGCCCTCC AAATGGTCCT TTACGATGCC CAATTGGGGA    720

TATATCCAAC GGTGGTATAA CCCAGTGATT TTTTTCCTC  CCATTTTTAG CTTCCTTTAG    780

CTCCTGAAAA TCTCGATAAC TCAAAAAAT  ACGCCCGGTA GTGATCTTAT TTCATTATGG    840

TGAAAGTTGG AACCTCTTAC GTGCCGATCA ACGTCTCATT TTCGCCAAAA GTTGGCCCAG    900

GGCTTCCCGG TATCAACAGG GACACCAGGA TTATTTATTC TGCGAAGTGA TCTTCCGTCA    960
```

-continued

```
CAGGTATTTA TTCGGCGCAA AGTGCGTCGG GTGATGCTGC CAACTTACTG ATTTAGTGTA 1020
TGATGGTGTT TTTGAGGTGC TCCAGTGGCT TCTGTTTCTA TCAGCTGTCC CTCCTGTTCA 1080
GCTATTGACG GGGTGGTGCG TAACGGAAAA GCACCGCCGG ACATCACCGG ATCTCAAGAA 1140
GACCTTTGAA CTGTTCAACG GATCCCCAGG GGCAGGCGGT ACACCGCGCC CTCGGACGTA 1200
TCGGAGTTTC TGGCGTTTCC GATGTCCGTC AGGGAAAGCG CTTCGAGCTT GAGGTAGATG 1260
ATTCCGTCAC CGAAGCTGAC CTAAAGAAAA TTGCTGAAAC CCTCCTCGCA AACACCGTCA 1320
TCGAAGACTT CGATGTGGTG GGAGTTGAGG TCGCGAAGTG AGCGCCAAAA TCGGTGTCAT 1380
TACCTTCCCA GGCACCCTTG ACGATGTAGA TGCAGCACGC GCTGTTCGCA TCGCAGGTGC 1440
AGAAGTAATC AGCCTGTGGC ACGCTGACGA GGATCTCAAG GGCGTCGACG CAGTTGTCGT 1500
TCCCGGTGGA TTCCTCCTAC GGCGATTACC TGCGCACCGG TGCAATCTCT GCACTGGCGC 1560
CAGTAATGCA GTCCGTGATT GAGCAGGCCG GTAAGGGTAT GCCAGTCTTG GGCATTTGCA 1620
ACGGCTTCCA GATCCTCACC GANGCACGCC TGCTTCCAGG CGCGCTGACC CGCAACAAGG 1680
GTCTGCACTT TCACTGTGTA GACGCACACC TCGTTGTAGA GAACAACACC ACTGCATGGA 1740
CCAACACTTT GGAAAAGGGG CAGCAGATCC TTATTCCTGC AAAGCACGGT GAAGGTCGCT 1800
TCCAGGCAGA CGGCAGAGAC CATTCGCCCA GCTTTGAGGG TGAAGGCCGC GTGGTGTTCC 1860
GTTACAACGA TAACTTCAAC GGTTTCCGTA GACCTACCAA GCCGGTATCA CTAATGAAAC 1920
TGGTCGCATC GTCGGTCTCA TGCCGCACCC GGAACATGCC GTCGAAAAGC TAACCGGCCC 1980
ATCTATTGAT GGCCTGGAGC TGTTCCTGTC CGCCGTTGGC ACCATCGCGG CTTAAGAGGA 2040
GTCAAAATAT GAGCACTTTT GTCAATGACA CCGTCGAGAG CAATCAAGAC CCCTGAGATC 2100
AATTCTGGGA TCTGA                                                  2115
```

( 2 ) INFORMATION FOR SEQ ID NO:20:

( i ) SEQUENCE CHARACTERISTICS:
        ( A ) LENGTH: 2213 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium flavum
        ( B ) STRAIN: MJ-233

( i x ) FEATURE:
        ( A ) NAME/KEY: promoter
        ( B ) LOCATION: 1-2213
        ( C ) IDENTIFICATION METHOD: experiment ( x i ) SEQUENCE DESCRIPTION: SEQ ID NO:20:

```
ATATTCTGCT GTCCAGTTCC CAGAATGGTC CGGCAGGTGG CGATCTACGC GAACGACACG  60
TTCTTCAAAA AGGCGTGCGA GGACACGGTG GGTGATGGTT GCACCGATCT GGGATTTGAT 120
GTCATCGCCA ACAATTGGGA TGCCAGCCTC AGTTAACTTC TTAGCCCACT CAGGGTCGGA 180
GGCGATGAAT ACTGGGAGAG CGTTGACAAA GGCGCACTGC AATCGATGGC GCTTGTGCGT 240
AGAATTTTCG CTTCCGAAAT TGCGCTCTGG ACCATGAGGT GGGCTCAAAA AGGGTTTTCC 300
GCATAACCCT GACACGCCAT GCCCGCGTGA CCGTCATGTC CGTATGAAC  CCAGCCTCAA 360
ATCGGCCAAC ACCGTTATTC GGCTCGGACT GGCATTTGAT AATGCAGTTT GTAACCCCGT 420
GCGGGGAATT CCTGCTACTT TTCGGCGTCG ACGTGAACCG GCAACGAATC ATGCGCCAAC 480
GTGGTAATCA CCGAATTGAA GTGCAGCAAA CCGGGACATT TCGGAGGTTC CGCATTTCGG 540
```

-continued

```
TATATTCCAC ACCCTGAATG AGGGAGGTCG CGCATTTCCG ACTCCGGCAA TGGCAACCCT    600
GATGGTGGAC GTGCTCATCT AAAATTTCTC CTCTTAAAAA GATAACGGCC GCGACCGAAA    660
AGCTTCGCCG AAGGTTCTCG CGTACGTTCC AAATGTGGGG TTCCAGCAGA ATCAGCCTGT    720
CGATAAGGAC TCATTATCGT CAGCATACCC ATTCGGAGTG ATGAATGGGG GTTCTAGGGA    780
AACAAGTAGT GGTCCGGATG TCTGGATGGA TTTCGACCTG CATTTGGTTA GCTTTGTAAG    840
ACTTTGAAGG TTCCCGGGTA CTGGTTTGGG GCATTAATGC GGATACACTT GTTTCTGGCC    900
CAGAATACCA TGCGCCTGGC TATTTATCA TGGGTGCAGA TTATTTGGTT AAAGGGACCC    960
CCGGTTTCTT TTGATTGGGA GTTCCCTGGG ATTTAAGTTT TTAAGGAAT TTAAGGGGGG    1020
GCGCGCTTAA TATTTAATTC CTTTGTTTGA GAGTCAACGG AATATTGAAG CTGCGCGAAC    1080
CACCACCATT ACACAGGTAC TGTCCGTCCC ACTTCCGGTT CGGTGTACCG TGTGCACTGA    1140
CAGTGTGGCT GAGTGATCCT CTCCCTGAAC GACAGTGATG AACTATCCAA CAATCGCGTG    1200
AACATGCGAC CGAATCCACG CGCAGCGCAG AACATATAAC AGCCAGGGAC TCTTGATATG    1260
GTTGACCCG GAGATCAACT CGCGCCGTCC CTGTTCGGCG TCCTCACAGC ATATCAGGAT    1320
CGATCCGCAG TTTTGAAGCG AAGAACCGAG ATGTGGATGC GGATTGGATT CCACCATGGT    1380
CGCTGAATCG GATGCTCTCA AGGCAGCCCG TGAGCAAGCA GATGCTGCTG AAATTGAACG    1440
ACTGGATGCT GCTTGAAATT GACCGACTGA CGCTCGCCGA CTTTGACTTT CACCACGATC    1500
GCAGAACCTC ACGATGCAAA TGGCTTTCGA TGAGAGAGAT ATTTGCTTCT CGGAATCCGA    1560
ACTTGCTCAA GCCCGCGTTG GAAGGTGACC TAGAGGCAGT CCTGCAGCAG AAGCACGCGC    1620
CGCAGTGGAA ACCGTGTACC CCGCATTATA GCAAGGTTGC AGGCCGGTAC ATCATTGCTT    1680
CCAAAACCTC CAGTGGCCTA GCCAGGACCA GCCTAACTTG CAGTCCTACA CCGTTTTGGA    1740
GGAAACTGAG CGACGCGTTG CATCCACCAC TGAAGGTCTA GAAAAGCCG AGCGGATCTA    1800
CATTGATTCA CTCGGAAAAG TTGACTCAGA CTAGCCGCTG CACAGGCGCC GTGATGAGCC    1860
CAATAGCACA CAAGCGCAAA CTTGGCTCGA GACGGGATTT TCACCAACAC CATTGGAGAA    1920
AATAAGCGCA TTATGCACTT TAGGTTGCAT CAGTAGATAT TAAGCGCCAC CAGATCACGT    1980
CCCAGTTCGG ATGATATCAA CACACCACCG TCGATCCCCA TACTCAGGCA TTGTTCATCC    2040
GTGGCAGGCA GCCCAAGGTC AACCAGCAGC CGGCGCACTG TTGAGTGTTG CTGATGATTC    2100
CGAACTGAAG ATCACCGCGA ATGTAAAAGA AACAGAGATC AGCAACGTCA CCATCGGATC    2160
CCGTGTCACC TTCACTACCC CATCGACCGG AACCAAAGAA TTGTGGGCCG TAT           2213
```

( 2 ) INFORMATION FOR SEQ ID NO:21:

( i ) SEQUENCE CHARACTERISTICS:
      ( A ) LENGTH: 61 base pairs
      ( B ) TYPE: nucleic acid
      ( C ) STRANDEDNESS: double
      ( D ) TOPOLOGY: linear ( i i ) MOLECULE TYPE: Other nucleic acid
      ( A ) DESCRIPTION: Synthetic ( i i i ) HYPOTHETICAL: NO ( i v ) ANTI-SENSE: NO ( x i ) SEQUENCE DESCRIPTION: SEQ ID NO:21:

```
AATTCTCGCG ATAATTAATT AATAGCCCGC CTAATGAGCG GGCTTTTTTT TGATATCAAT    60
T                                                                    61
```

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic ( i i i ) HYPOTHETICAL: NO ( i v ) ANTI-SENSE: NO ( x i ) SEQUENCE DESCRIPTION: SEQ ID NO:22:

GATCAGATCC CAGAATTGAT                20

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic ( i i i ) HYPOTHETICAL: NO ( i v ) ANTI-SENSE: NO ( x i ) SEQUENCE DESCRIPTION: SEQ ID NO:23:

TGAGCGGGCT TTTTTTGAT                 20

( 2 ) INFORMATION FOR SEQ ID NO:24:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: Other nucleic acid
        ( A ) DESCRIPTION: Synthetic ( i i i ) HYPOTHETICAL: NO ( i v ) ANTI-SENSE: NO ( x i ) SEQUENCE DESCRIPTION: SEQ ID NO:24:

GATCTCAAGA AGATCCTTTG ATCTTTTCTA CGGATCCCAG        40

PROMOTER DNA FRAGMENT FROM CORYNEFORM BACTERIA

CROSS REFERENCE TO RELATED APPLICATION

The present application is a continuation in part of U.S. application Ser. No. 08/076,091, filed Jun. 15, 1993, which is a continuation in part of U.S. application Ser. No. 07/709,151, filed Jun. 3, 1991 (abandoned Aug. 4, 1993), the disclosure of which are hereby incorporated by reference.

FIELD OF THE INVENTION

The present invention relates to a promoter DNA fragment originating from chromosomal DNA of a coryneform bacterium.

BACKGROUND OF THE INVENTION

Coryneform bacteria are Gram-positive bacteria widely used for industrial-scale production of a variety of products including amino acids, such as glutamic acid and aspartic acid; and purine nucleotides, such as inosinic acid, etc. However, compared with *Escherichia coli*, coryneform bacteria have not been extensively bred by using recombinant DNA techniques. To fully utilize the recombinant DNA techniques for breeding of coryneform bacteria, a vector must be developed useful for industrial-scale gene manipulation in coryneform bacteria. More particularly, a promoter DNA fragment of such a vector must be developed, i.e., a promoter having a strong gene-expression function or a promoter whose gene-expression function is controllable.

Improvement of promoter function in coryneform bacteria has been reported by using promoters originating from *Escherichia coli*. The Journal of Biotechnology, 5, 305, (1987) and Gene, 102, 93, (1991) state that a tac promoter (Gene, 20, 231 (1982)) obtained by fusing a protein of trp promoter and lac promoter both originating from *Escherichia coli* achieved a greater constitutive promoter strength in coryneform bacteria than any other promoter examined so far.

As far as the inventors know, no promoter has since been developed that achieves a greater promoter strength in coryneform bacteria than the tac promoter.

A method for controlling the expression of a gene of interest in a coryneform bacterium is described in Bio/Technology, 6, 428, (1988), in which a controllable promoter originating from *Escherichia coli* is incorporated into a coryneform bacterium without modifying the promoter. However, this gene-expression control method fails to achieve a level of expression of a gene of interest in the host coryneform bacterium comparable to the level that is achieved by the same promoter in *Escherichia coli*.

In developing a system for manipulating the expression of cloned genes in coryneform bacteria for which no such system exists, it is desirable to begin by isolating a variety of different promoter elements with different functional properties. Functional properties of interest may indicate whether a promoter is one which is repressed under some conditions, but induced under other culture conditions. Use of controllable promoters allows the expression of cloned genes to be induced or repressed in a controlled manner.

SUMMARY OF THE INVENTION

Accordingly, an object of the present invention is to obtain a promoter DNA fragment which shows the expression of a gene of interest in coryneform bacteria at a high rate. More particularly, an object of the present invention is to obtain from the chromosome of a coryneform bacterium a promoter DNA fragment having greater promoter strength than the above-described *E. coli* tac promoter, and to obtain from the chromosome of a coryneform bacterium a promoter DNA fragment which is useful for controlling the expression of a gene of interest in a coryneform bacterium.

The inventors of the present invention have found that such a promoter DNA fragment can be obtained from coryneform bacteria by using a novel promoter probe shuttle vector constructed by the inventors. The promoter probe shuttle vector comprises:

a) a replication origin DNA region that is functional in *Escherichia coli*, b) a replication origin DNA region that is functional in coryneform bacteria, c) a DNA region including a selectable marker gene, d) a DNA region including a reporter gene, the DNA region including a gene which lacks its own promoter region and differs from the selectable marker gene of C) in phenotype, and e) a Transcription terminator located in the upstream from the DNA region d) including the reporter gene.

Based on the above finding, the invention provides:

(1) a promoter DNA fragment which is obtained from a chromosome of a coryneform bacterium and is functional in coryneform bacteria, the promoter DNA fragment having a greater promoter strength in coryneform bacteria than the tac promoter, and (2) a controllable promoter DNA fragment which is obtained from a chromosome of a coryneform bacterium and is functional in coryneform bacteria, wherein the promoter function of the controllable promoter DNA fragment is controllable by replacing at lease one substance which is contained in the culture medium for the host coryneform bacterium and is assimilable by the host coryneform bacterium, with at least one other substance which is assimilable by that the host coryneform bacterium.

DESCRIPTION OF THE PREFERRED EMBODIMENTS

Figure 1:
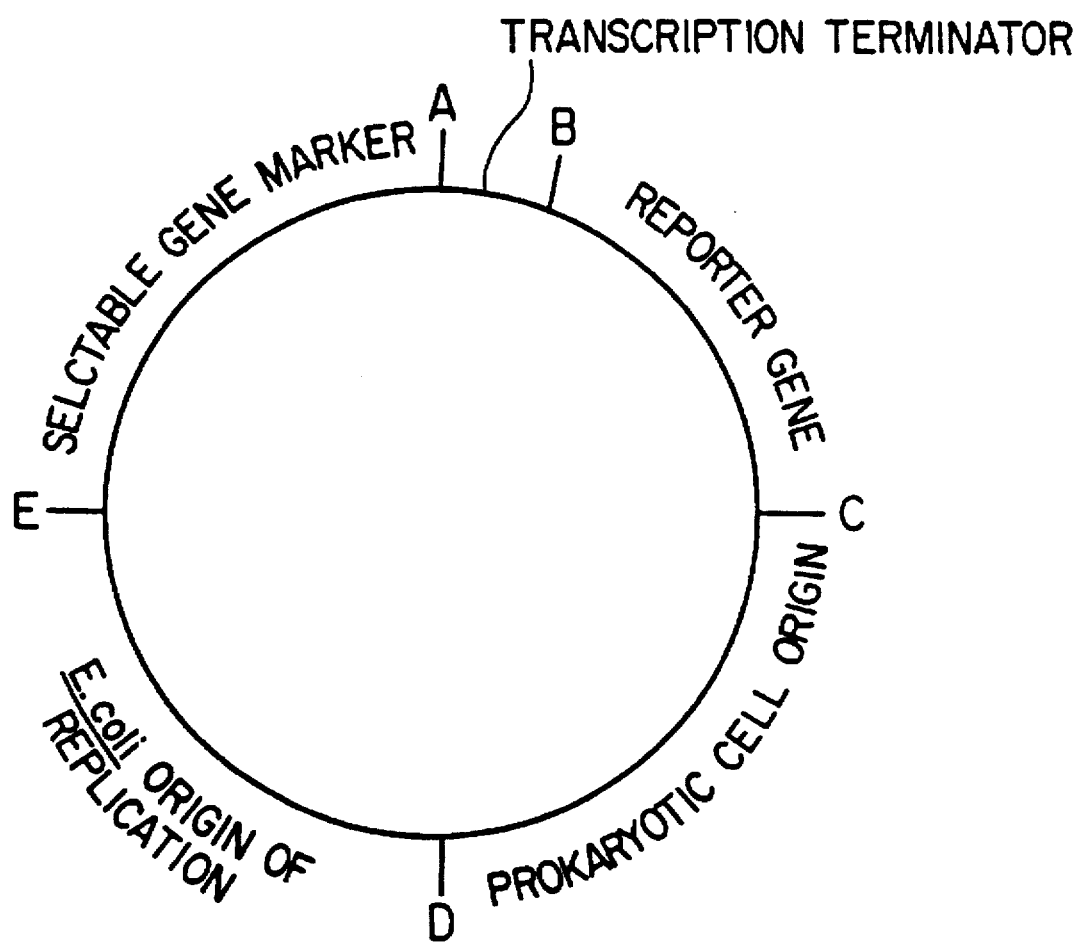
FIG. 1 shows the promoter probe shuttle vector useful for detecting a promoter DNA fragment in coryneform bacteria according to the present invention.

The present invention will be described in detail hereinafter.

First, several terms used in this specification will be defined. The term "promoter" means a DNA region to which an RNA polymerase specifically binds so as to initiate the transcription of the gene. The term "tac promoter" means a promoter obtained by fusing a sequence obtained from −35 region of a tryptophan operon promoter of *Escherichia coli* and a sequence obtained from −10 region of a lactose operon promoter of *Escherichia coli*. The term "promoter DNA fragment" means a synthetic DNA fragment or a DNA fragment obtained from a naturally occurring chromosomal DNA, either of which has the function to initiate the transcription of a gene, that is, a gene transcription function, and includes a promoter as defined above. The term "promoter DNA fragment having a greater promoter strength than a tac promoter" means an above-defined promoter DNA fragment which has a stronger gene-transcription initiating capability than the tac promoter. The term "controllable promoter DNA fragment" means a promoter DNA fragment whose function to initiate the transcription of a gene can be controlled, that is, can be induced when the function has been repressed, or repressed when the function has been induced, by replacing at least one substance that is contained in the culture medium for a host coryneform bacterium having the promoter DNA fragment and useful for the host bacterium, with at least one other substance. The term "coryneform bacteria" means a group of microorganisms defined in Bargeys Manual of Determinative Bacteriology, 8, 599, (1974), that is, rod-shaped bacteria which are aerobic, Gram positive, non-acid-fast and non-sporogenous. According to the present invention, particularly preferred coryneform bacteria as the gene sources or host microorganisms of promoter DNA are the following coryneform bacteria:

*Brevibacterium ammoniagenes* ATCC 6871
*Brevibacterium divaricatum* ATCC 14020
*Brevibacterium saccharolyticum* ATCC 14066
*Brevibacterium immariophilium* ATCC 14068
*Brevibacterium lactofermentum* ATCC 13869
*Brevibacterium roseum* ATCC 13825
*Brevibacterium linens* ATCC 9174
*Brevibacterium flavum* ATCC 13826
*Brevibacterium flavum* MJ-233 (FERM BP-1497)
*Brevibacterium stationis* IFO 12144 (FERM BP-2515)
*Brevibacterium thiogenitalis* ATCC 19240
*Corynebacterium acetoacidophilum* ATCC 13870
*Corynebacterium acetoglutamicum* ATCC 15806
*Corynebacterium callunae* ATCC 15991
*Corynebacterium glutamicum* ATCC 13032, ATCC 13060
*Corynebacterium lilium* ATCC 15990
*Corynebacterium melassecola* ATCC 17965

*Brevibacterium flavum* MJ-233 and *Brevibacterium stationis* IFO 12144 listed above have been deposited under deposit Nos. FERM BP-1497 and FERM BP-2515, respectively, at Fermentation Research Institute, Agency of Industrial Science and Technology (now National institute of Bioscience and Human-Technology), 1-3, Higashi 1-chome, Tsukuba-shi, Ibaraki-ken 305, Japan, under the Budapest Treaty. The other coryneform bacteria having ATCC numbers are described in American Type Culture Collection, Catalogue of Bacteria and Phages. All the above-listed bacteria are publicly available.

These coryneform bacteria can be incubated in known culture media widely used for coryneform bacteria, and can be recovered from the cultures.

A promoter DNA fragment according to the present invention can be obtained from naturally occurring chromosomes of micro-organisms, though such a promoter DNA fragment may be synthesized after its nucleotide sequence has been determined. *Brevibacterium flavum* MJ-233 (FERM BP-1497) is preferred as a source microorganism for the promoter DNA fragment.

To isolate a promoter DNA fragment from any of the above coryneform bacteria, chromosomal DNA is extracted from the bacterium by, for example, a method described in Biochimica et Biophysica Acta., 72, 619, (1963), and then digested into relatively short DNA fragments by using suitable restriction enzymes, preferably, one or more restriction enzymes which recognize 4-base sequences, for example, AluI, HaeIII, AccII or AfaI.

A promoter DNA fragment can be isolated from the restriction fragments of the chromosomal DNA by using promoter probe shuttle vectors.

Promoter Probe Shuttle Vector

A preferred promoter probe shuttle vector is the novel vector constructed by the inventors, the vector comprising:

a) a replication origin DNA region functional in *Escherichia coli*, b) a replication origin DNA region functional in coryneform bacteria, c) a DNA region including a selectable marker gene, d) a DNA region including a reporter gene, and e) a transcription terminator located in the upstream from the DNA region d) including a reporter gene.

The DNA region functional in *Escherichia coli* a) (hereinafter, referred to as "region a") is not particularly restricted as long as it controls self-replication of the plasmid in *Escherichia coli*. Region a may be attained by using a DNA fragment obtained from, for example, the plasmid pACYC184 (a product of Nippon Gene Co., Ltd.), the plasmid pBR322 (a product of TAKARA SHUZO Co., Ltd.).

The DNA region functional in coryneform bacteria b) (hereinafter, referred to as "region b") is not particularly restricted as long as it controls self-replication of the plasmid in coryneform bacteria. Region b may be obtained by using, for example, the plasmid pCRY3 (a plasmid possessed by Brevibacterium flavum MJ233 GE102, described in U.S. Pat. No. 5,185,262), the plasmid pCRY2 (a plasmid possessed by Brevibacterium flavum MJ233 GE101, described in U.S. Pat. No. 5,185,262), the plasmid pAN330 (described in Japanese Patent Application Laid-open No. 58-67679 (1983)), or the plasmid pHM1519 (described in Japanese Patent Application Laid-open No. 58-77895 (1983) ).

The above-mentioned *Brevibacterium flavum* MJ233 GE101 and *Brevibacterium flavum* MJ233 GE102 have been deposited under deposit Nos. FERN BP-2512 and FERM BP-2513, respectively, at Fermentation Research Institute, Agency of Industrial Science and Technology (now National institute of Bioscience and Human-Technology), under the Budapest Treaty.

The DNA region c) including a selectable marker gene (hereinafter, referred to as "region c" or "the marker gene") is not particularly restricted as long as it can be used as a marker of the plasmid and includes a gene different in phenotype from the gene present in the DNA region d) including a reporter gene. Region c may be obtained by, for example: a 1,300 bp DNA fragment which is obtained by digesting, with restriction enzyme BamHI, the plasmid pJCM1 that has been constructed by inserting approximately −3.0 Kb BamHI-PvuII fragment of Transposon 9 (Nature, 293, 309–311 (1981)) including a chloramphenicol resistance gene into BamHI and PvuII sites of the plasmid pBR322 and which includes a chloramphenicol resistance gene; a 787 bp DNA fragment which is obtained by digesting the plasmid pCM7 (a product of Pharmacia Co., Ltd.)

with restriction enzyme HindIII and includes a Chloramphenicol resistance gene; Chloramphenicol Acetyltransferase GenBlock having a size of 792 bp (a product of Pharmacia Co., Ltd.); or a 1,426 bp DNA fragment which is obtained by digesting the plasmid pBR322 (a product of Takara Shuzo Co., Ltd.) with restriction enzymes EcoRI and AvaI and includes a tetracycline resistance gene.

The DNA region d) including a reporter gene hereinafter, referred to as "region d" or "the reporter gene") is not particularly restricted as long as it can be used as a marker of the plasmid and includes a gene which lacks its own promoter and differs from the marker gene present in region c. Region d may be constituted by, for example: an approximately −1.6 Kb DNA fragment which includes a kanamycin resistance gene and is obtained by digesting, with restriction enzymes BglII and BamHI, the plasmid pKPG13 that has been constructed by inserting an approximately −5.9 Kb BamHI-SalI fragment of Transposon 5 (described in Molecular and General Genetics, 177, 65 (1979)) including NPTII (a kanamycin resistance gene) into BamHI and SalI sites oil the plasmid pBR322; a 1,494 bp DNA fragment which is obtained by digesting the plasmid pNEO (a product of Pharmacia Co., Ltd.) with restriction enzymes HindIII and BamHI and includes a kanamycin resistance gene; Kanamycin Resistance GenBlock having a size of 1,282 bp (a product of Pharmacia Co., Ltd.); or a 3,117 bp or approximately −3.3 Kb DNA fragment which is obtained by digesting the plasmid pMC1871 (a product of Pharmacia Co., Ltd.) or pSGMU32 (a product of Pharmacia Co., Ltd.) with restriction enzyme BamHI or restriction enzymes SacI and SalI, respectively, and which includes a β-galactosidase gene.

The transcription terminator e) located in the upstream from the reporter gene (region d) (hereinafter, referred to as "region e" or "the transcription terminator") may be a trpA terminator of a tryptophan operon of *Escherichia coli* which includes the following nucleotide sequence (SEQ ID NO:21):

5'AATTCTCGCGATAATTAATTAATAGC-
   C  G  C  C  T  A  A  T  -
GAGCGGGCTTTTTTTTTGATATCAATT3'
3'TTAAGAGCGCTATTAATTAAT-
TATCGGGCGGATTACTCGC-
CCGAAAAAAAACTATAGTTAA5'

Such a trpA terminator may be chemically synthesized by a DNA synthesizer.

Next described will be a method for constructing a promoter probe shuttle vector comprising the above-described five DNA regions a to e, which vector is used to obtain a promoter DNA fragment according to the present invention.

First, region a and region c including a selectable marker gene (this marker gene will be used as a marker in the process of constructing a promoter probe shuttle vector) are ligated with a DNA ligase to construct a plasmid which includes a marker gene and is capable of replication in *Escherichia coli*. Then, the plasmid having regions a and c is cleaved with a suitable restriction enzyme, followed by coupling the transcription terminator (region e) to one of the ends thereof and then ligating the reporter gene (region d) to the downstream end of the transcription terminator. Finally, the thus-obtained plasmid which includes the transcription terminator (region e), the reporter gene (region d) located in the downstream end of the transcription terminator and the marker gene (region c), and which is capable of replication in *Escherichia coli* is cleaved with a suitable restriction enzyme, followed by ligating region b to the cleavage with a DNA ligase. A promoter probe shuttle vector is thus constructed.

Examples of the promoter probe shuttle vector thus constructed are:

a plasmid pPROBE17 consisting essentially of a) a plasmid replication origin region that is functional in *Escherichia coli* (a DNA fragment obtained by coupling a promoter to a 1.1 Kb DNA fragment obtained by digesting the plasmid pBR322 with restriction enzymes BstYI and PvuII), b) a plasmid replication origin region that is functional in coryneform bacteria (4.0 Kb DNA fragment obtained by digesting the plasmid pCRY3 with restriction enzyme XhoI), c) a chloramphenicol resistance gene(a 1.3 Kb DNA fragment obtained by digesting the plasmid pJCM1 with restriction enzyme BamHI) a kanamycin resistance gene lacking its own promoter (a 3.3 Kb DNA fragment obtained by digesting the plasmid pKPG13 with restriction enzymes BglII and BamHI), and e) a transcription terminator (a trpA terminator, that is, the above-described 61 bp synthetic DNA fragment) located in the upstream from the kanamycin resistance gate; and a plasmid p13Bgal consisting essentially of a) a plasmid replication origin region that is functional in *Escherichia coli* (a DNA fragment the same as in the above-described plasmid pPROBE17), b) a plasmid replication origin region that is functional in coryneform bacteria (a DNA fragment the same as in the above-described plasmid pPROBE17), c) a chloramphenicol resistance gene (a DNA fragment the same as in the above-described plasmid pPROBE17), d) a β-galactosidase gene lacking its own promoter (a 3.3 Kb DNA fragment obtained by digesting the plasmid pSGMU22 with restriction enzymes SacI and SalI), and e) a transcription terminator (a DNA fragment the same as in the above-described plasmid pPROBE17) located in the upstream from the kanamycin resistance gene.

The construction of the plasmid pPROBE17 shown in FIGS. 2 and 3 will be described in detail in Example 1. The restriction map of the plasmid p17Bgal is shown in FIG. 4.

Set forth below is a description of a method for isolating a promoter DNA fragment according to the present invention from chromosomal DNA of coryneform bacteria cells by using promoter probe shuttle vectors as described above.

Promoter DNA Fragment Isolation Method

Promoter probe shuttle vectors as described above are introduced into coryneform bacteria cells by a known transformation method, for example, the electroporation method (Agricultural and Biological Chemistry, 54, 443, (1990)). The transformants are cultured in a suitable medium to confirm that the reporter gene (region d) is not expressed (the gene remains unexpressed because the reporter gene lacks its own promoter). If the reporter gene is an antibiotic resistance gene, whether the reporter gene is expressed and how strongly it is expressed can be easily determined by plating the transformants on selection media containing the antibiotic concerned and examining the antibiotic sensitivity of the transformants. Determination of the expression of the reporter gene and the strength of its expression can also be performed by culturing the transformants in ordinary media and investigating the cultures for the expression product of the reporter gene on the basis of characteristics or properties of the product. For example, if the reporter gene is a β-galactosidase gate, the transformants are plated on selection media containing 5-bromo-4-chloro-3-indolyl-β-D-galactoside (X-gal), that is, a substrate of β-galactosidase, and measuring the color tone of the colonies of transformants, that is, colonies which exhibit blue color as a result of decomposition of the X-gal by the action of β-galactosidase expressed.

The promoter probe shuttle vectors whose reporter gene expression has been confirmed to be inactive in the coryneform bacterium are cleaved by a suitable restriction enzyme which recognizes a unique site between the reporter gene (region d) and the transcription terminator (region e). The resultant DNA fragments are ligated with a DNA ligase to DNA fragments obtained by digesting chromosomal DNA of the coryneform bacterium with a 4-base-sequence-recognizing restriction enzyme. The thus-constructed plasmids are introduced into coryneform bacteria cells by the electroporation method or the like.

The thus-obtained transformants are cultured, and the reporter gene expression is examined by a method described above. The transformants whose reporter gene expression has been confirmed to be active are recovered, thus obtaining coryneform bacteria cells which have been transformed with promoter probe shuttle vectors containing promoter DNA fragments. A promoter DNA fragment according to the present invention can be obtained from these coryneform bacteria cells capable of the expression of reporter gene by a method described below.

Promoter DNA Fragment of the Invention Having Greater Promoter Strength Than the tac Promoter First, a method will be described for obtaining a promoter DNA fragment of the invention having a greater promoter strength than the tac promoter.

The tac promoter, serving as a standard for promoter probe strength comparison, is inserted into a promoter probe shuttle vector at a site between the reporter gene (region d) and the transcription terminator (region e) by the above-described method. The resultant plasmid is introduced into coryneform bacteria cells by the electroporation method, followed by examining the reporter gene expression strength by a method as described above. The tac promoter used in this process may be, for example, a 96 bp DNA fragment obtained by digesting the plasmid pDR540 (Pharmacia Co., Ltd.) with restriction enzymes HindIII and BamHI, or a DNA fragment accordingly synthesized by a DNA synthesizer.

With reference to the reporter gene expression strength in the coryneform bacteria cells transformed with the above-described promoter probe shuttle vector containing the tac promoter, the reporter gene expression strengths of coryneform bacteria cells transformed with promoter probe shuttle vectors containing DNA fragments obtained from chromosomal DNA of the coryneform bacterium are examined, and the cells exhibiting greater expression strength are selected. Thus, transformants containing promoters having greater promoter strength than the tac promoter are obtained.

To determine whether the enhancement in the reporter gene expression in each of the transformants is caused by the promoter contained in the promoter probe shuttle vector or a mutation in the chromosome of the host cell, plasmid DNA is extracted from each transformant and introduced again into coryneform bacteria cells, followed by an examination of the reporter gene expression strength of the transformed cells. The transformants whose reporter gene expression enhancement has been confirmed to be caused by the promoter are recovered.

Examples of the transformants thus obtained are: the below-listed twelve strains of Brevibacterium flavum MJ-233 which have been transformed with plasmids obtained by inserting AluI-HaeIII restriction fragments of chromosomal DNA of Brevibacterium flavum MJ-233 (FERM BP-1497) into the above-described promotor probe shuttle vectors pPROBE17 at the restriction enzyme EcoRV recognition site, and which are resistant to kanamycin concentration of 500 μg/ml or greater, that is, able to grow on a medium containing 500 μg/ml or more of kanamycin.

These twelve transformants and the plasmids contained therein are named as follows:

| No | Bacteria strain | | | Plasmid | |
|---|---|---|---|---|---|
| (1) | Brevibacterium flavum | MJ233 | Km5001 | pPROBE17 | Km5001 |
| (2) | Brevibacterium flavum | MJ233 | Km5002 | pPROBE17 | Km5002 |
| (3) | Brevibacterium flavum | MJ233 | Km5003 | pPROBE17 | Km5003 |
| (4) | Brevibacterium flavum | MJ233 | Km5004 | pPROBE17 | Km5004 |
| (5) | Brevibacterium flavum | MJ233 | Km5005 | pPROBE17 | Km5005 |
| (6) | Brevibacterium flavum | MJ233 | Km5006 | pPROBE17 | Km5006 |
| (7) | Brevibacterium flavum | MJ233 | Km5007 | pPROBE17 | Km5007 |
| (8) | Brevibacterium flavum | MJ233 | Km5008 | pPROBE17 | Km5008 |
| (9) | Brevibacterium flavum | MJ233 | Km5009 | pPROBE17 | Km5009 |
| (10) | Brevibacterium flavum | MJ233 | Km5010 | pPROBE17 | Km5010 |
| (11) | Brevibacterium flavum | MJ233 | Km5011 | pPROBE17 | Km5011 |
| (12) | Brevibacterium flavum | MJ233 | Km5012 | pPROBE17 | Km5012 |

The kanamycin resistances of the transformants are summarized in Table 1. Brevibactrerium flavum MJ-233 transformed with a plasmid obtained by inserting the tac promoter to the promoter probe shuttle vector pPROBE17 at the EcoRV site was not resistant to even 500 μg/ml of kanamycin, that is, was not able to grown on a medium containing 500 μg/ml of kanamycin.

TABLE 1

| Kanamycin concentration in medium (μg/ml) | 500 | 750 | 1000 | 1500 |
|---|---|---|---|---|
| Nos. of transformants | 5 | 4 | 1 | 2 |

Determination of the Size of Nucleotide Sequence of Promoter DNA Fragment of the Invention Having Greater Promoter Strength Than tac Promoter A promoter DNA fragment according to the present invention having greater promoter strength than the tac promoter is obtained from a transformant isolated as described above. The size and nucleotide sequence of such a promoter DNA fragment can be determined as follows.

First, primer DNA fragments are chemically synthesized corresponding to nucleotide sequences of a plasmid probe shuttle vector present in the upstream and downstream from a restriction enzyme recognition site (a restriction enzyme recognition site between regions d and e) at which a fragment from chromosomal DNA of a coryneform bacterium is inserted. If the promoter probe shuttle vector is the plasmid pPROBE17, the following primer DNA fragments are chemically synthesized corresponding to nucleotide sequences of the plasmid in the 5' and 3'-flanking regions of the EcoRV site.

| GATCAGATCCCAGAATTGAT | (Primer DNA for the 5' end) | (SEQ ID NO:22) |
|---|---|---|
| TGAGCGGGCTTTTTTTTGAT | (Primer DNA for the 3' end) | (SEQ ID NO:23) |

Using the above primer DNA sequences, plasmid DNA extracted from transformants isolated as described above is locally amplified by the PCR method (Nature, 324, 163 (1986)) using a DNA Thermal Cycler model 480 (Takara Shuzo Co., Ltd.). Thus, a portion substantially consisting of the insert DNA fragment into the plasmid can be selectively replicated many times (i.e., amplified).

The insert DNA fragment thus amplified is electrophoresed on an agarose gel followed by determining the size thereof based on the migration distance thereof on the agarose-gel with reference to the migration distance-size standard curve obtained by the electrophoresis of DNA fragments of known sizes (for example, pHY markers by Takara Shuzo Co., Ltd.) on the same agarose gel.

The nucleotide sequence of the amplified insert DNA fragment can be determined by the dideoxy chain termination method (Proceedings of the National Academy Science of the United States of America, 74, 5463 (1977)) using the same primers as used in the PCR method and the products of the PCR method as templates.

The sizes and nucleotide sequences of the insert DNA fragments contained in the above-listed promoter probe shuttle vectors of the twelve transformants were determined as follows:

| No. | Plasmid | | Size of insert DNA fragment | Sequence of insert DNA fragment |
|---|---|---|---|---|
| (1) | pPROBE17 | Km5001 | about 130 bp | SEQ ID NO: 1 |
| (2) | pPROBE17 | Km5002 | about 410 bp | SEQ ID NO: 2 |
| (3) | pPROBE17 | Km5003 | about 420 bp | SEQ ID NO: 3 |
| (4) | pPROBE17 | Km5004 | about 240 bp | SEQ ID NO: 4 |
| (5) | pPROBE17 | Km5005 | about 600 bp | SEQ ID NO: 5 |
| (6) | pPROBE17 | Km5006 | about 590 bp | SEQ ID NO: 6 |
| (7) | pPROBE17 | Km5007 | about 430 bp | SEQ ID NO: 7 |
| (8) | pPROBE17 | Km5008 | about 860 bp | SEQ ID NO: 8 |
| (9) | pPROBE17 | Km5009 | about 1,190 bp | SEQ ID NO: 9 |
| (10) | pPROBE17 | Km5010 | about 710 bp | SEQ ID NO: 10 |
| (11) | pPROBE17 | Km5011 | about 1,000 bp | SEQ ID NO: 11 |
| (12) | pPROBE17 | Km5012 | about 740 bp | SEQ ID NO: 12 |

SEQ ID NO: 1:

| GATCCATGCA | CGCGCGTTGC | TCGGGCTGAA | GGCCTGCTTC | CACCTCAGCG | GTGTGTTCAC | 60 |
| GGCGATCAAT | TTCTTTACCA | CCGAACACAT | ATCCATCACT | GGCCCATACT | CACCCCGACC | 120 |
| TGTAGGAT | | | | | | 128 |

SEQ ID NO: 2:

| GATCCACGCT | GAGCATTTGA | AAGTAACTAG | TCCCGAAGAT | CTTCGGAAAT | GCATAAAGCA | 60 |
| AAAGGCTCTT | AGTGGTTTGT | CAGCGTATGA | TCATCACGTA | GAGTAACACC | CAAGAGTAAG | 120 |
| ACGCAACATC | AATCAATGTG | CAAGGGTTTC | ATTTCTGGAA | ATCGTGGTCA | CCCCACATTC | 180 |
| ACCAGTAATG | AACAAGCTTG | TTTAATGTGA | ATTTGGAGTA | GACCACATGC | CCACTCTCGG | 240 |
| ACCATGGGAA | ATTGGAATCA | TTGTCCTGCT | GATCATCGTG | CTGTTCGGCG | CGAAGAAGCT | 300 |
| GCCTGATGCA | GCTCGTTCCA | TCGGCCAGAT | AACCCGCAGA | TCAAGACATC | AAACATTCGC | 360 |
| ACCATCGGAT | TTCTCATCTA | CGACGGCGTC | TCACCCCTCG | ATTTCACTGG | ATC | 413 |

SEQ ID NO: 3:

| GATCCCTGCC | CAGGCGCGCG | CCCGTCCTGG | CGAGTTCGCA | GATCGAAGGG | TTTGAACACC | 60 |
| GTAGAGGGTG | GCGTCGACAA | GCAAATTTCT | GGTTTGCTGC | AAGCCTTGCC | CTGTACTGGT | 120 |
| GCGCCGCGCT | GTGGATCGCG | CTGGACGTTG | GGTATTTCTG | GGGCGACGCG | CTCTCGCGCA | 180 |
| CCCAAGGCGC | CCTATCCGCG | CTGTACTCGC | GCAACCCCAC | GTTGTCGGCG | ATCGGTTACG | 240 |
| TGTTTACCCC | TCTGACCACC | GTGGTGCAGA | TTCCATTGGT | GGCGCTGAGC | CCCTGGGTCC | 300 |
| CGGAATTCAC | GCGCGCCGGG | TTGGCAGGCG | CATTGGTGTC | ATCAGTGTTC | ATGGCGGCTT | 360 |
| CAGTGAGGCA | ATTGTGGTTG | ATTGCCAGCG | AGCGCAACAT | CCGGTATTGG | CTCGCGGTGG | 420 |
| TAG | | | | | | 423 |

SEQ ID NO: 4:

| GATCTTTCAG | CTGCTCACAC | GTGATTGTAC | CGCGTCAATG | GAAGTGATTG | GCCGCTTCCT | 60 |
| TGCCTTGCTG | GAATTGTATA | AGGCACGCGC | TATTGAAACC | TTGCAAGAGG | AGCCACTCGG | 120 |
| CGAGCTTAAA | GTTTCGTGGA | CTGGCATTGA | TGTCGATCCA | GCAGTCGTCG | CGGCGAGTGA | 180 |
| CTGGGAGTAA | TCAGTTTTTC | TTAAGGAAAC | GTTGCTGAAT | TAGTTTTAGT | GACCTAAGAT | 240 |
| C | | | | | | 241 |

SEQ ID NO: 5:

| GATCTTGTCG | ACGCCCCCG | CGACAGTGGC | GCACAAATCC | TCACGGGCGG | CCAACCCTCA | 60 |
| GATGGACCTG | GAAACTTCTA | TCCGGCCACG | ATTGTTACAG | ACATTGCTCC | GGAATATCCT | 120 |
| CTGGTTGTTG | AAGAACAGTT | CGGACCAGCG | CTTCCAATAG | TCCGATACTC | CAATATTGAT | 180 |
| GAAGCCATTG | GTTGGGCAAA | TGGACTTGAA | GTAGGTCTTG | GAGCTTCTGT | GTGGTCCGCT | 240 |
| GATCGGAATC | GCGCAATGGA | TGTAGCTAGG | CAGATTCAGG | CTGGAACAGT | ATGGATTAAT | 300 |
| AACCATGCCC | GCCCTGATCC | AAGAATTCCT | TTCGGCGGAA | TCAAGCAATC | GGGATACGGC | 360 |
| CTTGAATTTG | GTGCTGATGG | CCTCAAAGCG | GTTGCGGTCC | CCAAGGTCTA | CAACGGTTAA | 420 |
| TTGTTTGATG | TTGAGAATTC | TCCGGGCCGA | TTATTGTCGT | AGTTTTCTGC | ATTGGTGCTT | 480 |
| GGCAAGGAGA | TCTCCCCCTG | GTAAAGCTTG | ATCAAATCCC | ATTTGACCAG | GGGATTTGGT | 540 |
| GTATTGTTAA | CTTGAGGGTA | GAGTATATTC | TCGTTCCTAA | AGGGGCCTAT | AGATC | 595 |

SEQ ID NO: 6:

| GATCTGAAGC | AACACCTGAT | CAACCACACC | CCTTGGGGCG | CAAAGATCAC | GGTCGAGATC | 60 |
| GATGACATTA | ACCAACCGTT | CTCCACCGAT | ATTACCGCCC | CTGCAATGTC | CACCCTGGCG | 120 |
| TCCTGCCTGA | GCGCTGCGTA | CGAGGGCAAG | GATCTTGTCA | CCGAAGGCAG | CGGCGGATCC | 180 |

-continued

| | | | | | | |
|---|---|---|---|---|---|---|
| AYTCCACTGT | GCACCGAACT | GATTGAGGTC | AACCCAGAAG | CAGAATTGGC | ACTCTACGGT | 240 |
| GTGGAAGAAC | CCCTCACCGT | TATCCACTCC | GCTAATGAAT | CTGTTGACCC | CAATGAGATT | 300 |
| CGCGATATCG | CCACCGCAGA | AGCATTGTTC | CTGCTCAACT | ACACCAAGTA | GACTTAGAAG | 360 |
| CAGGCATTAA | CACTGCCACC | TTTGCAAAAT | TAACCACCCC | CTGATGGGGT | CGTTTTTTCA | 420 |
| TGAGTTGAAA | AAAGTGTCTT | GATTCACTTT | GTGATGACGG | TTACCATAGC | CATCGTGACT | 480 |
| AAAAACATTG | ACCTTAAGCG | AGTAGCCAAG | GCTACGTACC | CTACTGCGGG | ATAGATGGAC | 540 |
| TGGCTCCCCG | CACTAGGGAA | GTAGTCGTTA | ATCAACACCA | AGAAGATC | | 588 |

SEQ ID NO: 7:

| | | | | | | |
|---|---|---|---|---|---|---|
| GATCTCAACG | TTTAGCGGCT | CTCTGGATCG | TGAAATGTCA | ACGTTCATGG | AAGCCAATGT | 60 |
| AGTGGGGTCG | CGTCGAAAAG | CGCGCTTTAA | GGCCGACACG | CCCAAAAAGT | TTTACCTTTA | 120 |
| AAAACTACCC | GCACGCAGCA | CGAACCTGTT | CAGTGATGCA | AATCACCGCT | AAAATATTGT | 180 |
| GGACGTTACC | CCCGCCTACC | GCTACGATTT | CAAAACATGA | CCATTTCCTC | ACCTTTGATT | 240 |
| GACGTCGCCA | ACCTTCCAGA | CATCAACACC | ACTGCCGCCA | AGATCGCCGA | CTTTAAGGCT | 300 |
| CGCCGCGCGG | AAGCCCATTT | CCCCATGGGT | GAAAAGGCAG | TAGAGAAGGT | CCACGCTGCT | 360 |
| GGACGCCTCA | CTGCCCGTGA | CCGCTTGGAC | TACTTACTCG | ATGAGGGCTC | CTTCATCGAG | 420 |
| ACCGATCAGA | TC | | | | | 432 |

SEQ ID NO: 8:

| | | | | | | |
|---|---|---|---|---|---|---|
| CCGTTATATA | TAAGGAATAG | GCAACAAGTC | CCACTGGCTG | TGCCAATAGC | CAGCACACAA | 60 |
| ACATTGAATC | CCCACAGATC | ATCACCCAAA | ACTACGGGGC | TTGCAGTTCC | AATGCGATCA | 120 |
| AACCCATGGA | CAACATTGCC | ATGCGGATGC | ATGAGGAGA | GCGGTAGATT | | 180 |
| AGCCAACCGT | CAATTAATGA | CAATTGCCAC | CACAACAGCT | AACGCGAAGA | AGAAATCTGC | 240 |
| GACGACTGGA | AAACCATGGA | TTTTCAACAG | TGATGACAAC | AATGAGATGC | CCATGAGGGA | 300 |
| ACCAGCCCAC | GAGGGGCCCC | TTTGTGACAT | CGGCGTAGTT | GTTCAACTAT | AATGGAACGC | 360 |
| TGATCGTGGA | CAAGAGTTAA | CCATGAGATT | GATTCACCCC | TTTAAGCCTC | CAAAGAAGTA | 420 |
| GTTGACTCAA | CGCATTTCGG | CATTTAAAAA | AGCCGAGACC | AAATGAGACT | TTCCAGGAGA | 480 |
| AGGCACCAGG | GACATGAACA | ATTGATCGGC | TGACCAACTC | TATAAGAGAT | GCACCTCAAG | 540 |
| TTTGGGGATA | CTTATTCGGC | GTTTCTGGGG | ACAAATACGT | TCCCTATTGT | TGTATATAGG | 600 |
| TATTCGCACT | TAAGAAACAT | CTCTCATGGA | AAGAAGCTAG | GCGGAAAGGG | CGTTAAGTAC | 660 |
| TTGCCATTTA | ATCCTCAGCA | TCACTCGGAT | CAGTCGGAGA | TGTCGATGAA | AATGCACCAG | 720 |
| GAGCCGTGGA | GAGCAGCATG | GTAGAAAACA | ACGTAGCAAA | AAAGACGGTC | GCTAAAAAGA | 780 |
| CCGCACGCAA | GACCGCACGC | AAAGCAGCCC | CGCGCGTGGC | AACCCCATTG | GGAGTCGCAT | 840 |
| CTGAGTCTCC | CATTTCGG | | | | | 858 |

SEQ ID NO: 9:

| | | | | | | |
|---|---|---|---|---|---|---|
| TTACCGCAAG | CTCAATACGA | CTCACTATAG | GGGCCCGGTA | CCGAGCTCAC | TAGTTTAATT | 60 |
| AAAAGCTTAT | CGGCCTGAGG | TGAGAAGGGT | TCCGGACCCC | AGAATTCTCG | CGATAATTAA | 120 |
| TTAATAGCCC | GCCGTAATGA | GCGGGCTTTT | TTTTGATCCC | CGCCACCATA | ACCCACGAAT | 180 |
| CCTAACAAGT | CCCTGCATTC | TCGATGGCTT | TTTGGCTTTA | ATCCGTTTTG | GTTCAGGAAA | 240 |
| CTTACAAGAT | CTTTTACGCT | AGATGAAACT | TGCCATCGAA | CAGAATCCTG | CAGATGAAAT | 300 |
| CTTTCAGCAC | CATACATATC | GGTAATTCAT | AAAATGCTCC | AGTGTCAAGC | TCTCGCAACG | 360 |
| TAATCGTTGC | TGTTCACGGA | GTTCTTACTA | GCTGCTCGGG | CGATCAATTT | GTCATTAGAT | 420 |
| TATGCAGTTA | TAGGGAGAAC | GGACACAAAA | GGGAGGGACC | TGACTGTACA | CTGTACTCCC | 480 |
| GCTAGCACGT | GTGTGTGATG | ACACAGCTCA | GAAGCATTGC | AGTTGGACAA | CCCCTAGATA | 540 |
| AGACTGCACA | AAGTAGGACA | TATCTCTCAC | TTTTCTTATT | GTTTTCGGGC | AAAACTAATC | 600 |
| CAGAACCTTT | CTAAAGGCCC | TGATCAATCA | GGATTTCTGC | GTGTCGACGT | GATGCCACAC | 660 |
| CTCGTTGGGC | AAGCACCTTC | TGCAGGCGAA | CTCCGTCAGA | GTCATTGCGG | CTTAAGAAAC | 720 |
| CCATCGACCA | ATCGTCGTCG | GATTTTACGT | TTTGCTTCTT | GGCAGGCTTA | GCGTTGGAGA | 780 |
| GAAGAATCTC | ATCCTTCTTC | TGAGGCTGCT | GGCGTGTGTT | TGGGCGGGAT | GATCCTGGCT | 840 |
| TGTAGCCACG | AACTGAAGAC | CGGTATCCGC | CAGAGCGATT | GCTCTGCTTC | TTGTCCGGTG | 900 |
| TGCCATCTCG | GCGAGCGGGT | GGGGTCACGT | AAGTGTCCTT | AATCTTGAGA | GAAAACGTAT | 960 |
| GAAATTGAAT | CCCGTGAATT | CTAGCCTATT | TTAGGAGATT | TTAATAGTCG | GGGCTTTAAC | 1020 |
| TGATGCTTTA | GAAGTCTTCA | TCAATGGAGT | CAACATCCGG | CAAAAGCGGT | GCTAGATCCG | 1080 |
| GTAATTTATC | CAAAGAATCA | ATACCCAACA | GCTCAAGCAG | GCAATTCCCG | TTGTGCCCAT | 1140 |
| AGCGGTGCGC | GCCCGTTGAT | TCGTCCACAT | CGACTTCTTT | GACTAGG | | 1187 |

SEQ ID NO: 10:

| | | | | | | |
|---|---|---|---|---|---|---|
| CTCAATTGCC | TCGTCTGAAG | GATGCTGACA | CTGAACTGAC | AGACGAGGAC | CGGGCCTAAG | 60 |
| ATTTTTTCGG | TGTATGGCGC | GGGCTGTGAG | GGGGATGTCG | TCGATAAGCG | TAGGGCCGAA | 120 |
| GAAGAAGCCC | TCCTCGTGGC | GTCTACGGCT | GCACGTTACG | CCGTCCACGA | CTGATCTTGG | 180 |
| CAGCCGGTCT | GGCCTGACCG | ATGCGACATA | AGAAGCGACC | TTCTCGCGGT | GGCTGCGGTG | 240 |
| ATTAGTGGGC | CCAGGTCCGC | TCAGCCTGCT | CGCGCCGGCA | CCGTTGCCGA | TGCGAAGGGT | 300 |
| GTCGATGCGG | TCCTTGATCT | TCTCAATGAG | CTTTATTCCT | GGGCTTTGGG | AGCTTCAAAC | 360 |
| AGGAGGCATC | AAATTTGGGG | TAGTGCAGGG | CCTTTGAATC | CCACCTCACA | GATAGTATTC | 420 |
| AGGCATTTCC | TTGTCACGAT | GGTTTATCCT | TGGACACAAC | ATCAAAAGTG | GGGTACATCA | 480 |
| TATGCTTCCG | GTTGAAAGTG | ACCTATCTGA | AAAGACTTGG | CAGAACCTTA | AGCAATGGTG | 540 |
| TGAACTGCGT | TAACGAATTT | TGTCGGACGT | TAAAATGCG | CATTCTGCTT | GCTGAAGTGG | 600 |
| CACACCTATG | TGTTCTGCTT | GGGATAGCAG | TGCGGGAAAA | ATTTGAAAAA | GTCCGATTAC | 660 |
| CTTGAGGAGT | ATTCAATGTC | ATGACGCATT | GCTTCAGAAA | ACTGCGCTCC | AAG | 713 |

SEQ ID NO: 11:

| | | | | | | |
|---|---|---|---|---|---|---|
| CTGAAGGAGT | ACACCTTCGA | TCTGCTCTAC | AGATCTTTAG | TGATAACAGA | AACTCAGTAC | 60 |
| TCCGAAGATC | TCTACTGACA | GATCTTGGAT | GGACCCGAGG | ATGTTAAAGC | GATTCCCTTC | 120 |
| GCTACAACAG | CAACAAGGCC | CTCAACAACC | TTGGCTACGA | AGGACTCTTC | CCAGCGGATG | 180 |
| AAACCAAGGT | GTCCCCAAAC | ATCTTGTCTG | CGCTGTCACC | AAAACGCTGAT | GAGAACCACG | 240 |
| ACTTCTTCTC | CGGCTCCGGT | TCCTCTTACG | TTATTGGTAA | GGCAGAAAAC | ACCCGAGGAT | 300 |
| GATGACCTGG | GACTTTCTAA | CTTTTAAAAA | GCTGAAGCGG | TCTACCGGCC | TGTAGGGTAA | 360 |
| CCTCAACCCG | TTAGAGCGTT | TTCGGGTTTC | CTGGTGGGGA | CTTAAAGGTG | CGGGGTTTTC | 420 |
| CGAAGCCGCA | ATATCAGGGG | TAAGGGACGA | CCAGGCACCC | CTGTGGCCCC | TCGGCAGCGC | 480 |

-continued

| | | | | | | |
|---|---|---|---|---|---|---|
| ATCACGCTTT | AGGAGAAAAC | GCCCCTGGAA | TGGCGTCTCA | ACCATTCAGA | TTGAACCCCG | 540 |
| GCAGGGGGGA | ATTATGAAAT | CTGTGACAGG | GGTTAACCGT | GGGGGTGGGC | TTCCTGGCAG | 600 |
| AAATGTCCGT | CAAATTGTGA | ACCCCTTCAC | ACCTTTGGTT | GAAAGCACTG | CCCACAAGTG | 660 |
| ACTGAACCTG | GCAGCGACCT | CATGAATTGT | TTGAAAAACA | TTTTTTTTGG | CACGAAAACG | 720 |
| GGGATACACG | TTAGCTGCAT | ACCAGCCTTT | TTGGGTTGCA | TCAGGATCCT | GCCTGTGGCC | 780 |
| TTATGATCAG | GCAGTGTTGT | TAAAGGACGA | TCGGTAATCC | GAATGGTTCG | TCCCGTAGTC | 840 |
| AGGAGGAACC | TATGACCGCT | GTGGCGCCTA | GGGTCGACGG | GCACGTGCCC | CTCTACGAGG | 900 |
| CCCGAGCCCG | ACAGGCCATG | CACGCAAGGG | CAGAAAGCAT | GGTTAATGAT | GACCACCACC | 960 |
| GGACCACAAG | CAGCTTGGGC | ATTATGTACA | TCATTATGTC | CTTCAG | | 1006 |
| SEQ ID NO: 12: | | | | | | |
| CTGCGTTGGC | CTTAAGGGAG | ATCACTTCAA | TTTCTTCATT | GTGAGGCAGC | CAGAACTCCA | 60 |
| CCACCTTTTC | CTGCTCTGAA | AGTCCATCCA | CTGTGAAGCA | CCTGCGGATC | TTCCAGACGC | 120 |
| CGTTCCGTGG | CGCCGGTGAT | GAAATTGACT | TCCGTGGTCT | CGCCCCCGGA | GGTTGGCGTG | 180 |
| GAAGATGTGG | GGGCGCCGTC | GATAAGCACA | TCAATCTTGC | CGCCCGGCCG | GCCGGAATCG | 240 |
| AGGTACACCA | CCGAGTGGAN | TACGTGGTCA | GCGTGAAGGA | GGTGGCGGTT | GGTGCGACAC | 300 |
| ACACGGCACG | CCCGTTGGTT | GGCGTTCCAT | CGCGCTAACT | TGGGATCACA | GTACGGTCTA | 360 |
| CTTATTCCTT | TGCTGAGCCA | ATCGGGCGAA | GGCCCCTTGT | TAGTGGTTCA | ATTTCGGTTG | 420 |
| CGCCGTGAAT | TAAATTCGGG | ATTTCATGAG | CTTAACCGTA | CCGCTCTTGC | AGAGTTCACA | 480 |
| GGGTAAACCC | TAAATGGAAC | AACCCATTGC | CAATATGTTG | GTTAAGTTGT | ACGCAAGTAA | 540 |
| ATCTTTTCAA | TCGTGGAAGC | AGGGCTCACA | GTCTAATGGC | ACGTATGCAG | GAAAGCGCCG | 600 |
| ATCTTCCAAA | TGTTCCTTCT | GCGGAAAGAG | CCAAAAGCAG | GTAAAAAAAC | TTCATCGCGG | 660 |
| GTGGCGCCGG | TATATATCTT | GTGATGAGTG | CATTGAGCTT | GTGCAACGAG | ATTATTGAAG | 720 |
| AAGAACTCAG | GTCAAGA | | | | | 737 |

The promoter DNA fragments of the present invention which includes any one of the above-listed nucleotide sequences and have a greater promoter strength than the tac promoter may not necessarily be a fragment isolated from naturally occurring chromosomal DNA of a coryneform bacteria, but may also be a fragment synthesized by a DNA synthesizer such as an Applied Biosystems model 380A DNA Synthesizer.

Some nucleotides of the above nucleotide sequence of the DNA fragment of the invention obtained from the chromosomal DNA of Brevibacterium flavum MJ-233 (FERM BP-1497 may be replaced with other nucleotides or deleted, or other nucleotides may be inserted into the sequences, as long as such nucleotide sequence changes will not substantially reduce the promoter strength of the DNA fragment which is greater than that of the tac promoter. Such DNA fragment derivatives are included in the promoter DNA fragment of the present invention.

Controllable Promoter DNA Fragment

Herein described will be a controllable promoter DNA fragment which is isolated from coryneform bacteria chromosomal DNA and functional in coryneform bacteria cells, wherein the promoter function of the controllable promoter DNA is controllable by replacing at least one substance which is contained in the culture medium and is assimilable by for the host coryneform bacteria cells, with at least one other substance which is also assimilable by the host cells. The term "at least one substance which is contained in the culture medium and is assimilable by the host coryneform bacteria cells" means at least one of the substances necessary for coryneform bacteria to grow, such as carbon sources, nitrogen sources or other nutrients. Examples of such substances are glucose, fructose, ethanol, methanol, casein hydrolysates, yeast extracts, amino acids, urea, blackstrap molasses, and ammonium sulfate. Preferred among them are glucose, fructose, ethanol, casein hydrolysates and yeast extracts. Any single substance or any combination of several of such substances may be contained in a minimal medium. The concentrations of such substances in media may vary within such ranges that coryneform bacteria cells can use such substances to grow. Suitable concentrations of the preferred substances are: glucose, 5-0.01%; ethanol, 5-0.01%; fructose, 5-0.01%; casein hydrolysates, 1-0.01%; and yeast extracts, 1-0.01%. The term "minimal medium" means a medium consisting of substances which have known chemical structures and are essential for coryneform bacteria cells to grow. Examples of such essential substances to be contained in a minimal medium are: carbon sources, such as glucose and ethanol; nitrogen sources, such as ammonium, ammonium sulfate, ammonium chloride, ammonium nitrate and urea; inorganic salts, such as dipotassium hydrogenphosphate, potassium dihydrogenphosphate and magnesium sulfate; and other nutrients, such as biotin and vitamins.

A controllable promoter DNA fragment according to the present invention can be obtained as follows:

First coryneform bacteria cells to which the above-described promoter probe shuttle vectors containing DNA fragments obtained from coryneform bacteria chromosomal DNA are introduced and are cultured in a minimal medium, followed by confirmation of the expression of the selectable marker gene by the above-described method. The transformants containing the promoter probe shuttle vectors are thus obtained. Secondly, each of the transformants is cultured in a minimal medium containing at least one of the above-described substances assimilable by coryneform bacteria cells, followed by confirming the expression of the reporter gene and determining the expression strength thereof. Then, each transformant is cultured in a minimal medium in which at least one substance that is assimilable by the host coryneform bacteria cells and contained in the minimal medium previously used is replaced with at least one other substance assimilable by the host coryneform bacteria cells, followed by confirming the expression of the reporter gene and determining the expression strength thereof. Thus, a transformant capable of controlling the expression of the reporter gene is obtained by replacing at least one substance that is contained in the medium and assimilable by the host coryneform bacteria cells with at least one other substance also assimilable by the host coryneform bacteria cells.

Methods for replacing at least one substance which is contained in the culture medium for the host coryneform bacterium cells and is assimilable by the host coryneform bacterium cells with at least one other substance which is assimilable by the host coryneform bacterium cells are not specifically restricted.

Such methods include:

1) cultivating cells in one medium containing one assimilable substance and collecting cells by centrifugation or by filtration, such methods known as usual and inoculating the collected cells to other medium containing other assimilable substance, or 2) cultivating cells in one medium containing an assimilable substance and adding another substance when one substance is almost completely utilized.

To determine whether the transformant's ability to control the expression of the reporter gene depends on the DNA fragments inserted into the promoter probe shuttle vector, that is, to eliminate the transformants which have acquired the ability to control the reporter gene expression due to mutations on their chromosomal DNA, plasmid DNA is extracted from each transformant and introduced again into other coryneform bacteria cells. The coryneform bacteria cells transformed with the plasmid DNA extracted from the transformant are examined to see whether the reporter gene expression strength in the cells changes when at least one substance that is assimilable by the cells and contained in the medium is replaced with at least one other substance assimilable by the cells, by the method as described above.

In this manner, a coryneform bacteria transformant harboring a promoter probe shuttle vector containing a promoter DNA fragment whose promoter function is controllable by replacing at least one substance that is contained in the medium and assimilable by the coryneform bacteria cells with at least one other substance assimilable able by the coryneform bacteria cells can be obtained.

Examples of the transformants thus obtained are: the below-listed strains of Brevibacterium flavum MJ-233 which have been transformed with plasmids obtained by inserting AluI-HaeIII restriction fragments of chromosomal DNA of Brevibacterium flavum MJ-233 (FERM BP-1497) into the above-described promotor probe shuttle vector pPROBE17 at the restriction enzyme EcoRV recognition site, and which have the following characteristics. These transformants and the plasmids contained therein are named as follows.

(i) Transformants whose expression of the reporter gene is repressed by glucose contained in the media (the transformants become sensitive to kanamycin), and induced by replacing the glucose with ethanol (they become resistant to kanamycin concentrations of 100 µg/ml or greater):

| No. | Bacteria strain | Plasmid |
|---|---|---|
| (13) | Brevibacterium flavum MJ233 KE101 | pPROBE17 KE101 |
| (14) | Brevibacterium flavum MJ233 KE102 | pPROBE17 KE102 | ii) A transformant whose expression of the reporter gone is repressed by ethanol contained in the media (the transformant becomes sensitive to kanamycin), and induced by replacing the ethanol with glucose (it becomes resistant to a kanamycin concentration of 100 µg/ml or greater):

| No. | Bacteria strain | Plasmid |
|---|---|---|
| (15) | Brevibacterium flavum MJ233 KG101 | pPROBE17 KG101 |

(iii) A transformant whose expression of the reporter gene is repressed by glucose contained in the media (that is, the transformant becomes sensitive to kanamycin), and induced by replacing the glucose with fructose (that is, it becomes resistant to a kanamycin concentration of 100 µg/ml or greater):

| No. | Bacteria strain | Plasmid |
|---|---|---|
| (16) | Brevibacterium flavum MJ233 KF101 | pPROBE17 KF101 |

(iv) A transformant whose expression of the reporter gene is repressed by a combination of casein hydrolysates, yeast extracts and glucose contained in the media (the transformant becomes sensitive to kanamycin), and induced by replacing the combination of casein hydrolysates, yeast extracts and glucose with glucose (it becomes resistant to a kanamycin concentration of 100 µg/ml or greater):

| No. | Bacteria strain | Plasmid |
|---|---|---|
| (17) | Brevibacterium flavum MJ233 KG102 | pPROBE17 KG102 |

(v) Transformants whose expression of the reporter gene is repressed by glucose contained in the media (the transformants become sensitive to kanamycin), and induced by replacing the glucose with a combination of casein hydrolysates, yeast extracts and glucose (they become resistant to kanamycin concentrations of 100 g/m or greater):

| No. | Bacteria strain | Plasmid |
|---|---|---|
| (18) | Brevibacterium flavum MJ233 KGYC101 | pPROBE17 KGYC101 |
| (19) | Brevibacterium flavum MJ233 KGYC102 | pPROBE17 KGYC102 |
| (20) | Brevibacterium flavum MJ233 KGYC103 | pPROBE17 KGYC103 |

The sizes and nucleotide sequences of the thus-obtained controllable promoter DNA fragments according to the present invention can be determined by the method as described above. Below listed are the sizes and nucleotide sequences of the DNA fragments inserted into the promoter probe shuttle vector pPROBE17 contained in the transformants isolated as described above.

| No. | Plasmid | | Size of insert DNA fragment | Sequence of insert DNA fragment |
|---|---|---|---|---|
| (13) | pPROBE17 | KE101 | about 2,300 bp | SEQ ID NO: 13 |
| (14) | pPROBE17 | KE102 | about 550 bp | SEQ ID NO: 14 |
| (15) | pPROBE17 | KG101 | about 550 bp | SEQ ID NO: 15 |
| (16) | pPROBE17 | KF101 | about 2,500 bp | SEQ ID NO: 16 |
| (17) | pPROBE17 | KG102 | about 570 bp | SEQ ID NO: 17 |
| (18) | pPROBE17 | KGYC101 | about 1,110 bp | SEQ ID NO: 18 |
| (19) | pPROBE17 | KGYC102 | about 2,200 bp | SEQ ID NO: 19 |
| (20) | pPROBE17 | KGYC103 | about 2,300 bp | SEQ ID NO: 20 |

SEQ ID NO: 13:

| | | | | | | |
|---|---|---|---|---|---|---|
| CTACTTCTTC | TTCACCGAAG | TATTCCTTAG | GGTCGATCTC | GTTACCCTCG | GAGTCCTTCA | 60 |
| CGTTTACGCG | GCAGATAGCC | TGCGCAAGAG | CCTTGCCACG | GCGAACGTCG | GAGAAGAGGT | 120 |
| TCGCGATCTG | GCCGGACTGC | TCCAGCTGAC | CGATGAACTG | GTTTGGGTCC | ATGCCGTAAG | 180 |
| ACCGTGCGGT | GAACAGGATG | TGGTCGGTGA | GCTCCTCGTG | CCGCTGATCC | GACTCCGAGC | 240 |
| CCGACCCAGC | CACCACCGAT | GACGACCAGC | TCTTCACCTT | CACCGAAGTT | GCCTTGATCG | 300 |
| CGCCAGAGTC | TTCCACGGCG | CGCAGGTAGT | GCACATTAGA | GCCGTCGGCT | CCGGAATTGC | 360 |
| AAGTTTGCGA | CTGCTGAGCA | AGTAGCAAGA | ACTAGTTTGT | CGTAGTTAAT | GGTCTCAGTG | 420 |
| TTTCCGCCAT | CATCAACGGT | GACTCGGCGT | GAACCCGCAT | CAAYTGCCGC | GACGCACACC | 480 |
| TTGACGCAGC | GTGACATTGT | TTTCTTTGCA | CCACCCCGCC | GGGTGAACAA | TCGCCTTTTC | 540 |
| AAAGCCTACT | CTTCCCGCCA | TGCACTCCTT | TGACAGCGGT | GGGCGTTCAC | ATGGCAGATG | 600 |
| ATTTTCTGCT | GTGATGAGCG | TGATGGAGCC | TTCATGCCCG | TTTACACGCA | GTGCCTCTGC | 660 |
| GGCCCCCGCT | CCGGCTGAAC | CGCCGCCGAT | GATGACGATG | CTTTGTGGTG | TGCCCATGCT | 720 |
| GTACTCCTAG | TCCCTAAAAA | GTGGACGGTC | AGGCGCAAGG | CCGACCGCAT | GGTCTATACG | 780 |
| CCATGCTAGT | AAAAGGCCG | AAACCCTCGG | CGAGCGCCCT | AAATACCCGG | CCCCAACTCG | 840 |
| GGGTGTGAGG | CAGCACACAA | GACGAAACCC | TAACGAAATC | GCCAGACTCC | TCGCAATCAC | 900 |
| AAGAAGCGAC | GACTAGCCTG | TGGGGACAAA | CTATCTCAAG | AATTTATTCA | ACAAAGGAGT | 960 |
| TCTTCGCACA | TGAAGGAAGT | AGCAGTCAAC | GAAGTCCCAG | CAGGCGCGCA | GCTAATGCAC | 1020 |
| TGTCACTCTT | TCGACGTGAT | GTGCATCGGT | TTACGTGGTG | GCGTGGTTCA | CACATTGCTC | 1080 |
| CATCGGGCAT | TGGTGCGTCA | ATCGGTTTGG | GTTTTTAAGT | TTTGTGCGGG | GGTGGTCACC | 1140 |
| CCTGTTGTGA | ACTTTGCAAA | GTTATGACTT | CGCAGAAAAA | GTCGGCGGG | GAGTTGCTAG | 1200 |
| TACGGATGTA | CTGGGCAAAT | GCTCTGAAAT | GGGAAAATGC | AGGCACCACA | ACTTTCCCTA | 1260 |
| GTTTTGAAGG | TGTGACCTAG | ATAAAAGTCG | GGGTTAGGCG | GGGGTAAATG | ACTAGGTAAA | 1320 |
| GGTTCGCAAA | CCCCCTTTTG | TTGGTGACGG | TGATCACTTA | GTCTGATCAC | ATCGCCAAAC | 1380 |
| ACGATAAGGG | TTGAAATCGA | AAGAAGAGCG | GCACCTAGAT | TCCAAGGGTA | GCCAGAGTGC | 1440 |
| TTTTCTTAAA | AGAGTTTTCA | CAACCGTTAA | CGGCCTAGCC | AAACAAGAAG | GATTCGCATT | 1500 |
| NCAGCTTCTG | GTTTAGGCAC | AGGTCATCTA | AAACCCATGC | TTTAAAAGGA | GCCTTCAATG | 1560 |
| ACTGAACAGG | AACTGTTGTC | TGCTCAGACT | GCCGACAACG | CTGGAACTGA | CAGCACCGAA | 1620 |
| CGCGTTGACG | CGGGCGGAAT | GCAGGTTGCA | AAACTTCTCT | ACGACTTTGT | AACCGAAGCG | 1680 |
| GTACTCCCTC | GCGTGGGTGT | GGATGCGGAA | AAGTTCTGGT | CCGGATTCGC | CGCCATCGCC | 1740 |
| CGGGACCTCA | CCCCACGCAA | CCGCGAACTG | CTTGCTCGTC | GCGATGAACT | GCAGACGCTT | 1800 |
| ATCGACGACT | ACCACCGCAA | CAACTCCGGC | ACCATCGACC | AAGACGCGTA | CGAGGATTTC | 1860 |
| CTTAAAGAAA | TCGGATACTT | GGTTGAGGAG | CCAGAAGCTG | CAGAAATCCG | TACCCAAAAC | 1920 |
| GTCGATACGG | AAATCTCCAG | CACCGCAGAC | CTCAGCTGGT | TGTGCCAATT | CTGAACGCAC | 1980 |
| GTTCGCGCTG | AATGCTGCCA | ATGCTCGTTG | GGGTTCCCTC | TACGATGCGT | TGTACGGCAC | 2040 |
| CAACGCCATC | CCAGAAACTG | ATGGCGCTGA | AAAGGGCAAG | GAGTACAACC | CGGTCCGCGG | 2100 |
| CCAGAAGGTC | ATCGAGTCGG | GTCGTCAATT | CCTCGACAGC | GTTGTCCCAC | TGGACGGGTG | 2160 |
| CTTCGCATGC | CGATGTTGAG | AAGTACAACA | TCACGGATGG | AAA | | 2203 |

SEQ ID NO: 14:

| | | | | | | |
|---|---|---|---|---|---|---|
| CCTCATGGAT | GTTGACATCG | ATATGGATTC | CGACATCTGA | GCAGATCCTC | TCCTGGCGGA | 60 |
| CACAGACGA | TCCCTGCTCT | CCCTGGAAGC | TGGCACCTGT | GACCGTTGCC | TTCGACACGA | 120 |
| CACATGCTGA | CCACCCTGGA | GAACTCCGGC | CTATCGTGCC | GATCGTTCCA | GGCGCTGTGA | 180 |
| TTTTTGATTT | GTTGGTGGGC | GATCCCAAAA | ACAGGCCGCT | GAGAAAGTTT | TCCACACTAA | 240 |
| AATAGTGTGA | TTCTGCCGAA | TCTGTTGTTT | TACTTTTGAA | ACTGCGGGAT | CATGAAAAGT | 300 |
| AGTGAAAAGT | GAATTTTAGT | TCTGTGCTTT | CTCTTCCCTT | TAAGTGAACC | TTTTGTTGGA | 360 |
| TCTTCATTAA | AAAAATGAAA | ACCTCGTCGG | AATGCAACTT | GGGATCACTG | TCTCGGGCAA | 420 |
| GAAACGGCCT | TAAAAAAGGG | GAGTGATTGT | GAGTGCTTGA | TTTCTTAGCT | GCGAACCCGC | 480 |
| TTGATTGCTG | CTTGGTGGTT | ATTTTGGCCA | CGGGTGACCA | CTCCCAGACT | CAGCTGCCAG | 540 |
| GTGGTCAGTG | G | | | | | 551 |

SEQ ID NO: 15:

| | | | | | | |
|---|---|---|---|---|---|---|
| GATCCTCATG | GATGTTGACA | TCGATATGGA | TTCCGACATC | GAGCAGATCC | TCTCCGGCGG | 60 |
| ACACAGCGCA | TCCCTGCTCT | CCCTGGAAGC | TGGCACCTGT | GACCGTTGCC | TCGCACACGA | 120 |
| CACCATGCTG | ACCACCCTGG | AGAACTCCGG | CCTATCGTGC | CGATCGTTCC | AGGCGCTGTG | 180 |
| ATTTTTGATT | TGTTGGTGGG | CGATCCCAAA | AACAGGCCGC | TGAGAAAGTT | TTCCACACTA | 240 |
| AAATAGTGTG | ATTCTGTCCG | AATCTGTTGT | TTTAGTTTTG | AAACTGCGGG | ATCATGGAAA | 300 |
| GTAGTGAAAA | GTGAATTTTA | GTTCTGTGCT | TTCTCTGCCC | TTTAAGTGAA | CCTTTTGTTG | 360 |
| GATCTTGCAT | TAAAAAAATG | AAAACCTCGT | CGGGAATGCA | ACTTGGGATC | ACGTCTCGGG | 420 |
| CAAGAAACGT | CCTTAAAAAA | GCGGAGTGAT | TGTGAGTGCT | TGATTTCTTA | GCTGCGAACC | 480 |
| CGCTGATTGC | GCTGGTCGTT | ATTTTGCCCA | CGGTGACCAC | TCCCGACTCG | GCGCCGGTGG | 540 |
| TCGTGGATC | | | | | | 549 |

SEQ ID NO: 16:

| | | | | | | |
|---|---|---|---|---|---|---|
| TCGGGCCGGT | GCCAATGCAT | CAGGGAGATT | TGGATATACG | GCCCACAATT | CTTTGGTTCC | 60 |
| GGTCGATGGA | GTAGTGAAGG | TGACACCCGA | TCCGATGGTG | ACGTTGCTCA | TCTCTGTTTC | 120 |
| TTTTACATTC | GCGGTGATCT | TCAGTTCGGA | ATCATCAGCA | ACACTCAACA | GTGCGCCGGC | 180 |
| TGCTGGTTGA | CCTTGCCCTG | CCTGCCACGG | ATGAACAATG | CCTGAGTATG | CGGATCGACG | 240 |
| GTGGTGTGTT | GATATCATCC | GAACTGGGAC | GTGATCTGGT | GCCGCTTAAT | ATCTACTGAT | 300 |
| GCAACCTAAA | GTGCATAATG | CGCTTATTTT | CCCCAATGGT | GTTGGTGAAA | ATCCCGTCTC | 360 |
| GAGCCAAGTT | TGCGCTTGTG | TGCTATTCGG | CTCATCACCG | CGCCTGTGCA | CCGGCTAGTC | 420 |
| TGAGTCAACT | TTTCCGAGTG | AATCAATGTA | GATCCGCTCG | GCTTTTTCTA | GACCTTCAGT | 480 |
| GGTGGATGCA | ACGCGTCGCT | CAGTTTCCTC | CAAAACGGTG | TACGACTGCA | AGTTAGGCTG | 540 |
| GTCCTGGCTA | CGCCACTGGA | GGTTTTGGAA | GCAATGATGT | ACCGGCCTCC | AACCTTGCTA | 600 |
| TAATGCGGGG | TACACGGTTT | CCACTGCCGC | GCGTGCTTCT | GCTGCAGGAC | TGCCTCTAGG | 660 |
| TCACCTTCCA | ACGCGCCCTT | GAGCAAGTTC | GGATTCCGAG | AAGCAAATAT | CTCTCTCATC | 720 |
| GAAAGCCATT | TGCATCGTGA | GGTTCTCCGA | TCGTGGTGAA | AGTCAAAGTC | CGCGAGCGTC | 780 |
| AGTCGGTCAA | TTTCAAGCAG | CATCCAGTCG | TTCAATTTCA | GCAGCATCTG | CTTGCTCACG | 840 |
| GGCTGCCTTG | AGAGCATCCG | ATTCAGCGAC | CATGGTGGAA | TCCAATCCGC | ATCCACATCT | 900 |

| | | | | | | |
|---|---|---|---|---|---|---|
| CCGTTCTTCG | CTCCAAAACT | GCGGATCGAT | CCTGATATGC | TGTGAGGACG | CCGAACAGGG | 960 |
| ACGGCGCGAG | TTGATCTCCG | GGTCAAACCA | TATCAAGAGT | CCCTGGCTGT | TATATGTTCT | 1020 |
| GCGCTGCGCG | TGGATTCGGT | CGCATGTTCA | CGCGATTGTT | GGATAGTTCA | TCACTGTCGT | 1080 |
| TCAGGGAGAG | GATCACTCAG | CCACACTGTC | AGTGCACACG | GCACACCGAA | CCGGAAGTGG | 1140 |
| GACCGACAGT | ACCTGTGTAA | TGGTGGTGGT | TCGCGACAGT | TCAATATTCC | GTTGACTCTC | 1200 |
| AAACAAAGGA | ATTAAATATT | AAGCGCGCCC | CCCCTTAAAT | TCCTTAAAAA | ACTTAAATCC | 1260 |
| CAGGGAACTC | CCAATCAAAA | GAAACCGGGG | GTCCCTTTAA | CCAAATAATC | TGCACCCATG | 1320 |
| ATAAAATAGC | CAGGCGCATG | GTATTCTGCG | CCAGAAACAA | GTGTATCCGC | ATTAATGCCC | 1380 |
| CAAACCAGTA | CCCGGGAACC | TTCAAAGTCT | TACAAAGCTA | ACCAAATGCA | GGTCGAAATC | 1440 |
| CATCCAGACA | TCCGGACCAC | TACTTGTTTC | CCTAGAACCC | CCATTCATCA | CTCCGAATGG | 1500 |
| GTATGCTGAC | GATAATGAGT | CCTTATCGAC | AGGCTGATTC | TGCTCGAACC | CCACATTTGG | 1560 |
| AACGTACGCG | AGAACCTTCG | GCGAAGCTTT | TCGGTCGCGG | CCGTTATCTT | TTTAAGAGGA | 1620 |
| GAAATTTTAG | ATGAGCACGT | CCACCATCAG | GGTTGCCATT | GCCGGAGTCG | GAAATGCGCG | 1680 |
| ACCTCCCTCA | TTCAGCGTGT | GGAATATACC | GAAATGCGGA | ACCTCCGAAA | TGTCCCGGTT | 1740 |
| TGCTGCACTT | CAATTCGGTG | ATTACCACGT | TGCCGCATGA | TTCGTTGCCG | GTTCACGTCG | 1800 |
| ACGCCGAAAA | GTAGCAGGAA | TTCCCCGCAC | GGGGTTACAA | ACTGCATTAT | CAAATGCCAG | 1860 |
| TCCGAGCCGA | ATAACGGTGT | TGGCCGATTT | GAGGCTGGGT | TCATACGCGA | CATGACGGTC | 1920 |
| ACGCGGGCAT | GCCGTGTCAG | GGTTACGCGG | AAAACCCTTT | TTGAGCCCAC | CTCATGGTCC | 1980 |
| AGAGCGCAAT | TTCGGAAGCG | AAAATTCTAC | GCACAAGCGC | CATCGATTGC | AGTGCGCCTT | 2040 |
| TGTCAACGCT | CTCCCAGTAT | TCATCGCCTC | CGACCCTGAG | TGGGCTAAGA | AGTTAACTGA | 2100 |
| GGCTGGCATC | CCAATTGTTG | GCGATGACAT | CAAATCCCAG | ATCGGTGCAA | CCATCACCCA | 2160 |
| CCGTGTCCTC | GCACGCCTTT | TTGAAGAACG | TGTCGTTCGC | GTAGATCGCC | ACCTGCCGGA | 2220 |
| CCATTCTGGG | AACTGGACAG | CAGAATAT | | | | 2248 |

SEQ ID NO: 17:

| | | | | | | |
|---|---|---|---|---|---|---|
| GATCCAAAAA | GTCGCCGCAG | CTGACTGGAG | CTTCTGGGAA | GCCAAAGTCC | GCGCCCGCGA | 60 |
| CTACGCCCTG | GACGAAACCG | AACTGCGCAA | CTACTTCCCA | CTGAACCAAG | TACTCTGTGA | 120 |
| CGGCGTCTTC | TTCCCTGCTA | ACCCCCTCTA | CGGAATCACC | GTGGAACCAC | GCCCTGACCT | 180 |
| GCGCCGTTAC | CCCGACCGCG | TGGACGTCTG | GGAAGTCCTC | GATTCTGACG | CCTCCGGCAT | 240 |
| CCGCCACAAG | TGCGATCCGC | CCCTTCCCCG | TCGGCGACTG | GGTGATCTTG | CGGTGTCTAC | 300 |
| CTGGCGTCGA | CTGTCGAGTC | GTGGTCCCCA | TTGAACTTCT | TTCCGTGGTG | TTTATCTTTT | 360 |
| CATCACAAAC | AATCACGACG | GTATACCCAT | CGGAGACGAT | ATCGTGATCT | TTCTGTTACC | 420 |
| TGCGGAAGGT | AACATTAGTA | TTTCAACTCG | ACAGAGCCCA | TCCTGGAAGC | GTGTATGACG | 480 |
| ATTTCTTCAC | ACATTCTTTA | CAATGGCCTT | TCGTGCGATA | ATGCTAGGCA | TGCTTCGATG | 540 |
| GACTACAGCA | GGTGAATCCC | ACCGATC | | | | 567 |

SEQ ID NO: 18:

| | | | | | | |
|---|---|---|---|---|---|---|
| CTGGTTTTGG | CGGTAGGCAA | ACATGCCTTT | GAGGGTAGAT | GCCGGTAGGC | GGAGTGCTCA | 60 |
| CGGAATCTGT | GATGAGTGTG | CCGCCGTCTT | GGTCGATGAA | ATTGTGCACG | TGACGCCAGT | 120 |
| TTGCGAGGGC | CTTTACGGGG | GCGGTCAGAC | AGACGTCGGT | GAAGCGTGAA | CCATTCAAAA | 180 |
| ATCCCGATAA | ATCATGCCGC | GCCACCCATT | TAAGTCCCGC | AGGAAGGCTG | AAAATGGTGG | 240 |
| TGCCATCGGA | GAGGCGTTCT | GCCTGCGCAA | TGGGGTTAAG | GGGGACGAAT | GGCGGAGTCA | 300 |
| GACGTGTGAC | AGCGCCCTTA | CGGGTATGCC | AATCCCAGAC | CATTTCTCGG | GGAAAAGGAA | 360 |
| TAAAATGGCT | TGTGGTCAGA | CTCACAGGGG | CTTCTCCAAG | TCAGTGGATT | TATGAGGTCC | 420 |
| CAGTGGGTAC | ACACCCGGTG | TCCTACAACG | ATCAATTGTC | ACAGATTCGA | CTGGCATGCT | 480 |
| GTACCATCTG | CTTTAAGCAT | TTTGGTGTTT | CACTGTTGTT | AACAGTGTTT | CACCGTGGAG | 540 |
| CACTACCTAA | AGATCATAGT | CAGCATCTTG | GGGTGAATGT | GACACGGTAC | GCTATAGTGT | 600 |
| CAGACAACAA | CCAGGAAACT | GGTCGTTGCA | GAGTTTTTGC | AAAATTGGAC | ATCCTTTAAC | 660 |
| GGACCGCACA | GAGAGGCGGG | AAGGAGGTCA | CGATGAGCGA | ACGTAATAGT | GCTGTACTAG | 720 |
| AACTCCTCAA | TGAGGACGAC | GTCAGCCGTA | CCATCGACGA | CATCGCCACA | CAGATTATTG | 780 |
| AGAAAACCGC | GCTTGATTCC | AAATACGCCG | ATCGCGTCAT | GTTGTTAGGC | ATTCCTTCAG | 840 |
| GTGGAGTCCC | GCTGGCCCGA | AGGCTTGCTG | AAAAGATCGA | AGAATTTTCC | GGCGTTTCGG | 900 |
| TAGATACCGG | CGCTGTTGAT | ATCACCTTGT | ACAGGGATGA | TCTTCGAAAC | AAACCGCACC | 960 |
| GCCCACTGCA | GCCCACCTCT | ATTCCGCCAG | GTGGTATCGA | TAACACCACC | GTGATTTTGG | 1020 |
| TGGATGATGT | GCTGTTTTCC | GGTCGTACTA | TNCGCGCTGC | ACTTGATGCA | TTGCGCGACG | 1080 |
| TTGGACGCCC | AAACTATATC | CAATTAG | | | | 1107 |

SEQ ID NO: 19:

| | | | | | | |
|---|---|---|---|---|---|---|
| GGATCCGGTA | ACCGTTTTTA | TCAGGCTCTG | GGAGGCAGAA | TAAATGATCA | TATCGTCAAT | 60 |
| TATTACCTCC | ACGGGGAGAG | CCTGAGCAAA | CTGGCCTCAG | GCATTTAAGA | AGCACACGGT | 120 |
| CACACTGCTT | CCGGTAGTCA | ATAAACCGGT | AAACCAGCAA | TAGACATAAG | CGGCTATTTA | 180 |
| ACGACCCTGC | CCTGAACCGA | CGACCGGGTC | GAATTTGCTT | TCGATATCTG | CCATTCATCC | 240 |
| GCTTATTATC | ACTTATTCAG | GCGTAGAACC | AGGCGTTTAA | GGGCACCAAT | AACTGCCTTA | 300 |
| AAAAAATTAC | GCCCGCCCTG | CCACTCATCG | CAGTACTGTT | GTAATTCATT | AAGCATTCTG | 360 |
| CCGACATGGG | AGGCCATCAC | AACGGGCAT | GATGAACCTG | AATCGCCAGC | GGGCATCAGC | 420 |
| ACTTGGTCGC | CTTGCGTATA | AATATTTCCC | CCTGGTGGAA | AACGGGGCCG | AAGAGGTTGT | 480 |
| CCCATATTTG | GCCACGGTTT | AAATCAAAAT | TGGTGGAACT | CACCCTGCGT | TTGGCTAGCG | 540 |
| ATCCGCGTTG | ACATCTGCAG | GCGGGAAATT | GAAAAGGCCG | GATAAAACTG | GTGCCTATTT | 600 |
| CCCTTAACGG | TCTTTAAAAA | AGGCCCGTAA | TACCCAACCG | AAACCGTCTG | GTTATAGCAA | 660 |
| CACCGGACAA | CTGGACGGA | AATGCCCTCC | AAATGCCCT | CTACGATCCC | CAATTGGGGA | 720 |
| TACATCCAAC | GGTGGTATAA | CCCAGTGATT | TTTTTTCCCC | CCATTTTTAG | CTTCCTTTAG | 780 |
| CTCCTGAAAA | TCTCGATAAC | TCAAAAAAAT | ACGCCCGGCA | GTGATCTTAT | TTCATTATGG | 840 |
| TGAAAGTTGG | AACCTCTTAC | GTGCCGATCA | ACGTCTCATC | TTCGCCAAAA | GTTGGCCCAG | 900 |
| GGCTTCCCCG | TATCAACGGA | GACACCAGGA | TTATTTATTC | TGCGAAGTGA | TCTTCCGTCA | 960 |
| CAGGTATTTA | TTCGGCGCAA | AGTGCGTCGG | GTGATGCTGC | CAACTTACCG | ATTTAGTGTA | 1020 |
| TGATGGCGTT | CTTGAGGTGC | TCCAGTCCCT | TCTGTTTCTA | TCAGCTGTCC | CTCCTGTTCA | 1080 |
| GCTATTGACG | CGGTGGTGCG | TAACGGAAAA | GCACCGCCGG | ACATCACCGG | ATCTCAAGAA | 1140 |
| GACCTTTGAA | ACTGTCCAACG | GATCCCCAGG | GGCAGGCGGT | ACACCGCCCG | CTCGGACGTA | 1200 |
| TCGGAGTTTC | CCGCGTTTCC | GATGTCCGTC | AGGGAAAGCG | CTTCGACCTC | GAGGTAGATG | 1260 |
| ATTCCGTCAC | CGAAGCTGAC | CTAAAGAAAA | TTGCTGAAAC | CCTCCTCCCA | AACACCGTCA | 1320 |

| | | | | | | |
|---|---|---|---|---|---|---|
| TCGAAGACTT | CGATGTGGTG | GGAGTTGAGG | TCGCGAAGTG | AGCGCCAAAA | TCGGTGTCAT | 1380 |
| TACCTTCCCA | GGCACCCTTG | ACGATGTAGA | TGCAGCACGC | GCTGTTCCCA | TCGCAGGTGC | 1440 |
| AGAAGTAATC | AGCCTGTGGC | ACGCTGACGA | GGATCTCAAG | GGCGTCGACG | CAGTTGTCGT | 1500 |
| TCCCGGTGGA | TTCCCCCTAC | GGCGATTACC | TGCGCACCGG | TGCAATCTCT | CCACTGGCGC | 1560 |
| CAGTAATGCA | GTCCGTGATT | GAGCAGGCCG | GTAAGGGTAT | GCCAGTCTTG | GGCATTTGCA | 1620 |
| ACGGCTTCCA | GATCCTCACC | GANGCACGCC | TGCTTCCAGG | CGCGCTGACC | CGCAACAAGG | 1680 |
| GTCTGCACTT | TCACCGTGTA | GACGCACACC | TCGTTGTAGA | GAACAACACC | ACTGCATGGA | 1740 |
| CCAACACTCT | GGAAAAGGGG | CAGCAGATCC | TTATTCCTGC | AAAGCACGGT | GAAGGTCGCT | 1800 |
| TCCAGGCAGA | CGGCAGAGAC | CATTCGCCCA | GCTTCGAGGG | TGAAGCCCCC | GTGGTGTTCC | 1860 |
| GTTACAACGA | TAACTTCAAC | GGTTTCCGTA | GACCTACCAA | GCCGGTATCA | CTAATGAAAC | 1920 |
| TGGTCGCATC | GTCGGCCTCA | TGCCGCACCC | GGAACATGCC | GTCGAAAAGC | TAACCGGCCC | 1980 |
| ATCTATTGAT | CCCCTGGAGC | TGTTCCCGTC | CGCCGCTGGC | ACCATCGCGG | CTTAAGAGGA | 2040 |
| GTCAAAATAT | GAGCACTCTT | GTCAATGACA | CCGTCGAGAG | CAATCAAGAC | CCCTGAGACC | 2100 |
| AATTCTGGGA | TCTGA | | | | | 2115 |

SEQ ID NO: 20:

| | | | | | | |
|---|---|---|---|---|---|---|
| ATATTCTGCT | GTCCAGCCCC | CAGAATGGTC | CGCCAGGTGG | CGATCTACGC | GAACGACACG | 60 |
| TTCCTCAAAA | AGGCGTGCGA | GGACACGGTG | GGTGATGGTT | GCACCGATCT | GGGATTTGAT | 120 |
| GTCACCGCCA | ACAATTGGGA | TCCCAGCCTC | AGTTAACTCC | TTAGCCCACT | CAGGGTCGGA | 180 |
| GGCGATGAAC | ACTGGGAGAG | CGTTGACAAA | GGCGCACTGC | AATCGATGGC | GCTTGTGCGT | 240 |
| AGAATTCCCG | CCTCCGAAAT | TGCGCTCTGG | ACCATGAGGT | GGGCTCAAAA | AGGGTTTTCC | 300 |
| GCATAACCCT | GACACGCCAT | GCCCGCGTGA | CCGTCATGTC | CCGTATGAAC | CCAGCCTCAA | 360 |
| ACCGCCAAC | ACCGTTATTC | GGCTCGGACT | GGCATTTGAT | AATGCAGTTT | GTAACCCCGT | 420 |
| GCGGGGAATT | CCCGCCACTT | TTCGGCGTCG | ACGTGAACCG | GCAACGAATC | ATGCGCCAAC | 480 |
| GTGGTAATCA | CCGAATTGAA | GTGCAGCAAA | CCGGGACACT | TCGGAGGTTC | CGCATTTCGG | 540 |
| TATATTCCAC | ACCCTGAATG | AGGGAGGTCG | CGCACTTCCG | ACTCCCCCAA | TGGCAACCCT | 600 |
| GATGGTGGAC | GTGCTCACCC | AAAATTTCTC | CTCTCAAAAA | GATAACGGCC | GCGACCGAAA | 660 |
| AGCTTCGCCG | AAGGTCCTCG | CGTACGTTCC | AAATGTGGGG | TTCCAGCAGA | ATCAGCCTGT | 720 |
| CGATAAGGAC | TCATTATCGT | CAGCACACCC | ATTCGGAGTG | ATGAATGCGG | GTTCTAGGGA | 780 |
| AACAAGTAGT | GGTCCGGATG | TCCGGATGGA | CTTCGACCTG | CATTTGGTTA | GCTTTGTAAG | 840 |
| ACTTTGAAGC | CCCCCCCGTA | CTGGTTTGGG | GCATTAAATGC | GGATACACTT | GTTTCTGGCC | 900 |
| CAGAACACCA | CGCGCCTGGC | TATTTTATCA | TGGGTGCAGA | TTATTTCGTC | AAAGGGACCC | 960 |
| CCGGTTTCTT | TTGATTGGGA | GTTCCCTGGG | ATTTAAGTTT | TTTAAGGAAT | TTAAGGGGGG | 1020 |
| GCGCGCTTAA | TATTTAATCC | CTTTGTTTGA | GAGTCAACGG | AATATTGAAG | CTGCGCGAAC | 1080 |
| CACCACCATT | ACACAGGTAC | TGTCCGTCCC | ACTTCCGGTT | CGGTGTACCG | TGTGCACTGA | 1140 |
| CAGTGTGGCT | GAGTGATCCT | CTCCCTGAAC | GACAGTGATG | AACTATCCAA | CAATCGCGTG | 1200 |
| AACATGCGAC | CGAATCCACG | CGCAGCGCAG | AACATATAAC | AGCCAGGGAC | TCTTGATATG | 1260 |
| GTTTGACCCG | GAGATCALCT | CGCGCCGTCC | CTGTTCGGCG | TCCTCACAGC | ATATCAGGAT | 1320 |
| CGATCCGCAG | TTTTGGAGCG | AAGAACCGAG | ATGTGGATGC | GGATTGGATT | CCACCATGGT | 1380 |
| CGCTGAATCG | GATGCTCTCA | AGGCAGCCCG | TGAGCAAGCA | GATGCTCCTG | AAATTGAACG | 1440 |
| ACTGGATGCT | GCTTGAAATT | GACCGACTGA | CGCTCCCCGA | CTTTGACTTT | CACCACGATC | 1500 |
| GCAGAACCTC | ACGATGCAAA | TGGCTTTCGA | TGAGAGAGAT | ATTTGCTTCT | CGGAATCCGA | 1560 |
| ACTTGCTCAA | CCCCGCGTTG | GAAGGTGACC | TAGAGGCAGT | CCTGCACGAG | AAGCACGCGC | 1620 |
| CGCAGTGGAA | ACCGTGTACC | CCGCATTATA | GCAAGGTTGC | AGGCCGGTAC | ATCATTGCTT | 1680 |
| CCAAAACCTC | CAGTCCCCTA | GCCAGGACCA | GCCTAACTTG | CAGTCCTACA | CCGTTTTGGA | 1740 |
| GGAAACTGAG | CGACGCGTTG | CATCCACCAC | TGAAGGTCTA | GAAAAAGCCG | AGCGGATCTA | 1800 |
| CATTGATTCA | CTCGGAAAAG | TTGACTCAGA | CTAGCCGCTG | CACAGGCGCC | GTGATGAGCC | 1860 |
| CAATAGCACA | CAAGCGCAAA | CTTGGCTCGA | GACGGGATTT | TCACCAACAC | CATTGGAGAA | 1920 |
| AATAAGCGCA | TTATCCACTT | TAGGTTGCAT | CAGTAGATAT | TAAGCGCCAC | CAGATCACGT | 1980 |
| CCCAGTTCGG | ATGATATCAA | CACACCACCG | TCGATCCCCA | TACTCAGGCA | TTGTTCATCC | 2040 |
| GTGGCAGGCA | GCCCAAGGTC | AACCAGCAGC | CGGCGCACTG | TTGAGTGTTG | CTGATGATTC | 2100 |
| CGAACTGAAG | ATCACCGCGA | ATGTAAAAGA | AACAGAGATC | AGCAACGTCA | CCATCGGATC | 2160 |
| CCGTGTCACC | TTCACTACCC | CATCGACCGG | AACCAAAGAA | TTGTGGGCCG | TAT | 2213 |

The controllable promoter DNA fragment of the invention including the above nucleotide sequences and DNA fragment may not necessarily be obtained from naturally occurring coryneform bacteria chromosomal DNA, but may also be synthesized by a known DNA synthesizer, such as an Applied Biosystems model 380A DNA Synthesizer.

Some nucleotides of controllable promoter DNA fragments according to the invention obtained from chromosomal DNA of *Brevibacterium flavum* MJ-233 (FERM BP-1497) may be replaced with other nucleotides or deleted, or other nucleotides may be inserted into the sequences of the DNA fragments, as long as such nucleotide sequence changes will not substantially reduce the promoter control capability of the DNA fragments. Such DNA fragment derivatives are included in the controllable promoter DNA fragment of the present invention.

A gene of interest can be expressed at a high rate and efficiency in coryneform bacteria cells by using a coryneform bacteria promoter DNA fragment according to the invention, more specifically, by ligating the gene to the downstream end of the promoter DNA fragment, inserting the ligated fragments into plasmid vectors which can replicate by themselves in coryneform bacteria cells, and then introducing the plasmid vectors into coryneform bacteria cells. The gene of interest to be ligated to the downstream end of the promoter DNA fragment of the invention may be a variety of genes including microorganism genes, animal genes, plant genes and synthetic genes. Examples of gene expression products include: enzymes involved in the biosynthesis and metabolism of bio-substances, such as amino acids, organic acids, vitamins, and lipids; and enzymes involved in the biosynthesis and metabolism of bioactive substances, such as proteins, fats and oils, and antibiotics. A plasmid vector used to carry a promoter DNA fragment according to the present invention may be any type that has a plasmid replication origin DNA region functional in coryneform bacteria cells. Examples of such plasmid vectors are:

(1) pAM330 [Agricultural and Biological Chemistry., 48. 2901, (1986)]

(2) pCG4 [Journal of Bacteriology., 159, 306, (1984)]

(3) pSR1 [Journal of Bacteriology., 162, 591, (1985)]

(4) pBY503 [Journal of Industrial Microbiology, 5, 159, (1990)]

(5) pBL1 [Journal of Bacteriology., 162, 463, (1985)]

(6) pHM1519 [Gene., 39, 281, (1985)]

(7) pCG1 [Molecular and General Genetics., 196, 175, (1984)]

(8) pCG100 [Journal of General Microbiology., 137, 2093, (1991)]

Further, plasmid vectors having plasmid replication origin DNA region functional in coryneform bacteria cells which are obtained from any one or more of the above-listed plasmid vectors can also be suitably used.

The present invention will be further described in detail with reference to Examples hereinafter. The following Examples are intended to be illustrative, and should not be construed as limiting the claimed invention.

EXAMPLES

Example 1

Construction of Promoter Probe Shuttle Vector pPROBE17

Figure 2:
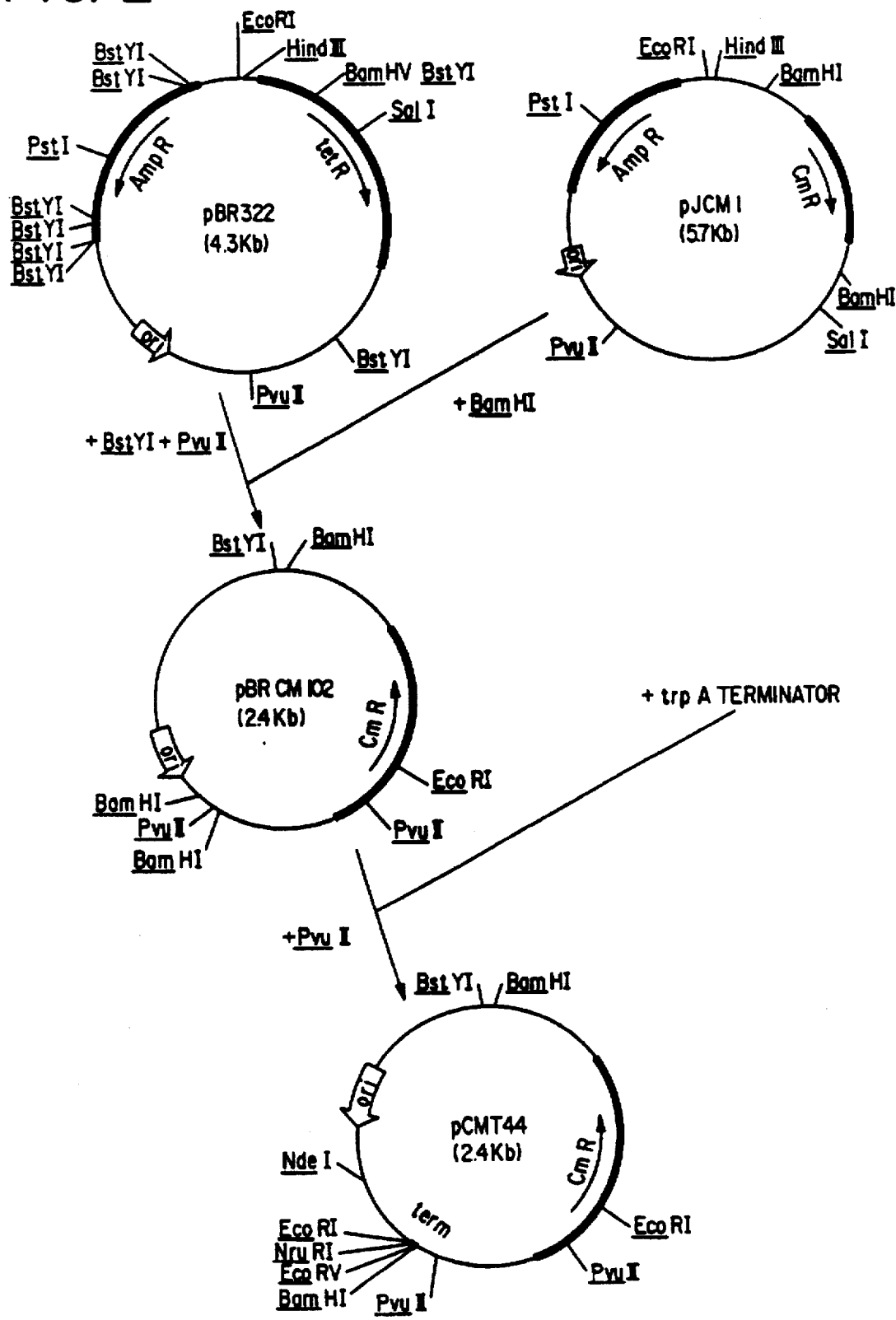
FIG. 2 shows the construction of two specific vectors, namely, pBRCM102 and pCMT44, constructed in accordance with this invention.
Figure 3:
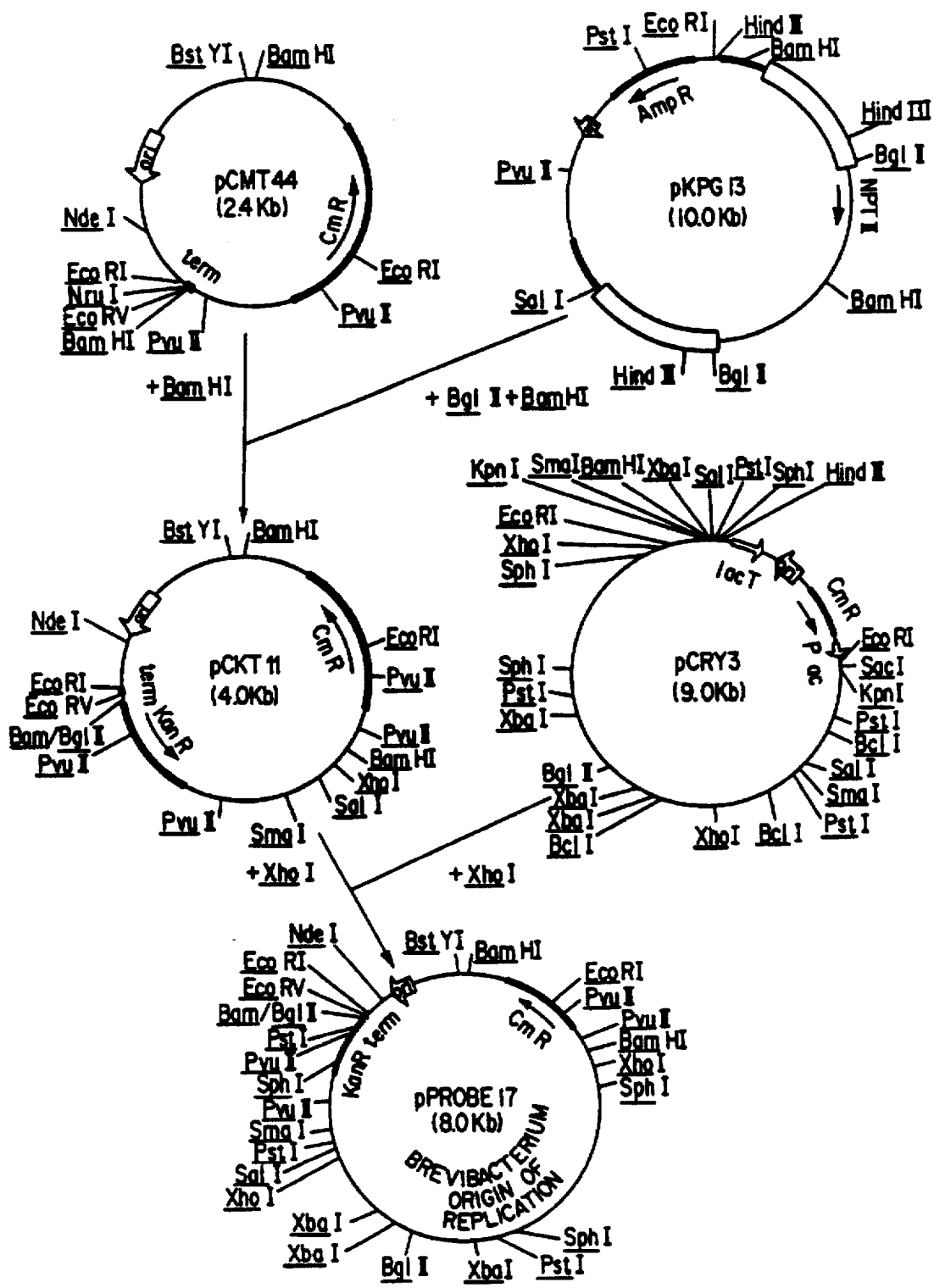
FIG. 3 shows the construction of two specific vectors, namely, pCKT11 and pPROBE17, constructed in accordance with this invention.
Figure 4:
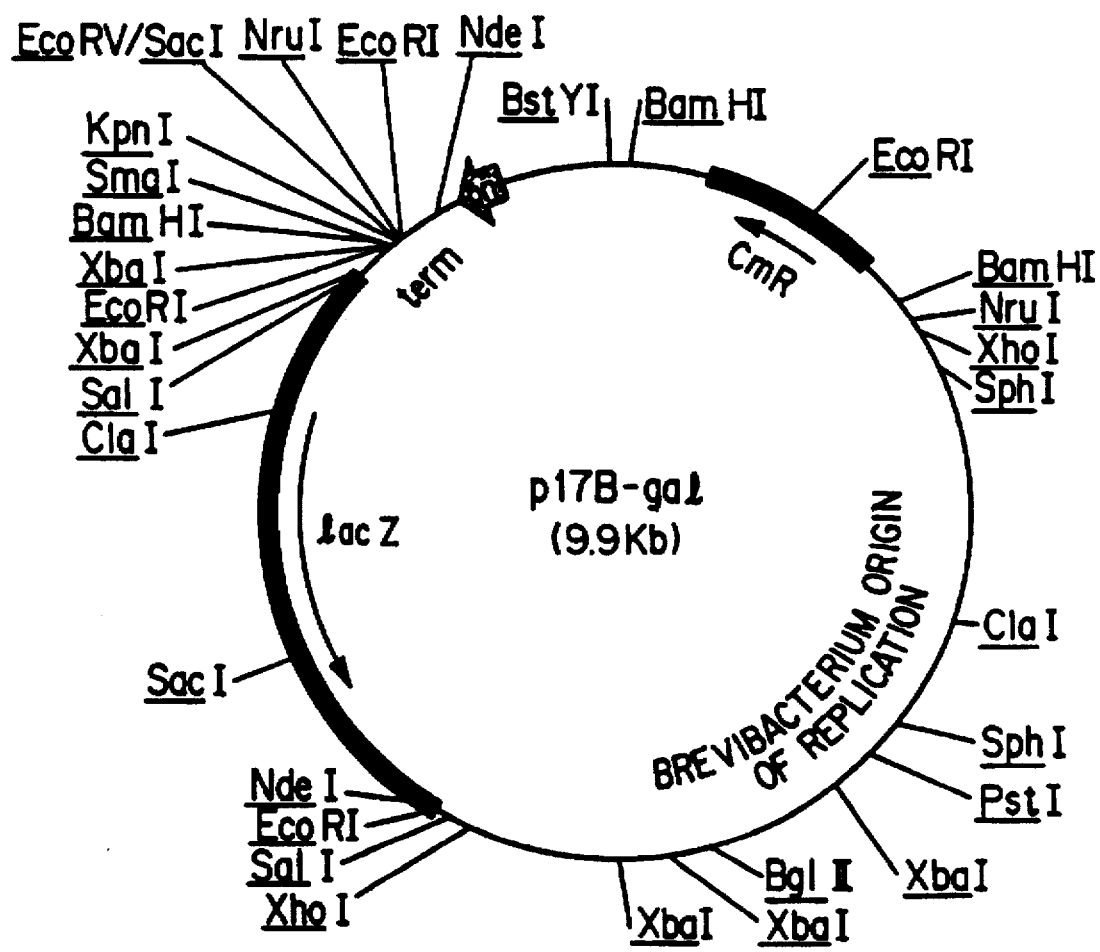
FIG. 4 shows a specific novel plasmid vector 17Bgal useful for detecting promoter DNA fragments in coryneform bacteria.

Promoter probe shuttle vector pPROBE17 was constructed by the scheme illustrated in FIGS. 2 and 3.

First, a plasmid, named as pBRCM102, as shown in FIG. 2 was constructed as follows:

10 µg of *Escherichia coli* plasmid pBR322 DNA was digested by incubating with the restriction enzymes PvuII and BstYI at 37° C. for one hour, followed by separating the resultant fragments by agarose-gel electrophoresis. A 1.1 Kb DNA fragment including a DNA region (ORI) involved in the plasmid replication in *Escherichia coli* cells was eluted from a gel section containing the fragment, and then purified, thus obtaining 1.5 µg of DNA.

The thus-obtained DNA fragment lacked the RNAI promoter region, that is, a pBR322 replication control element. To provide promoters for the DNA fragments, a synthetic DNA fragment having promoter function was synthesized as follows. Single-strand DNA fragments (1) and (2) of the following DNA fragment (containing a restriction enzyme BamHI recognition site) were separately synthesized by using an Applied Biosystems model 380A DNA synthesizer.

After the region c DNA fragment and the region a DNA fragment were separately incubated at 60° C. for 10 minutes, they were mixed and then ligated by incubating the mixture with the T4 DNA ligase at 16° C. for 24 hours in the presence of ATP and dithiothreitol.

The ligation produces were introduced into *Escherichia coli* HB101 (Takara Shuzo Co., Ltd.) by the calcium chloride method (Journal of Molecular Biology, 53, 159 (1970)). The cells were then plated on a selective agar plate (prepared by dissolving 10 g of trytone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by an usual method (Nucleic Acids Research, 9, 1989 (1981)), and digested with various restriction enzymes. The restriction fragments were electrophoresed on a agarose gel, thus confirming that a plasmid pBRCM102 as shown in FIG. 2 was obtained.

Secondly, a plasmid, named as pCMT44, as shown in FIG. 2 was constructed using the plasmid pBRCM102 as follows:

5 µg of the plasmid pBRCM102 DNA was partially digested by incubating with the restriction enzyme PvuII at 37° C. for 5 minutes.

Separately, single-strand DNA fragments of the following DNA fragment with the following sequence, that is, the transcription terminating element trpA terminator (region e, hereinafter referred to as "the term") of the *Escherichia coli* tryptophan operon, were separately synthesized by using an Applied Biosystems model 380A DNA synthesizer.

(3) 5'AATTCTCGCGATAATTAATTAATAGC-
C C G C C T A A T -
GAGCGGGCTTTTTTTTGATATCAATT 3' (SEQ ID NO:21)

(4) 3'TTAAGAGCGCTATTAATTAAT-
TATCGGGCGGATTACTCGC-
CCGAAAAAAAACTATAGTTAA 5'

The single-strand DNA fragments were mixed and then annealed by incubating the mixture at 50° C. for 5 hours, thus obtaining 5 µg of double-strand DNA having the sequence shown above.

5 µg of the synthesized DNA and 5 µg of the plasmid DNA partially digested with restriction enzyme PvuII were mixed and then ligated by incubating the mixture with the DNA ligase at 16° C. for 24 hours in the presence of ATP and dithiothreitol.

| (1) 5' GATCTCAAGA | AGATCCTTTG | ATCTTTTCTA | CGGATCCCAG 3' (SEQ ID: 24) |
|---|---|---|---|
| (2) 3' AGTTCT | TCTAGGAAAC | TAGAAAAGAT | GCCTAGGGTC 5' |

The single-strand DNA fragments (1) and (2) were mixed and then annealed by incubating the mixture at 50° C. for 5 hours, thus obtaining 5 µg of double-strand DNA as shown above.

Then, 5 µg of the double-strand DNA and 1.5 µg of the 1.1 Kb DNA were mixed and then ligated by incubating the mixture with the T4 DNA ligase at 16° C. for 24 hours in the presence of ATP and dithiothreitol. The ligation product was digested by incubating with the restriction enzyme BamHI at 37° C. for one hour, thus obtaining a DNA fragment (the region a) having a BamHI site at the 5' end.

Separately, 1 g of plasmid pJCM1 DNA having a chloramphenicol resistance gene of the transposon Tn9 was digested by incubating with the restriction enzyme BamHI at 37° C. for one hour, thus obtaining a region c DNA fragment.

The ligation products were introduced into *Escherichia coli* HB101 (Takara Shuzo Co., Ltd.) by the sodium calcium method (Journal of Molecular Biology, 53, 149 (1970)), followed by plating the cells on a selective agar plate (prepared by dissolving 10 g of tryptone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by an usual method (Nucleic Acids Research, 9, 1989 (1981)), and digested with various restriction enzymes. The restriction fragments were electrophoresed on an agarose gel, thus confirming that a plasmid pCMT44 was obtained. As shown in FIG. 2, the plasmid pCMT44 contains the transcription terminating element trpA terminator (region e) at the PvuII site in the downstream from the replication-related DNA region (ORI), that is, in a region closer to the 3' end of the ORI region.

Third, a plasmid, named as pCKT11, as shown in FIG. 3 was constructed using the plasmid pCMT44 as follows:

10 μg of plasmid pKPG13 DNA was digested by incubation with the restriction enzymes BglII and BamHI at 37° C. for one hour, so that the desired restriction fragment would not include the promoter of the kanamycin resistance gene. The restriction fragments were electrophoresed on an agarose gel, followed by cutting out a gel section exclusively containing a 1.5 Kb kanamycin resistance structural gene fragment. The DNA fragment was eluted from the gel section and purified, yielding 1 μg (region d, i.e., the reporter gene).

1 μg of the thus-obtained DNA was mixed with the restriction fragments obtained by partially digesting 1 μg of the plasmid pCMT44 DNA with the restriction enzyme BamHI at 37° C. for 5 minutes. The mixture as incubated at 16° C. for 24 hours in the presence of the T4 DNA ligase, ATP and dithiothreitol to ligate the DNA fragments.

The ligation products were introduced into *Escherichia coli* HB101 (Takara Shuzo Co., Ltd.) by the sodium calcium method (Journal of Molecular Biology, 53, 149 (1970)), followed by plating the cells on a selective agar plate (prepared by dissolving 10 g of tryprone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by a known usual method (Nucleic Acids Research, 9, 1989 (1981)), and digested with various restriction enzymes. The restriction fragments were electrophoresed on an agarose gel, thus confirming that a plasmid pCMT11 as shown in FIG. 3 was obtained.

Finally, a plasmid, named as pPROBE17, as shown in FIG. 3 was constructed using the plasmid pCKT11 as follows:

Plasmid DNA was extracted from *Brevibacterium flavum* MJ233 GE102 (FERM BP-2513) containing the plasmid pCRY3 capable of replication in coryneform bacteria cells, by an usual method (Nucleic Acids Research, 9, 1989 (1981)). 10 μg of the plasmid DNA was incubated with the restriction enzyme XhoI at 37° C. for one hour. The resultant restriction fragments were electrophoresed on an agarose gel, followed by cutting out a gal section containing a 4.0 Kb DNA fragment capable of replication in coryneform bacteria cells. The DNA was eluted from the gel section and purified, yielding 2.5 μg (region b).

2.5 μg of the DNA fragment and 1 μg of the plasmid pCKT11 DNA were separately incubated with the restriction enzyme XhoI at 37° C. for one hours. After the resultant restriction fragments were mixed and incubated at 65° C. for 10 minutes, the mixture was incubated at 16° C. for 24 hours in the presence of the T4 DNA ligase, ATP and dithiothreitol to ligate the fragments.

The ligation products were introduced into *Escherichia coli* HB101 (Takara Shuzo Co., Ltd.) by the sodium calcium method (Journal of Molecular Biology, 53, 149 (1970)), followed by plating the cells on a selective agar plate (prepared by dissolving 10 g of tryptone, 5 g of yeast extracts, 5 g of sodium chloride and 16 g of agar into distilled water to obtain 1 liter) containing 50 mg/l of chloramphenicol.

Then, plasmid DNA was extracted from the colonies on the selective agar plate by a known method (Nucleic Acids Research, 9, 1989 (1981)), and digested with various restriction enzymes. The restriction fragments were electrophoresed on a agarose gel, thus confirming that a plasmid pPROBE17 as shown in FIG. 3 was obtained.

The plasmid pPROBE17 consists essentially of:

a) a plasmid replication origin region functional in *Escherichia coli*, b) a plasmid replication origin region functional in coryneform bacteria, c) a chloramphenicol resistance gene, d) a kanamycin resistance gene lacking its own promoter, and e) a transcription terminating element trpA terminator present in the upstream of the kanamycin resistance gene.

Example 2

Introduction of Plasmid pPROBE17 into Coryneform Bacteria Cells *Brevibacterium flavum* MJ-233 (FERM BP-1497) was cultured in A medium (prepared by dissolving 2 g of urea, 7 g of $(NH_4)_2SO_4$, 0.5 g of $K_2HPO_4$, 0.5 g of $KH_2PO_4$, 0.5 g of $MgSO_4$, 6 mg of $FeSO_4 \cdot 7H_2O$, 6 mg of $MnSO_4 \cdot 4\text{-}6H_2O$, 2.5 g of yeast extracts, 5 g of casamino acid, 200 μg of biotin, 200 μg of thiamin hydrochloride and 20 g of glucose into distilled water to obtained 1 liter) at 33° C. until the logarithmic metaphase, followed by adding penicillin G to the medium so as to obtain a concentration of 1 unit/ml. After being further cultured for 2 hours, the cells were collected by centrifugation. The obtained bacterial cells were washed with sterilized water and a pulse buffer (272 mM sucrose, 7 mM $KH_2PO_4$, 1 mM $MgCl_2$, pH 7.4) followed by centrifugation. The washed bacterial cells were suspended in 2 ml of the pulse buffer. 120 μl of the bacterial cells suspension were mixed with 5 μg of the plasmid pPROBE17 DNA obtained in Example 1, and the mixture was allowed to stand in ice for 10 minutes. After the mixture was pulsed by a Gene Pulser (BioLad) at 1950 V and 25 μFD, the mixture was allowed to stand in ice for 10 minutes. The entire mixture was suspended in 3 ml of A medium, followed by incubation at 33° C. for one hour. The mixture was plated on an A-medium agar plate (the A medium-agar proportion being 1 liter to 16 g) containing 3 g/ml (final concentration) of chloramphenicol, and incubated at 33° C. for 2 days. Plasmid DNA was extracted from the colonies of chloramphenicol resistant strains by a known usual method (Nucleic Acids Research, 1989 (1981)), and digested with various restriction enzymes. The restriction fragments were electrophoresed on a agarose gel, thus confirming that the extracted plasmid was the plasmid pPROBE17 constructed in Example 1 as shown in FIG. 3.

Because the plasmid pPROBE17 does not have a promoter region of the kanamycin resistance gene, the coryneform bacteria cells transformed with only the plasmid are expected to exhibit no resistance to kanamycin.

To confirm this, such coryneform bacteria cells were plated on an A-medium agar plate as described above and incubated at 33° C. for 4 days. As a result, no colony was observed on the plate. Thus, it was proven that the transcription terminating element trpA terminator present in the upstream from the kanamycin resistance gene on the plasmid pPROBE17 is effective. In other words, there is no expression of the kanamycin gene caused by read-through on the plasmid pPROBE17 in coryneform bacteria cells.

Example 3

Strength of *Escherichia coli* tac Promoter in Coryneform Bacteria Cells tac Promoters were isolated from the plasmid pDR540 (Pharmacia Co., Ltd.) as follows:

25 µg of the plasmid pDR540 DNA was incubated with the restriction enzymes HindIII and BamHI at 37° C. for one hour. The resultant restriction fragments were electrophoresed on an agarose gel, followed by cutting out a gel section containing a DNA fragment containing a 96 bp tac promoter. The DNA was eluted from the gel section and purified, yielding 0.5 µg. 2.5 µg of the obtained DNA fragments were incubated with the S1 nuclease at 37° C. for one hour to blunt the both ends of the fragments. Separately, 0.5 µg of the plasmid pPROBE17 DNA was incubated with the restriction enzyme EcoRV at 37° C. for one hour. The ends of the resultant restriction fragments were blunted in a similar manner.

These blunt-end DNA fragments were incubated at 65° C. for 10 minutes, and then these DNA fragments were ligated by incubation at 16° C. for 24 hours in the presence of the DNA ligase, ATP and dithiothreitol.

The ligation products were introduced into Brevibacterium flavum MJ-233 (FERM BP-1497) by the sodium calcium method (Journal of Molecular Biology, 53, 149 (1970)). The transformants were selected by plating the resultant bacterial cells on an A-medium agar plate containing 30 µg/ml (final concentration) of kanamycin and then incubating at 33° C. for 2 days.

Then, plasmid DNA was extracted from the kanamycin resistant strain colonies by a known method (Nucleic Acids Research, 9, 1989 (1981)), and digested with various restriction enzymes. The restriction fragments were electrophoresed on a agarose gel, thus confirming that a 270 bp DNA fragment containing a tac promoter had been inserted into the plasmid pPROBE17 at the EcoRV site.

To determine the strength of the tac promoter in coryneform bacteria cells, the thus-obtained kanamycin resistant strain was plated on A-medium agar plates (as described above) containing different concentrations of kanamycin and incubated at 33° C. for 4 days. As a result, the strain was able to grow on an A-medium agar plate containing 100 µg/ml (final concentration) of kanamycin, but failed to grow on an A-medium agar plate containing 500 µg/ml of kanamycin.

Example 4

Preparation of Coryneform Bacteria Chromosomal DNA

Brevibacterium flavum MJ-233 (FERM BP-1497) was cultured in A medium at 33° C. until the logarithmic phase, followed by centrifugation to collect the cells. The obtained bacterial cells were suspended in 15 ml of a lysozyme reaction mixture (10 mg/ml lysozyme, 10 mM NaCl, 20 mM Tris-HCl (pH 8.0), 1 mM EDTA-2Na). Subsequently, the proteinase K was added to the lysozyme reaction mixture to a final concentration of 100 µg/ml, followed by incubation at 37° C. for one hour. Then, sodium dodecyl sulfate was added to the mixture to a final concentration of 0.5 %, followed by incubation at 50° C. for one hour to promote cell lysis. The lysate was added to an equal volume of a phenol-chloroform (1:1, by v/v) solution, and moderately shaken at room temperature for 10 minutes. The entire mixture was then centrifuged, and a supernatant fraction was recovered. After adding sodium acetate to the recovered supernatant fraction to a concentration of 0.3M, ethanol was added to the mixture (the ethanol-mixture volume ratio being 2:1), followed by centrifugation. The precipitated DNA was washed with 70 % ethanol and dried. The dried DNA was dissolved into 5 ml of a solution containing 10 mM Tris-HCl (pH 7.5) and 1 mM EDTA-2Na, thus obtaining a coryneform bacteria chromosomal DNA solution.

Example 5

Isolation of Promoter DNA Fragment Having Greater Promoter Strength Than tac Promoter from Coryneform Bacteria Chromosomal DNA 20 µg of the coryneform bacteria chromosomal DNA prepared in Example 4 was completely digested by incubation with the 4-base-sequence recognizing restriction enzymes AluI and HaeIII at 37° C. for 10 hours. Separately, 10 µg of the plasmid pPROBE17 DNA prepared in Example 2 was digested by incubation with the restriction enzyme EcoRV at 37° C. for one hour. After these resultant solutions were incubated at 65° C. for 10 minutes, they were mixed and then incubated at 16° C. for 24 hours in the presence of the T4 DNA ligase, ATP and dithiothreitol to ligate the DNA fragments.

The ligation products were introduced into Brevibacterium flavum HJ-233 (FERM BP-1497) by the method described in Example 2. The transformants were selected by plating the resultant bacterial cells on A-medium agar plates containing various concentrations of kanamycin: 500, 750, 1000, 1500 µg/ml (final concentrations) and then incubating at 33° C. for 3 days. As a result, twelve transformants capable of growing on media containing 500 µg/ml or more of kanamycin were obtained, as shown in Table 1. These transformants and their plasmids are named as follows:

| No | Bacteria strain | | Plasmid | |
|---|---|---|---|---|
| (1) | Brevibacterium flavum | MJ233 | Km5001 | pPROBE17 | Km5001 |
| (2) | Brevibacterium flavum | MJ233 | Km5002 | pPROBE17 | Km5002 |
| (3) | Brevibacterium flavum | MJ233 | Km5003 | pPROBE17 | Km5003 |
| (4) | Brevibacterium flavum | MJ233 | Km5004 | pPROBE17 | Km5004 |
| (5) | Brevibacterium flavum | MJ233 | Km5005 | pPROBE17 | Km5005 |
| (6) | Brevibacterium flavum | MJ233 | Km5006 | pPROBE17 | Km5006 |
| (7) | Brevibacterium flavum | MJ233 | Km5007 | pPROBE17 | Km5007 |
| (8) | Brevibacterium flavum | MJ233 | Km5008 | pPROBE17 | Km5008 |
| (9) | Brevibacterium flavum | MJ233 | Km5009 | pPROBE17 | Km5009 |
| (10) | Brevibacterium flavum | MJ233 | Km5010 | pPROBE17 | Km5010 |
| (11) | Brevibacterium flavum | MJ233 | Km5011 | pPROBE17 | Km5011 |
| (12) | Brevibacterium flavum | MJ233 | Km5012 | pPROBE17 | Km5012 |

Plasmid DNA was extracted from each of the twelve kanamycin resistant strains by a known method (Nucleic Acids Research, 9, 2898, (1981)).

The extracted plasmid DNA was again introduced into Brevibacterium flavum MJ-233 (FERM BP-1497) cells. The transformants were plated on A-medium agar plates containing 500 g/ml (final concentration) of kanamycin and incubated at 33° C. for 3 days. As a result, the transformants containing the plasmid DNA from any one of the twelve strains grew on the plates containing 500 µg/ml of kanamycin. Thus, it was confirmed that the kanamycin resistance of the transformants depended on the coryneform bacteria chromosomal DNA fragments inserted into the plasmid pPROBE17, and that the inserted DNA fragments were promoter DNA fragments which had greater promoter strengths than the tac promoter in coryneform bacteria cells.

To identify the DNA fragment having a greater promoter strength than the tac promoter, the sizes and nucleotide sequences of the DNA fragments inserted into the plasmid pPROBE17 were determined as follows:

First, the following primer two DNA fragments were chemically synthesized corresponding to nucleotide sequences of the plasmid pPROBE17 present in the upstream and downstream from the EcoRV site, that is, in the 5' and 3'-flanking sequences of the EcoRV site.

Primer DNA for the 5' end GATCAGATCCCAGAAT-TGAT (SEQ ID NO:22)

Primer DNA for the 3' end TGAGCGGGCTTTTTTTTTGAT (SEQ ID NO:23)

Using these synthetic primer DNA sequences, plasmid DNA extracted from each of the twelve transformants was locally amplified by the PCR method (Nature, 324, 163 (1986), PCR condition; 9° C., 1 min.; 37° C., 2 min.; 72° C., 3 min.) using a DNA Thermal Cycler model 480 (Takara Shuzo Co., Ltd.). Thus, the DNA fragment inserted into the plasmid was selectively multiplied many times (i.e., amplified).

The insert DNA fragment thus amplified was electrophoresed on an agarose gel, followed by determining the sizes thereof based on the migration distances thereof on the agarose-gel with reference to the migration distance-size standard curve obtained by the electrophoresis of the pHY marker (Takara Shuzo Co., Ltd.) on the same agarose gel.

The nucleotide sequences of the amplified insert DNA fragment were determined by the dideoxy chain termination method (Proceedings of the National Academy of Science of the United States of America, 74, 5463 (1977)) using the same primers as used in the PCR method and the products of the PCR method as templates.

The results are shown below.

| No. | Plasmid | | Size of insert DNA fragment | Sequence of insert DNA fragment |
|---|---|---|---|---|
| (1) | pPROBE17 | Km5001 | about 130 bp | SEQ ID NO: 1 |
| (2) | pPROBE17 | Km5002 | about 410 bp | SEQ ID NO: 2 |
| (3) | pPROBE17 | Km5003 | about 420 bp | SEQ ID NO: 3 |
| (4) | pPROBE17 | Km5004 | about 240 bp | SEQ ID NO: 4 |
| (5) | pPROBE17 | Km5005 | about 600 bp | SEQ ID NO: 5 |
| (6) | pPROBE17 | Km5006 | about 590 bp | SEQ ID NO: 6 |
| (7) | pPROBE17 | Km5007 | about 430 bp | SEQ ID NO: 7 |
| (8) | pPROBE17 | Km5008 | about 860 bp | SEQ ID NO: 8 |
| (9) | pPROBE17 | Km5009 | about 1,190 bp | SEQ ID NO: 9 |
| (10) | pPROBE17 | Km5010 | about 710 bp | SEQ ID NO: 10 |
| (11) | pPROBE17 | Km5011 | about 1,000 bp | SEQ ID NO: 11 |
| (12) | pPROBE17 | Km5012 | about 740 bp | SEQ ID NO: 12 |

Example 6

Detection of Controllable Promoter DNA Fragment in Coryneform Bacteria Chromosomal DNA 20 µg of the coryneform bacteria chromosomal DNA prepared in Example 4 was completely digested by incubation with the 4-base-sequence recognizing restriction enzymes AluI and HaeIII at 37° C. for 10 hours. Separately, 10 µg of the plasmid pPROBE17 DNA prepared in Example 2 was digested by incubation with the restriction enzyme EcoRV at 37° C. for one hour. After these resultant solutions were incubated at 65° C. for 10 minutes, they were mixed and then incubated at 16° C. for 24 hours in the presence of the T4 DNA ligase, ATP and dithiothreitol to ligate the DNA fragments. The ligation products were introduced into Brevibacterium flavum MJ-233 (FERM BP-1497) by the method described in Example 2. The transformants were selected by plating the resultant bacterial cells on a minimal medium obtained by adding 5 mg/liter of chloramphenicol and 20 g/liter of glucose to BT medium (prepared by dissolving 2 g of urea, 7 g of $(NH_4)_2SO_4$, 0.5 g of $K_2HPO_4$, 0.5 g of $KH_2PO_4$, 0.5 g of $MgSO_4$, 6 mg of $FeSO_4$ $7H_2O$, 6 mg of $MnSO_4$ $4–6H_2O$, 200 g of biotin, 200 µg of thiamine hydrochloride and 16 g of agar into distilled water to obtain 1 liter) and then incubating at 33° C. for 3 days. As a result, 100,000 of chloramphenicol resistant colonies were obtained.

Various methods for detecting different types of controllable promoter DNA fragments are described below.

Example 7

Detection of Controllable Promoter DNA Fragment Inducible by Replacing Glucose with Ethanol in the Medium Transformants isolated in Example 6 were replica-plated on a BT medium containing 20 g/liter of glucose and 100 µg/l of kanamycin (hereinafter, referred to as "GK medium") and a BT medium containing 20 ml/l of ethanol and 100 µg/l of kanamycin (hereinafter, referred to as "EK medium"), and then incubated at 33° C. for 3 days. As a result, four transformants which were unable to grow on GK medium but able to grow on EK medium were obtained. These transformants were named as follows:

| No. | Bacteria strain | Plasmid |
|---|---|---|
| (13) | Brevibacterium flavum MJ233 KE101 | pPROBE17 KE101 |
| (14) | Brevibacterium flavum MJ233 KE102 | pPROBE17 KE102 |

To determine whether the ability of the transformants to grow on a kanamycin-containing medium was caused by the promoter inserted into the plasmid pPROBE17, plasmid DNA was extracted from each of the four transformants and introduced again into coryneform bacteria cells, followed by examining the growth of the thus-obtained transformants on GK medium and EK medium in the same manner as described above. As a result, the transformants containing the plasmid DNA from any one of the four transformants were able to grow on EK medium but not on GK medium, thus confirming that the kanamycin resistance of the transformants substantially depended on the promoter DNA fragment inserted into the plasmid pPROBE17.

Next, to identify the thus-obtained promoters, the sizes and nucleotide sequences of The DNA fragments inserted into the plasmid pPROBE17 were determined by the methods described in Example 5. The results are shown below.

| No. | Plasmid | Size of insert DNA fragment | Sequence of insert DNA fragment |
|---|---|---|---|
| (13) | pPROBE17 KE101 | about 2,300 bp | SEQ ID NO: 13 |
| (14) | pPROBE17 KE102 | about 550 bp | SEQ ID NO: 14 |

Example 8

Detection of Controllable Promoter DNA Fragment Inducible by Replacing Ethanol with Glucose in the Medium Similar to Example 7, transformants isolated in Example 6 were replica-plated on GK medium and EK medium and incubated at 33° C. for 3 days. As a result, one transformant which was able to grow on GK medium but unable to grow on EK medium was obtained. The transformant and the plasmid contained therein were named Brevibacterium flavum MJ233 KG101 and pPROBE17 KG101, respectively.

To determine whether the ability of the transformant to grow on a kanamycin-containing medium was caused by the promoter inserted into the plasmid pPROBE17, plasmid DNA was extracted from the transformant KG101 and introduced into other coryneform bacteria cells, followed by examining the growth of the thus-obtained transformants on GK medium and EK medium in the same manner as described above. As a result, the transformants containing the plasmid DNA from the transformant KG101 were able to grow on GK medium but not on EK medium, thus confirming that the kanamycin resistance of the transformant substantially depended on the promoter DNA fragment inserted into the plasmid pPROBE17.

Next, to identify the thus-obtained promoter, the size and nucleotide sequence of the DNA fragment inserted into the plasmid pPROBE17 KG101 were determined by the methods described in Example 5. The size of the DNA fragment was about 5,500 bp and the nucleotide sequence is listed as SEQ ID NO:15.

Example 9

Detection of Controllable Promoter DNA Fragment Inducible by Replacing with Fructose in the Medium Transformants isolated in Example 6 were replica-plated on GK medium and a ST medium containing 20 g/l of fructose and 100 µg/l of kanamycin (hereinafter, referred to as "FK medium") and incubated at 33° C. for 3 days. As a result, one transformant which was unable to grow on GK medium but able to grow on FK medium was obtained. The transformant and the plasmid contained therein were named *Brevibacterium flavum* MJ233 KF101 and pPROBE17 KF101, respectively.

To determine whether the ability of the transformant to grow on a kanamycin-containing medium was caused by the promoter inserted into the plasmid pPROBE17, plasmid DNA was extracted from the transformant KF101 and introduced into other coryneform bacteria cells, followed by examining the growth of the thus-obtained transformants on GK medium and FK medium in the same manner as described above. As a result, the transformants containing the plasmid DNA from the transformant KF101 were able to grow on FK medium but not on GK medium, thus confirming that the kanamycin resistance of the transformant substantially depended on the promoter DNA fragment inserted into the plasmid pPROBE17.

Next, to identify the thus-obtained promoter, the size of the DNA fragment inserted into the plasmid pPROBE17 KF101 was determined by the method described in Example 5. The size of the DNA fragment was about 2,500 bp and the nucleotide sequence is listed as SEQ ID NO:16.

Example 10

Detection of Controllable Promoter DNA Fragment Inducible by Replacing Combination of Casein Hydrolysates, Yeast Extracts and Glucose with Glucose in the Medium Transformants isolated in Example 6 were replica-plated on GK medium and a BT medium containing 20 g/l of glucose, 1 g/l of yeast extracts, 1 g/l of casein hydrolysates (casamino acids) and 100 µg/ml of kanamycin (hereinafter, referred to as "GYCK medium") and incubated at 33° C. for 3 days. As a result, one transformant which was able to grow on GK medium but unable to grow on GYCK medium was obtained. The transformant and the plasmid contained therein were named *Brevibacterium flavum* MJ233 KG102 and pPROBE17 KG102, respectively.

To determine whether the ability of the transformant to grow on a kanamycin-containing medium was caused by the promoter inserted into the plasmid pPROBE17, plasmid DNA was extracted from the transformant KG102 and introduced into other coryneform bacteria cells, followed by examining the growth of the thus-obtained transformants on GK medium and GYCK medium in the same manner as described above. As a result, the transformants containing the plasmid from the transformant KF101 were able to grow on GK medium but not on GYCK medium, thus confirming that the kanamycin resistance of the transformant substantially depended on the promoter DNA fragment inserted into the plasmid pPROBE17.

Next, to identify the thus-obtained promoter, the size and nucleotide sequence of the DNA fragment inserted into the plasmid pPROBE17 KG102 were determined by the methods described in Example 5. The size of the DNA fragment was about 5,700 bp and the nucleotide sequence is listed as SEQ ID NO:17.

Example 11

Detection of Controllable Promoter DNA Fragment Inducible by Replacing Glucose with Combination of Casein Hydrolysates, Yeast Extracts and Glucose in the Medium Similar to Example 10, transformants isolated in Example 6 were replica-plated on GK medium and GYCK medium and incubated at 33° C. for 3 days. As a result, three transformants which were unable to grow on GK medium but able to grow on GYCK medium were obtained. The transformants and the plasmid contained therein were named as follows:

| No. | Bacteria strain | Plasmid |
|---|---|---|
| (18) | *Brevibacterium flavum* MJ233 KGYC101 | pPROBE17 KGYC101 |
| (19) | *Brevibacterium flavum* MJ233 KGYC102 | pPROBE17 KGYC102 |
| (20) | *Brevibacterium flavum* MJ233 KGYC103 | pPROBE17 KGYC103 |

To determine whether the ability of the transformants to grow on a kanamycin-containing medium was caused by the promoter inserted into the plasmid pPROBE17, plasmid DNA was extracted from each of the three transformants and introduced into other coryneform bacteria cells, followed by examining the growth of the thus-obtained transformants on GK medium and GYCK medium in the same manner as described above. As a result, the transformants containing the plasmid from any one of the three transformants were able to grow on GYCK medium but not on GK medium, thus confirming that the kanamycin resistance of the transformants substantially depended on the promoter DNA fragment inserted into the plasmid pPROBE17.

Next, to identify the thus-obtained promoters, the sizes of the corresponding restriction fragments or nucleotide sequence of the DNA fragment inserted into the plasmid pPROBE17 KGYC101, pPROBE17 KGYC102 and pPROBE17 KGYC101 respectively were determined by the methods described herein above. The results are shown below.

| No. | Plasmid | | Size of insert DNA fragment | Sequence of insert DNA fragment |
|---|---|---|---|---|
| (20) | pPROBE17 | KGYC101 | about 1,110 bp | SEQ ID NO: 18 |
| (21) | pPROBE17 | KGYC102 | about 2,200 bp | SEQ ID NO: 19 |
| (22) | pPROBE17 | KGYC103 | about 2,300 bp | SEQ ID NO: 20 |

---

What is claimed is:

1. An isolated DNA fragment which is obtained from coryneform bacterial chromosomal DNA and which is functional as a promoter in coryneform bacteria cells, wherein the promoter function of said DNA fragment is controllable by: deleting at least one substance from a first culture medium for host coryneform bacteria cells to yield a second culture medium, adding at least one substance to a first culture medium for host coryneform bacteria cells which is assimilable by the host coryneform bacteria cell to yield a second culture medium or replacing at least one substance of a first culture medium for host coryneform bacteria cells with at least one replacement substance which is assimilable by the host coryneform bacteria cells to yield a second culture medium.

2. An isolated promoter DNA fragment as claimed in claim 1, wherein said at least one substance deleted from a first culture medium is, selected from the group consisting of glucose, fructose, ethanol, casein hydrolysates and yeast extracts; said at least one substance added to a first culture medium is selected from the group consisting of glucose, fructose, ethanol, casein hydrolysates and yeast extracts; and said at least one substance replaced in a first culture medium is selected from the group consisting of glucose, fructose, ethanol, casein hydrolysates and yeast extracts; and wherein said at least one substance of said first culture medium which is replaced and said replacement substance are not the same, and said first culture medium and said second culture medium are not the same.

3. An isolated DNA fragment as claimed in claim 2, wherein glucose is replaced with ethanol.

4. An isolated DNA fragment as claimed in claim 2, wherein ethanol is replaced with glucose.

5. An isolated DNA fragment as claimed in claim 2, wherein glucose is replaced with fructose.

6. An isolated DNA fragment as claimed in claim 2, wherein casein hydrolysates and yeast extracts are deleted.

7. An isolated DNA fragment as claimed in claim 2, wherein casein hydrolysates and yeast extracts are added.

8. An isolated promoter DNA fragment as claimed in claim 1, wherein said coryneform bacteria chromosomal DNA is chromosomal DNA obtained from *Brevibacterium flavum* MJ-233 (FERM BP-1497).

9. An isolated DNA fragment which is functional as a promoter in coryneform bacteria cells and includes at least one of SEQ ID Nos:13 and 14:

SEQ ID NO: 13:

| | | | | | | |
|---|---|---|---|---|---|---|
| CTACTTCTTC | TTCACCGAAG | TATTCCTTAG | GGTCGATCTC | GTTACCCTCG | GAGTCCTTCA | 60 |
| CGTTTACGCG | GCAGATAGCC | TGTGCAAGAG | CCTTGCCACG | GCGAACGTCG | GAGAAGAGGT | 120 |
| TCGCGATCTG | GCCGGACTGC | TGCAGCTGAC | CGATGAACTG | GTTTGGGTCC | ATGCCGTAAG | 180 |
| ACTGTGCGGT | GAACAGGATG | TGGTCGGTGA | GCTCCTCGTG | CCGCTGATGC | GACTTCGAGT | 240 |
| CCGATCCAGC | CACCACCGAT | GAGGACCAGC | TTTTTACCTT | CACCGAAGTT | GCCTTGATCG | 300 |
| CGTCAGAGTC | TTCCACGGCG | CGCAGGTAGT | GCACATTAGA | GCCGTCGGCT | CCGGAATTGG | 360 |
| AAGTTTGCGA | CTGCTGAGCA | AGTAGCAAGA | ACTAGTTTGT | CGTAGTTAAT | GGTCTCAGTG | 420 |
| TTTCCGCCAT | CATCAACGGT | GACTTGGCGT | GAACCCGCAT | CAATTGCCGT | GACGCACACC | 480 |
| TTGACGCAGC | GTGACATTGT | TTTCTTTGTA | CCACCCCGCC | GGGTGAACAA | TCGCCTTTTC | 540 |
| AAAGCCTACT | TTTCCCGCCA | TGTACTCCTT | TGACAGCGGT | GGGCGTTCAT | ATGGCAGATG | 600 |
| ATTTTCTGCT | GCGATGAGCG | TGATGGAGCC | TTCATGCCCG | TTTACACGCA | GTGCCTCTGC | 660 |
| GGTTTTCGCT | CCGGCTGAAC | CGCCGCCGAT | GATGACGATG | CTTTGTGGTG | TGCTCATGCT | 720 |
| GTACTCCTAG | TCCCTAAAAA | GTGGACGGTC | AGGCGCAAGG | TCGACCGCAT | GGTCTATACG | 780 |
| CCATGCTAGT | TAAAAGGCCG | AAACCCTCGG | CGAGCGCGCT | AAATACCCGG | CCCCAATTGG | 840 |
| AAGAAGCGAC | GACTAGCCTG | TGGGGACAAA | CTATCTCAAG | AATTTATTCA | ACAAAGGAGT | 960 |
| TCTTCGCACA | TGAAGGAAGT | AGCAGTCAAC | GAAGTCCAG | CAGGCGCGCA | GCTAATGCAC | 1020 |
| TGTCACTGTT | TCGACGTGAT | GTGCATCGGT | TTACGTGGTG | GCGTGGTTCA | CACATTGCTC | 1080 |
| CATCGGGCAT | TGGTGCGTCA | ATCGGTTTGG | GTTTTTAAGT | TTTCTGCGGG | GGTGGTCACC | 1140 |
| CCTGTTGTGA | ACTTTGCAAA | GTTATGACTT | CGCAGAAAAA | GTCGGCGGGG | GAGTTGCTAG | 1200 |
| TACGGATGTA | CTGGGCAAAT | GCTCTGAAAT | GGGAAAATGC | AGGCACCACA | ACTTTCCGTA | 1260 |
| GTTTTGAAGG | TGTGACCTAG | ATAAAAGTCG | GGGTAGGCG | GGGGTAAATG | ACTAGGTAAA | 1320 |
| GGTTCGCAAA | CCCCCTTTTG | TTGGTGACGG | TGATCACTTA | GTCTGATCAC | ATCGCCAAAC | 1380 |
| ACGATAAGGG | TTGAAATCGTA | AAGAAGAGCG | TCCAGAGGTA | GCACCTAGAT | GCCAGAGTGC | 1440 |
| TTTTCTTAAA | AGAGTTTTCA | CAACCGTTAA | GGCGTAGCC | AAACAAGAAG | CATTCGCATT | 1500 |
| NCAGCTTCTG | GTTTAGGCAC | AGGTCATCTA | AAACCCATGC | TTTAAAAGGA | GCCTTCAATG | 1560 |
| ACTGAACAGG | AACTGTTGTC | TGCTCAGACT | GCCGACAACG | CTGGAACTGA | CAGCACCGAA | 1620 |
| CGCGTTGACG | CGGGCGGAAT | GCAGGTTGCA | AAAGTTCTCT | ACGACTTTGT | AACCGAAGCG | 1680 |
| GTACTCCCTC | GCGTGGGTGT | GGATGCGGAA | AAGTTCTGGT | CCGGATTCGC | CGCCATCGCC | 1740 |
| CGGGACCTCA | CCCCACGCAA | CCGCGAACTG | CTTGCTCGTC | GCGATGAACT | GCAGACGCTT | 1800 |
| ATCGACGACT | ACCACCGCAA | CAACTCCGGC | ACCATCGACC | AAGACGCGTA | CGAGGATTTC | 1860 |
| CTTAAAGAAA | TCGGATACTT | GGTTGAAGGG | CCAGAAGCTG | CAGAAATCCG | TACCCAAAAC | 1920 |
| GTCGATACGG | AAATCTCCAG | CACCGCAGAC | CTCAGCTGGT | TGTGCCAATT | CTGAACGCAC | 1980 |
| GTTCGCGCTG | AATGCTGCCA | ATGCTCGTTG | GGGTTCCCTC | TACGATGCGT | TGTACGGCAC | 2040 |
| CAACGCCATC | CCAGAAACTG | ATGGCGCTGA | AAAGGGCAAG | GAGTACAACC | CGGTCCGCGG | 2100 |
| CCAGAAGGTC | ATCGAGTCGG | GTCGTCAATT | CCTCGACAGC | GTTGTCCCAC | TGGACGGGTG | 2160 |
| CTTCGCATGC | CGATCTTGAG | AAGTACAACA | TCACGGATGG | AAA | | 2203 |

SEQ ID NO: 14:

| | | | | | | |
|---|---|---|---|---|---|---|
| CCTCATGGAT | GTTGACATCG | ATATGGATTC | CGACATCTGA | GCAGATCCTC | TCCTGGCGGA | 60 |
| CACAGACGCA | TCCCTGCTCT | CCCTGGAAGC | TGGCACCTGT | GACCGTTGCC | TTCGACACGA | 120 |
| CACATGCTGA | CCACCCTGGA | GAACTCCGGC | CTATCGTGCC | GATCGTTCCA | GGCGCTGTGA | 180 |
| TTTTTGATTT | GTTGGTGGGC | GATCCCAAAA | ACAGGCCGCT | GAGAAAGTTT | TCCACACTAA | 240 |
| AATAGTGTGA | TTCTGCCGAA | TCTGTTGTTT | TACTTTTGAA | ACTGCGGGAT | CATGAAAAGT | 300 |
| AGTGAAAAGT | GAATTTTAGT | TCTGTGCTTT | CTCTTCCCTT | TAAGTGAACC | TTTTGTTGGA | 360 |
| TCTTCATTAA | AAAAATGAAA | ACCTCGTCGG | AATGCAACTT | GGGATCACTG | TCTCGGGCAA | 420 |
| GAAACGGCCT | TAAAAAAGGG | GAGTGATTGT | GAGTGCTTGA | TTTCTTAGCT | GCGAACCCGC | 480 |
| TTGATTGCTG | CTTGGTGGTT | ATTTTGGCCA | CGGGTGACCA | CTCCCAGACT | CAGCTGCCAG | 540 |
| GTGGTCAGTG | G | | | | | 551 | wherein the promoter function of said DNA fragment is controllable by replacing glucose contained in a first culture medium for host coryneform bacteria cells containing said DNA fragment with ethanol.

10. An isolated DNA fragment which is functional as a promoter in coryneform bacteria cells and includes SEQ ID NO:15:

| SEQ ID NO: 15: | | | | | | | |
|---|---|---|---|---|---|---|---|
| GATCCTCATG | GATGTTGACA | TCGATATGGA | TTCCGACATC | GAGCAGATCC | TCTCCGGCGG | 60 |
| ACACGACGCA | TCCCTGCTCT | CCCTGGAAGC | TGGCACCTGT | GACGTTGCCT | TCGCACACGA | 120 |
| CACCATGCTG | ACCACCCTGG | AGAACTCCGG | CCTATCGTGC | CGATCGTTCC | AGGCGCTGTG | 180 |
| ATTTTTGATT | TGTTGGTGGG | CGATCCCAAA | AACAGGCCGC | TGAGAAAGTT | TTCCACACTA | 240 |
| AAATAGTGTG | ATTCTGTCCG | AATCTGTTGT | TTTAGTTTTG | AAACTGCGGG | ATCATGGAAA | 300 |
| GTAGTGAAAA | GTGAATTTTA | GTTCTGTGCT | TTCTCTGCCC | TTTAAGTGAA | CCTTTTGTTG | 360 |
| GATCTTGCAT | TAAAAAAATG | AAAACCTCGT | CGGGAATGCA | ACTTGGGATC | ACGTCTCGGG | 420 |
| CAAGAAACGT | CCTTAAAAAA | GGGGAGTGAT | TGTGAGTGCT | TGATTTCTTA | GCTGCGAACC | 480 |
| CGCTGATTGC | GCTGGTGGTT | ATTTTGGCCA | CGGTGACCAC | TCCCGACTCG | GCGCCGGTGG | 540 |
| TCGTGGATC | | | | | | 549 | wherein the promoter function of said DNA fragment is controllable by replacing ethanol contained in a first culture medium for host coryneform bacteria cell containing said DNA fragment with glucose.

11. An isolated DNA fragment which is functional as a promoter in coryneform bacteria cells and includes SEQ ID NO:16:

| SEQ ID NO: 16: | | | | | | | |
|---|---|---|---|---|---|---|---|
| TGGGGCCGGT | GGCAATGCAT | CAGGGAGATT | TGGATATACG | GCCCACAATT | CTTTGGTTCC | 60 |
| GGTCGATGGG | GTAGTGAAGG | TGACACGGGA | TCCGATGGTG | ACGTTGCTGA | TCTCTGTTTC | 120 |
| TTTTACATTC | GCGGTGATCT | TCAGTTCGGA | ATCATCAGCA | ACACTCAACA | GTGCGCCGGC | 180 |
| TGCTGGTTGA | CCTTGGGCTG | CCTGCCACGG | ATGAACAATG | CCTGAGTATG | GGGATCGACG | 240 |
| GTGGTGTGTT | GATATCATCC | GAACTGGGAC | GTGGATCTGGT | GGCGCTTAAT | ATCTACTGAT | 300 |
| GCAACCTAAA | GTGCATAATG | CGCTTATTTT | CTCCAATGGT | GTTGGTGAAA | ATCCCGTCTC | 360 |
| GAGCCAAGTT | TGCGCTTGTG | TGCTATTGGG | CTCATCACGG | CGCCTGTGCA | GCGGCTAGTC | 420 |
| TGAGTCAACT | TTTCCGAGTG | AATCAATGTA | GATCCGCTCG | GCTTTTTCTA | GACCTTCAGT | 480 |
| GGTGGATGCA | ACGCGTCGCT | CAGTTTCCTC | CAAAACGGTG | TAGGACTGCA | ACTTAGGCTG | 540 |
| GTCCTGGCTA | GGCCACTGGA | GGTTTTGGAA | GCAATGATGT | ACCGGCCTGC | AACCTTGCTA | 600 |
| TAATGCGGGG | TACACGGTTT | CCACTGCGGC | GCGTGCTTCT | GCTGCAGGAC | TGCCTCTAGG | 660 |
| TCACCTTCCA | ACGCGGGCTT | GAGCAAGTTC | GGATTCCGAG | AAGCAAATAT | CTCTCTCATC | 720 |
| GAAAGCCATT | TGCATCGTGA | GGTTCTGCGA | TCGTGGTGAA | AGTCAAAGTC | GGCGAGCGTC | 780 |
| AGTCGGTCAA | TTTCAAGCAG | CATCCAGTCG | TTCAATTTCA | GCAGCATCTG | CTTGCTCACG | 840 |
| GGCTGCCTTG | AGAGCATCCG | ATTCAGCGAC | CATGGTGGAA | TCCAATCCGC | ATCCACATCT | 900 |
| CGGTTCTTCG | CTTCAAAACT | GCGGATCGAT | CCTGATATGC | TGTGAGGACG | CCGAACAGGG | 960 |
| ACGGCGCGAG | TTGATCTCCG | GGTCAAACCA | TATCAAGAGT | CCCTGGCTGT | TATATGTTCT | 1020 |
| GCGCTGCGCG | TGGATTCGGT | CGCATGTTCA | CGCGATTGTT | GGATAGTTCA | TCACTGTCGT | 1080 |
| TCAGGGAGAG | GATCACTCAG | CCACACTGTC | AGTGCACACG | GTACACCGAA | CCGGAAGTGG | 1140 |
| GACGGACAGT | ACCTGTGTAA | TGGTGGTGGT | TCGCGCAGCT | TCAATATTCC | GTTGACTCTC | 1200 |
| AAACAAAGGA | ATTAAATATT | AAGCGCGCCC | CCCCTTAAAT | TCCTTAAAAA | ACTTAAATCC | 1260 |
| CAGGGAACTC | CCAATCAAAA | GAAACCGGGG | GTCCCTTTAA | CCAAATAATC | TGCACCCATG | 1320 |
| ATAAAATAGC | CAGGCGCATG | GTATTCTGGG | CCAGAAACAA | GTGTATCCGC | ATTAATGCCC | 1380 |
| CAAACCAGTA | CCCGGGAACC | TTCAAAGTCT | TACAAAGCTA | ACCAAATGCA | GGTCGAAATC | 1440 |
| CATCCAGACA | TCCGGACCAC | TACTTGTTTC | CCTAGAACCC | CCATTCATCA | CTCCGAATGG | 1500 |
| GTATGCTGAC | GATAATGAGT | CCTTATCGAC | AGGCTGATTC | TGCTGGAACC | CCACATTTGG | 1560 |
| AACGTACGCG | AGAACCTTCG | GCGAAGCTTT | TCGGTCGCGG | CCGTTATCTT | TTTAAGAGGA | 1620 |
| GAAATTTTAG | ATGAGCACGT | CCACCATCAG | GGTTGCCATT | GCCGGAGTCG | GAAATGCGCG | 1680 |
| ACCTCCCTCA | TTCAGGGTGT | GGAATATACC | GAAATGCGGA | ACCTCCGAAA | TGTCCCGGTT | 1740 |
| TGCTGCACTT | CAATTCGGTG | ATTACCACGT | TGGCGCATGA | TTCGTTGCCG | GTTCACGTCG | 1800 |
| ACGCCGAAAA | GTAGCAGGAA | TTCCCCGCAC | GGGGTTACAA | ACTGCATTAT | GAAATGCCAG | 1860 |
| TCCGAGCCGA | ATAACGGTGT | TGGCCGATTT | GAGGCTGGGT | TCATACGGGA | CATGACGGTC | 1920 |
| ACGCGGGCAT | GGCGTGTCAG | GGTTATGCGG | AAAACCCTTT | TTGAGCCCAC | CTCATGGTCC | 1980 |
| AGAGCGCAAT | TTCGGAAGCG | AAAATTCTAC | GCACAAGCGC | CATCGATTGC | AGTGCGCCTT | 2040 |
| TGTCAACGCT | CTCCCAGTAT | TCATCGCCTC | CGACCCTGAG | TGGGCTAAGA | AGTTAACTGA | 2100 |
| GGCTGGCATC | CCAATTGTTG | GCGATGACAT | CAAATCCCAG | ATCGGTGCAA | CCATCACCCA | 2160 |
| CCGTGTCCTC | GCACGCCTTT | TTGAAGAACG | TGTCGTTCGC | GTAGATCGCC | ACCTGCCGGA | 2220 |
| CCATTCTGGG | AACTGGACAG | CAGAATAT | | | | 2248 | wherein the promoter function of said DNA fragment is controllable by replacing glucose contained in a first culture medium for host coryneform bacteria cells containing said DNA fragment with fructose.

12. An isolated DNA fragment which is functional as a promoter in coryneform bacteria cells and includes SEQ ID NO:17:

SEQ ID NO: 17:

| GATCCAAAAA | GTCGGCGCAG | CTGACTGGAG | CTTCTGGGAA | GCCAAAGTCC | GCGCCCGCGA | 60 |
| CTACGCCCTG | GACGAAACCG | AACTGCGCAA | CTACTTCCCA | CTGAACCAAG | TACTCTGTGA | 120 |
| CGGCGTCTTC | TTCGCTGCTA | ACCGCCTCTA | CGGAATCACC | GTGGAACCAC | GCCCTGACCT | 180 |
| GCGCGGTTAC | GCCGAGGGCG | TGGACGTCTG | GGAAGTCCTC | GATTCTGACG | GCTCCGGCAT | 240 |
| CGGCCACAAG | TGCGATGCGC | CCCTTCCGGG | TCGGCGAGGC | GGTGATCTTG | CGGTGTCTAC | 300 |
| CTGGGGTCGA | CTGTCGAGTC | GTGGTCCGCA | TTGAACTTCT | TTCCGTGGTG | TTTATCTTTT | 360 |
| CATCACAAAC | AATCACGACG | GTATACCCAT | CGGAGACGAT | ATCGTGATCT | TTCTGTTACC | 420 |
| TGCGGAAGGT | AACATTAGTA | TTTCAACTCG | ACAGAGTCCA | TCCTGGAAGC | GTGTATGACG | 480 |
| ATTTCTTCAC | ACATTCTTTA | CAATGGCCTT | TCGTGCGATA | ATGCTAGGCA | TGCTTCGATG | 540 |
| GACTACAGCA | GGTGAATCCC | ACGGATC | | | | 567 | wherein the promoter function of said DNA fragment is controllable by deleting casein hydrolysates and yeast extracts contained in a first culture medium for host coryneform bacteria cell containing said DNA fragment.

13. An isolated DNA fragment which is functional as a promoter in coryneform bacteria cells and includes at least one of SEQ ID Nos:18 to 20:

SEQ ID NO: 18:

| CTGGTTTTGG | CGGTAGGCAA | ACATGCCTTT | GAGGGTAGAT | GCCGGTAGGC | GGAGTGCTCA | 60 |
| CGGAATCTGT | GATGAGTGTG | CCGCCGTCTT | GGTCGATGAA | ATTGTGCACG | TGACGCCAGT | 120 |
| TTGCGAGGGC | CTTTACGGGG | GCGGTCAGAC | AGACGTCGGT | GAAGCGTGAA | CCATTCAAAA | 180 |
| ATCCCGATAA | ATCATGGCGC | GCCACCCATT | TAAGTCCCGC | AGGAAGGCTG | AAAATGGTGG | 240 |
| TGCCATCGGA | GAGGCGTTCT | GCCTGCGCAA | TGGGGTTAAG | GGGGACGAAT | GGCGGAGTCA | 300 |
| GACGTGTGAC | AGCGCCCTTA | CGGGTATGCC | AATCCCAGAC | CATTTCTCGG | GGAAAAGGAA | 360 |
| TAAAATGGCT | TGTGGTCAGA | CTCACAGGGG | CTTCTCCAAG | TCAGTGGATT | TATGAGGTCC | 420 |
| CAGTGGGTAC | ACACCGGGTG | TCCTACAACG | ATCAATTGTC | ACAGATTCGA | CTGGCATGCT | 480 |
| GTACCATCTG | CTTTAAGCAT | TTTGGTGTTT | CACTGTTGTT | AACAGTGTTT | CACCGTGGAG | 540 |
| CACTACCTAA | AGATCATAGT | CAGCATCTTG | GGGTGAATGT | GACACGGTAC | GCTATAG6GT | 600 |
| CAGACAACAA | CCAGGAAACT | GGTCGTTGCA | GAGTTTTGCA | AAAATTGGAC | ATCCTTTAAC | 660 |
| GGACCGCACA | GAGAGGCGGG | AAGGAGGTCA | CGATGAGCGA | ACGTAATAGT | GCTGTACTAG | 720 |
| AACTCCTCAA | TGAGGACGAC | GTCAGCCGTA | CCATCGCACG | CATCGCGCAC | GACATTATTG | 780 |
| AGAAAACCGC | GCTTGATTCC | AAATACGCGG | ATCGGGTCAT | GTTGTTAGGC | ATTCCTTCAG | 840 |
| GTGGAGTCCC | GCTGGCCCGA | AGGCTTGCTG | AAAAGATCGA | AGAATTTTCC | GGCGTTTCGG | 900 |
| TAGATACCGG | CGCTGTTGAT | ATCACCTTGT | ACAGGGATGA | TCTTCGAAAC | AAACCGCACC | 960 |
| GCGCACTGCA | GCCCACCTCT | ATTCCGGCAG | GTGGTATCGA | TAACACCACC | GTGATTTTGG | 1020 |
| TGGATGATGT | GCTGTTTTCC | GGTCGTACTA | TNCGCGCTGC | ACTTGATGCA | TTGCGCGACG | 1080 |
| TTGGACGCCC | AAACTATATC | CAATTAG | | | | 1107 |

SEQ ID NO: 19:

| GGATCCGGTA | ACCGTTTTTA | TCAGGCTCTG | GGAGGCAGAA | TAAATGATCA | TATCGTCAAT | 60 |
| TATTACCTCC | ACGGGGAGAG | CCTGAGCAAA | CTGGCCTCAG | GCATTTAAGA | AGCACACGGT | 120 |
| CACACTGCTT | CCGGTAGTCA | ATAAACCGGT | AAACCAGCAA | TAGACATAAG | CGGCTATTTA | 180 |
| ACGACCCTGC | CCTGAACCGA | CGACCGGGTC | GAATTTGCTT | TCGATATCTG | CCATTCATCC | 240 |
| GCTTATTATC | ACTTATTCAG | GCGTAGAACC | AGGCGTTTAA | GGGCACCAAT | AACTGCCTTA | 300 |
| AAAAAATTAC | GCCCGCCCTG | CCACTCATCG | CAGTACTGTT | GTAATTCATT | AAGCATTCTG | 360 |
| CCGACATGGG | AGGCCATCAC | AAACGGGCAT | GATGAACCTG | AATCGCCAGC | GGGCATCAGC | 420 |
| ACTTGGTCGC | CTTGCGTATA | AATATTTGCC | CCTGGTGGAA | AACGGGGGGG | AAGAGGTTGT | 480 |
| CCCATATTTG | GCCACGGTTT | AAATCAAAAT | TGGTGGAACT | CACCCTGGGT | TTGGCTAGCG | 540 |
| ATCCGGGTTG | ACATCTGCAG | GCGGGAAATT | GAAAAGGCCG | GATAAAACTG | GTGCCTATTT | 600 |
| CCTTTAACGG | TCTTTAAAAA | AGGCCCGTAA | TACCCAACTG | AAACGGTCTG | GTTATAGTAA | 660 |
| CATTGGACAA | CTGGACTGGA | AATGCCCTCC | AAATGGTCCT | TTACGATGCC | CAATTGGGGA | 720 |
| TATATCCAAC | GGTGGTATAA | CCCAGTGATT | TTTTTTCCTC | CCATTTTTAG | CTTCCTTTAG | 780 |
| CTCCTGAAAA | TCTCGATAAC | TCAAAAAAAT | ACGCCCGGTA | GTGATCTTAT | TTCATTATGG | 840 |
| TGAAAGTTGG | AACCTCTTAC | GTGCCGATCA | ACGTCTCATT | TTCGCCAAAA | GTTGGCCCAG | 900 |
| GGCTTCCCGG | TATCAACAGG | GACACCAGGA | TTATTTATTC | TGCGAAGTGA | TCTTCCGTCA | 960 |
| CAGGTATTTA | TTCGGCGCAA | AGTGCGTCGG | GTGATGCTGC | CAACTTACTG | ATTTAGTGTA | 1020 |
| TGATGGTGTT | TTTGAGGTGC | TCCAGTGGCT | TCTGTTTCTA | TCAGCTCTCC | CTCCTGTTCA | 1080 |
| CGTATTGACG | GGGTGGTGCG | TAACGGAAAA | GCACCGCCGG | ACATCACCGG | ATCTCAAGAA | 1140 |
| GACCTTTGAA | CTGTTCAACG | GATCCCCAGG | GGCAGGCGGT | ACACCGCGCC | CTCGGACGTA | 1200 |
| TCGGAGTTTC | TGGCGTTTCC | GATGTCCGTC | AGGGAAAGCG | CTTCGAGCTT | GAGGTAGATG | 1260 |
| ATTCCGTCAC | CGAAGCTGAC | CTAAAGAAAA | TTGCTGAAAC | CCTCCTCGCA | AACACCGTCA | 1320 |
| TCGAAGACTT | CGATGTGGTG | GGAGTTGAGG | TCGCGAAGTG | AGCGCCAAAA | TCGGTGTCAT | 1380 |
| TACCTTCCCA | GGCACCCTTG | ACGATGTAGA | TGCAGCACGC | GCTGTTCGCA | TCGCAGGTGC | 1440 |
| AGAAGTAATC | AGCCTGTGGC | ACGCTGACGA | GGATCTCAAG | GGCGTCGACG | CAGTTGTCGT | 1500 |
| TCCCGGTGGA | TTCCTCCTAC | GGCGATTACC | TGCGCACCGG | TGCAATCTCT | GCACTGGCGC | 1560 |
| CAGTAATGCA | GTCCGTGATT | GAGCAGGCCG | GTAAGGGTAT | GCCAGTCTTG | GGCATTTGCA | 1620 |
| ACGGCTTCCA | GATCCTCACC | GANGCACGCC | TGCTTCCAGG | CGCGCTGACC | CGCAACAAGG | 1680 |
| GTCTGCACTT | TCACTGTGTA | GACGCACACC | TCGTTGTAGA | GAACAACACC | ACTGCATGGA | 1740 |
| CCAACACTTT | GGAAAAGGGG | CAGCAGATCC | TTATTCCTGC | AAAGCACGGT | GAAGGTCGCT | 1800 |
| TCCAGGCAGA | CGGCAGAGAC | CATTCGCCCA | GCTTTGAGGG | TGAAGGCCGC | GTGGTGTTCC | 1860 |
| GTTACAACGA | TAACTTCAAC | GGTTTCCGTA | GACCTACCAA | GCCGGTATCA | CTAATGAAAC | 1920 |
| TGGTCGCATC | GTCGGTCTCA | TGCCGCACCC | GGAACATGCC | GTCGAAAAGC | TAACCGGCCC | 1980 |
| ATCTATTGAT | GGCCTGGAGC | TGTTCCTGTC | CGCCGTTGGC | ACCATCGCGG | CTTAAGAGGA | 2040 |

| | | | | | | |
|---|---|---|---|---|---|---|
| GTCAAAATAT | GAGCACTTTT | GTCAATGACA | CCGTCGAGAG | CAATCAAGAC | CCCTGAGATC | 2100 |
| AATTCTGGGA | TCTGA | | | | | 2115 |

SEQ ID NO: 20:

| | | | | | | |
|---|---|---|---|---|---|---|
| ATATTCTGCT | GTCCAGTTCC | CAGAATGGTC | CGGCAGGTGG | CGATCTACGC | GAACGACACG | 60 |
| TTCTTCAAAA | AGGCGTGCGA | GGACACGGTG | GGTGATGGTT | GCACCGATCT | GGGATTTGAT | 120 |
| GTCATCGCCA | ACAATTGGGA | TGCCAGCCTC | AGTTAACTTC | TTAGCCCACT | CAGGGTCGGA | 180 |
| GGCGATGAAT | ACTGGGAGAG | CGTTGACAAA | GGCGCACTGC | AATCGATGGC | GCTTGTGCGT | 240 |
| AGAATTTTCG | CTTCCGAAAT | TGCGCTCTGG | ACCATGAGGT | GGGCTCAAAA | AGGGTTTTCC | 300 |
| GCATAACCCT | GACACGCCAT | GCCCGCGTGA | CCGTCATGTC | CCGTATGAAC | CCAGCCTCAA | 360 |
| ATCGGCCAAC | ACCGTTATTC | GGCTCGGACT | GGCATTTGAT | AATGCAGTTT | GTAACCCCGT | 420 |
| GCGGGGAATT | CCTGCTACTT | TTCGGCGTCG | ACGTGAACCG | GCAACGAATC | ATGCGCCAAC | 480 |
| GTGGTAATCA | CCGAATTGAA | GTGCAGCAAA | CCGGGACATT | TCGGAGGTTC | CGCATTTCGG | 540 |
| TATATTCCAC | ACCCTGAATG | AGGGAGGTCG | CGCATTTCCG | ACTCCGGCAA | TGGCAACCCT | 600 |
| GATGGTGGAC | GTGCTCATCT | AAAATTTCTC | CTCTTAAAAA | GATAACGGCC | GCGACCGAAA | 660 |
| AGCTTCGCCG | AAGGTTCTCG | CGTACGTTCC | AAATGTGGGG | TTCCAGCAGA | ATCAGCCTGT | 720 |
| CGATAAGGAC | TCATTATCGT | CAGCATACCC | ATTCGGAGTG | ATGAATGGGG | GTTCTAGGGA | 780 |
| AACAAGTAGT | GGTCCGGATG | TCTGGATGGA | TTTCGACCTG | CATTTGGTTA | GCTTTGTAAG | 840 |
| ACTTTGAAGG | TTCCCGGGTA | CTGGTTTGGG | GCATTAATGC | GGATACACTT | GTTTCTGGCC | 900 |
| CAGAATACCA | TGCGCCTGGA | TATTTTATCA | TGGGTGCAGA | TTATTTGGTT | AAAGGGACCC | 960 |
| CCGGTTTCTT | TTGATTGGGA | GTTCCCTGGG | ATTTAAGTTT | TTTAAGGAAT | TTAAGGGGGG | 1020 |
| GCGCGCTTAA | TATTTAATTC | CTTTGTTTGA | GAGTCAACGG | AATATTGAAG | CTGCGCGAAC | 1080 |
| CACCACCATT | ACACAGGTAC | TGTCCGTCCC | ACTTCCGGTT | CGGTGTACCG | TGTGCACTGA | 1140 |
| CAGTGTGGCT | GAGTGATCCT | CTCCCTGAAC | GACAGTGATG | AACTATCCAA | CAATCGCGTG | 1200 |
| AACATGCGAC | CGAATCCACG | CGCAGCGCAG | AACATATAAC | AGCCAGGGAC | TCTTGATATG | 1260 |
| GTTTGACCCG | GAGATCAACT | CGCGCCGTCC | CTGTTCGGCG | TCCTCACAGC | ATATCAGGAT | 1320 |
| CGATCCGCAG | TTTTGAAGCG | AAGAACCGAG | ATGTGGATGC | GGATTGGATT | CCACCATGGT | 1380 |
| CGCTGAATCG | GATGCTCTCA | AGGCAGCCCG | TGAGCAAGCA | GATGCTGCTG | AAATTGAACG | 1440 |
| ACTGGATGCT | GCTTGAAATT | GACCGACTGA | CGCTCGCCGA | CTTTGACTTT | CACCACGATC | 1500 |
| GCAGAACCTC | ACGATGCAAA | TGGCTTTCGA | TGAGAGAGAT | ATTTGCTTCT | CGGAATCCGA | 1560 |
| ACTTGCTCAA | GCCCGCGTTG | GAAGGTGACC | TAGAGGCAGT | CCTGCAGCAG | AAGCACGCGC | 1620 |
| CGCAGTGGAA | ACCGTGTACC | CCGCATTATA | GCAAGGTTGC | AGGCCGGTAC | ATCATTGCTT | 1680 |
| CCAAAACCTC | CAGTGGCCTA | GCCAGGACCA | GCCTAACTTG | CAGTCCTACA | CCGTTTTGGA | 1740 |
| GGAAACTGAG | CGACGCGTTG | CATCCACCAC | TGAAGGTCTA | GAAAAAGCCG | ACCGGATCTA | 1800 |
| CATTGATTCA | CTCGGAAAAG | TTGACTCAGA | CTAGCCGCTG | CACAGGCGCC | GTGATGAGCC | 1860 |
| CAATAGCACA | CAAGCGCAAA | CTTGGCTCGA | GACGGGATTT | TCACCAACAC | CATTGGAGAA | 1920 |
| AATAAGCGCA | TTATGCACTT | TAGGTTGCAT | CAGTAGATAT | TAAGCGCCAC | CAGATCACGT | 1980 |
| CCCAGTTCGG | ATGATATCAA | CACACCACCG | TCGATCCCCA | TACTCAGGCA | TTGTTCATCC | 2040 |
| GTGGCAGGCA | GCCCAAGGTC | AACCAGCAGC | CGGCGCACTG | TTGAGTGTTG | CTGATGATTC | 2100 |
| CGAACTGAAG | ATCACCGCGA | ATGTAAAAGA | AACAGAGATC | AGCAACGTCA | CCATCGGATC | 2160 |
| CCGTGTCACC | TTCACTACCC | CATCGACCGG | AACCAAAGAA | TTGTGGGCCG | TAT | 2213 | wherein the promoter function of said DNA fragment is controllable by adding to a first culture medium for the host coryneform bacteria cells containing said DNA fragment casein hydrolysates and yeast extracts.

\* \* \* \* \*